US007387776B2

(12) United States Patent
Keler et al.

(10) Patent No.: US 7,387,776 B2
(45) Date of Patent: Jun. 17, 2008

(54) HUMAN MONOCLONAL ANTIBODIES AGAINST CD30

(75) Inventors: Tibor Keler, Ottsville, PA (US); Robert Graziano, Frenchtown, NJ (US); John Treml, Philadelphia, PA (US); Yashwant M. Deo, East Brunswick, NJ (US)

(73) Assignee: Medarex, Inc., Princeton, NJ (US)

( * ) Notice: Subject to any disclaimer, the term of this patent is extended or adjusted under 35 U.S.C. 154(b) by 231 days.

(21) Appl. No.: 10/338,366

(22) Filed: Jan. 7, 2003

(65) Prior Publication Data

US 2004/0006215 A1    Jan. 8, 2004

Related U.S. Application Data

(60) Provisional application No. 60/347,649, filed on Jan. 9, 2002, provisional application No. 60/404,427, filed on Aug. 19, 2002, provisional application No. 60/431,684, filed on Dec. 6, 2002.

(51) Int. Cl.
*A61K 39/395* (2006.01)
*C07K 16/46* (2006.01)
*C07K 16/24* (2006.01)
*C07K 16/00* (2006.01)

(52) U.S. Cl. ............... 424/133.1; 424/144.1; 424/154.1; 424/155.1; 530/387.3; 530/388.23; 530/388.7; 530/391.7

(58) Field of Classification Search .......... 530/388.23, 530/387.3, 388.15, 391.7, 388.7; 424/142.1, 424/144.1, 152.1, 155.1
See application file for complete search history.

(56) References Cited

U.S. PATENT DOCUMENTS

| 5,165,923 | A | 11/1992 | Thorpe et al. ........... 424/85.91 |
| 5,643,759 | A | 7/1997 | Pfreundschuh ........... 435/70.21 |
| 5,866,372 | A | 2/1999 | Stein et al. ................ 435/69.3 |
| 6,033,876 | A | 3/2000 | Lemke et al. .............. 435/69.6 |
| 6,143,869 | A | 11/2000 | Goodwin et al. ........... 530/350 |
| 6,632,927 | B2* | 10/2003 | Adair et al. ............. 530/387.3 |
| 2002/0064527 | A1 | 5/2002 | Mohler et al. ........... 424/144.1 |
| 2005/0054055 | A1* | 3/2005 | Kucherlapati et al. ... 435/70.21 |

FOREIGN PATENT DOCUMENTS

| EP | 657533 A1 | 6/1995 |
| EP | 613497 B1 | 7/1997 |
| EP | 805871 B1 | 11/1999 |
| WO | WO 91/07437 A2 | 5/1991 |
| WO | WO 91/07941 A2 | 6/1991 |
| WO | WO 92/03918 A1 | 3/1992 |
| WO | WO 93/10232 A1 | 5/1993 |
| WO | WO 94/04189 | 3/1994 |
| WO | WO 94/25585 A1 | 11/1994 |
| WO | WO 96/22384 A1 | 6/1996 |
| WO | WO 97/17374 A1 | 5/1997 |
| WO | WO 98/24884 A1 | 6/1998 |
| WO | WO 99/40187 A1 | 8/1999 |
| WO | WO 01/11059 A1 | 2/2001 |
| WO | WO 02/11767 A3 | 2/2002 |
| WO | WO 02/17979 A2 | 3/2002 |
| WO | WO 02/17979 A3 | 3/2002 |
| WO | WO 02/43661 A2 | 6/2002 |

OTHER PUBLICATIONS

Rudikoff et al Single amino acid substitution altering antigen-binding specificity. Proc Natl Acad Sci U S A. Mar. 1982;79(6):1979-83.*
Panka et al. Variable region framework differences result in decreased or increased affinity of variant anti-digoxin antibodies. Proc Natl Acad Sci U S A. 85(9):3080-3084, 1988.*
Andreesen, R., et al. "A Hodgkin cell-specific antigen is expressed on a subset of auto- and alloactivated T (helper) lymphoblasts" *Blood* Jun. 1984; 63(6):1299-302.
Barth, S., et al. "Ki-4(scFv)-ETA', a new recombinant anti-CD30 immunotoxin with highly specific cytotoxic activity against disseminated Hodgkin tumors in SCID mice" *Blood* Jun. 15, 2000;95(12):3909-14.
Bowen, M., et al. "Functional effects of CD30 on a large granular lymphoma cell line, YT. Inhibition of cytotoxicity, regulation of CD28 and IL-2R, and induction of homotypic aggregation" *J Immunol.* Dec. 1, 1993;151(11):5896-906.
Burns, B., et al. "Ki-1-positive non-Hodgkin's lymphomas. An immunophenotypic, ultrastructural, and morphometric study" *Am J Clin Pathol.* Mar. 1990;93(3):327-32.
Carde, P., et al. "Immunoscintigraphy of Hodgkin's disease: In vivo use of radiolabelled monoclonal antibodies derived from Hodgkin cell lines" *Eur J Cancer.* Apr. 1990;26(4):474-9.
Chiarle, R., et al. "CD30 in normal and neoplastic cells" *Clin Immunol.* Feb. 1999;90(2):157-64.
de Bruin, P.C., et al. "CD30 expression in normal and neoplastic lymphoid tissue: biological aspects and clinical implications" *Leukemia* Oct. 1995;9(10):1620-7.
Durkop, H., et al. "Molecular cloning and expression of a new member of the nerve growth factor receptor family that is characteristic for Hodgkin's disease" *Cell* Feb. 7, 1992;68(3):421-7.
Eckert, F., et al. "Follicular lymphoid hyperplasia of the skin with high content of Ki-1 positive lymphocytes" *Am J Dermatopathol.* Aug. 1989;11(4):345-52.
Engert, A., et al. "Treatment of advanced Hodgkin's lymphoma: standard and experimental approaches" *Semin Hematol.* Jul. 1999;36(3):282-9.

(Continued)

*Primary Examiner*—Maher M. Haddad
(74) *Attorney, Agent, or Firm*—Lahive & Cockfield, LLP; Jane E. Remillard, Esq.

(57) ABSTRACT

Isolated human monoclonal antibodies which bind to CD30 (e.g., human CD30) are disclosed. The human antibodies can be produced in a non-human transgenic animal, e.g., a transgenic mouse, capable of producing multiple isotypes of human monoclonal antibodies by undergoing V-D-J recombination and isotype switching. Also disclosed are derivatives of the human antibodies (e.g., bispecific antibodies and immunoconjugates), pharmaceutical compositions comprising the human antibodies, non-human transgenic animals and hybridomas which produce the human antibodies, and therapeutic and diagnostic methods for using the human antibodies.

15 Claims, 16 Drawing Sheets

OTHER PUBLICATIONS

Engert, A., et al. "Evaluation of ricin A chain-containing immunotoxins directed against the CD30 antigen as potential reagents for the treatment of Hodgkin's disease" *Cancer Res.* Jan. 1, 1990;50(1):84-8.

Engert, A., et al. "Antitumor effects of ricin A chain immunotoxins prepared from intact antibodies and Fab' fragments on solid human Hodgkin's disease tumors in mice" *Cancer Res.* May 15, 1990;50(10):2929-35.

Falini, B., et al. "In vivo targeting of Hodgkin and Reed-Sternberg cells of Hodgkin's disease with monoclonal antibody Ber-H2 (CD30): immunohistological evidence" *Br J Haematol.* Sep. 1992;82(1):38-45.

Falini, B., et al. "Response of refractory Hodgkin's disease to monoclonal anti-CD30 immunotixin" *Lancet* May 16, 1992;339(8803):1195-6.

Froese, P., et al. "Biochemical characterization and biosynthesis of the Ki-1 antigen in Hodgkin-derived and virus-transformed human B and T lymphoid cell lines" *J Immunol.* Sep. 15, 1987;139(6):2081-7.

Gruss, H.J. et al. "Pleiotropic effects of the CD30 ligand on CD30-expressing cells and lymphoma cell lines" *Blood* Apr. 15, 1994;83(8):2045-56.

Hecht, T., et al. "Production and characterization of a monoclonal antibody that binds Reed-Sternberg cells" *J Immunol.* Jun. 1985;134(6):4231-6.

Horn-Lohrens, O., et al. "Shedding of the soluble form of CD30 from the Hodgkin-analogous cell line L540 is strongly inhibited by a new CD30-specific antibody (Ki-4)" *Int J Cancer.* Feb. 8, 1995;60(4):539-44.

Hsu, S.M., et al. "Effect of monoclonal antibodies anti-2H9, anti-IRac, and anti-HeFi-1 on the surface antigens of Reed-Sternberg cells" *J Natl Cancer Inst.* Nov. 1987;79(5):1091-9.

Hubinger, G., et al. "CD30-mediated cell cycle arrest associated with induced expression of p21(CIP1/WAF1) in the anaplastic large cell lymphoma cell line Karpas 299" *Oncogene.* Feb. 1, 2001;20(5):590-8.

Josimovic-Alasevic, O., et al. "Ki-1 (CD30) antigen is released by Ki-1 positive tumor cells in vitro and in vivo. I. Partial characterization of soluble Ki-1 antigen and detection of the antigen in cell culture supernatants and in serum by an enzyme-linked immunosorbent assay" *Eur J Immunol.* Jan. 1989;19(1):157-62.

May, R. D., et al. "Evaluation of ricin A chain-containing immunotoxins directed against different epitopes on the delat-chain of cell surface-associated IgD on murine B cells" *J Immunol.* May 1, 1990;144(9):3637-42.

Mechtersheimer, G., et al. "Expression of Ki-1 antigen (CD30) in mesenchymal tumors" *Cancer* Oct. 15, 1990;66(8):1732-7.

Miettinen, M., "CD30 distribution. Immunohistochemical study on formaldehyde-fixed, paraffin-embedded Hodgkin's and non-Hodgkin's lymphomas" *Arch Pathol Lab Med.* Nov. 1992;116(11):1197-201.

Pallesen, G., et al. "The diagnostic significance of the CD30 (Ki-1) antigen" *Histopathology* Apr. 1990;16(4):409-13.

Pallesen, G., et al. "Ki-1 (CD30) antigen is regularly expressed by tumor cells of embryonal carcinoma" *Am J Pathol.* Dec. 1988;133(3):446-50.

Piris, M., et al. "CD30 expression in non-Hodgkin's lymphoma" *Histopathology* Sep. 1990;17(3):211-8.

Pfreundschuh, M., et al. "Hodgkin and Reed-Sternberg cell associated monoclonal antibodies HRS-1 and HRS-2 react with activated cells of lymphoid and monocytoid origin" *Anticancer Res.* Mar.-Apr. 1988;8(2):217-24.

Pohl, C., et al. "CD30-specific AB1-AB2-AB3 internal image antibody network: potential use as anti-idiotype vaccine against Hodgkin's lymphoma" *Int. J. Cancer* May 28, 1993;54(3):418-25.

Press, O.W., et al. "Ricin A-chain containing immunotoxins directed against different epitopes on the CD2 molecule differ in their ability to kill normal and malignant T cells" *J. Immunol.* Dec. 15, 1988;141(12):4410-7.

Schwab, U., "Production of a monoclonal antibody specific for Hodgkin and Sternberg-Reed cells of Hodgkin's disease and a subset of normal lymphoid cells" *Nature* Sep. 2, 1982;299(5878):65-7.

Schwarting, R., et al. "BER-H2: a new anti-Ki-1 (CD30) monoclonal antibody directed at a formol-resistant epitope" *Blood* Oct. 1989;74(5):1678-89.

Stein, H., et al. "The expression of the Hodgkin's disease associated antigen Ki-1 in reactive and neoplastic lymphoid tissue: evidence that Reed-Sternberg cells and histiocytic malignancies are derived from activated lymphoid cells" *Blood* Oct. 1985;66(4):848-58.

Tian, Z. G., et al. "In vivo antitumor effects of unconjugated CD30 monoclonal antibodies on human anaplastic large-cell lymphoma xenografts" *Cancer Res.* Nov. 15, 1995;55(22):5335-41.

Tutt, A.L., et al. "Monoclonal antibody therapy of B cell lymphoma: signaling activity on tumor cells appears more important than recruitment of effectors" *J. Immunol.* Sep. 15, 1998;161(6):3176-85.

Tsutsumi, Y., et al. "Site-specific chemical modification with polyethylene glycol of recombinant immunotoxin anti-Tac(Fv)-PE38 (LMB-2) improves antitumor activity and reduces animal toxicity and immunogenicity" *PNAS* 2000 97 (15):8548-8553.

Wahl, A., et al. "The anti-CD30 monoclonal antibody SGN-30 promotes growth arrest and DNA fragmentation in vitro and affects antitumor activity in models of Hodgkin's disease" *Cancer Res.* Jul. 1, 2002;62(13):3736-42.

Borchmann, P., et al. "Phase 1 trial of the novel bispecific molecule H22xKi-4 in patients with refractory Hodgkin lymphoma" *Blood* Nov. 1, 2002;100(9):3101-7.

Koon, H., et al. "Anti-CD30 antibody-based therapy" *Curr. Opin. Oncol.* Nov. 2000;12(6):588-93.

Schnell, R., et al. "A Phase I study with an anti-CD30 ricin A-chain immunotoxin (Ki-4.dgA) in patients with refractory CD30+ Hodgkin's and non-Hodgkin's lymphoma" *Clin. Cancer Res.* Jun. 2002;8(6):1779-86.

Klimka, A., et al., "Human anti-CD30 recombinant antibodies by guided phage antibody selection using cell panning," *British Journal of Cancer*, vol. 83(2):252-260 (2000).

\* cited by examiner

Anti-CD30 17G1 VH

V-segment:    Locus: 3-07
    D segment: Not Found
    J segment: JH2

```
          E   V   Q   L   V   E   S   G   G   G   L   V   Q   P   G   G   S   L
  1      GAG GTG CAG TTG GTG GAG TCT GGG GGA GGC TTG GTC CAG CCT GGG GGG TCC CTG

CDR1
          R   L   S   C   V   A   S   G   F   T   F   S   N   S   W   M   S   W
 55      AGA CTC TCC TGT GTA GCC TCT GGA TTC ACC TTT AGT AAC TCT TGG ATG AGC TGG

CDR2
          V   R   Q   A   P   G   K   G   L   E   W   V   A   N   I   N   E   D
109      GTC CGC CAG GCT CCA GGG AAA GGG CTG GAG TGG GTG GCC AAC ATA AAC GAA GAT

CDR2
          G   S   E   K   F   Y   V   D   S   V   K   G   R   F   T   F   S   R
163      GGA AGT GAG AAA TTC TAT GTG GAC TCT GTG AAG GGC CGA TTC ACC TTC TCC AGA

D   N   A   E   N   S   L   Y   L   Q   M   N   S   L   R   A   E   D
217      GAC AAC GCC GAG AAC TCA CTG TAT CTG CAA ATG AAC AGC CTG AGA GCC GAG GAC

CDR3
          T   A   V   Y   Y   C   A   R   V   H   W   Y   F   H   L   W   G   R
271      ACG GCT GTG TAT TAC TGT GCG AGG GTT CAT TGG TAC TTC CAT CTC TGG GGC CGT

G   T   L   V   T   V   S   S
325      GGC ACC CTG GTC ACT GTC TCC TCA
```

*Fig. 7*

Anti-CD30 17G1 VL

V-segment:    Locus: A27
J segment: JK1

```
          E   I   V   L   T   Q   S   P   G   T   L   S   L   S   P   G   E   R
  1      GAA ATT GTG TTG ACG CAG TCT CCA GGC ACC CTG TCT TTG TCT CCA GGG GAA AGA

CDR1
                                  ~~~~~~~~~~~~~~~~~~~~~~~~~~~~~~~~~~~~~~~~~~~~
          A   T   L   S   C   R   A   S   Q   S   V   S   S   S   Y   L   A   W
 55      GCC ACC CTC TCC TGC AGG GCC AGT CAG AGT GTT AGC AGC AGC TAC TTA GCC TGG

CDR2
                                                                ~~~~~~~~~~~~
          Y   Q   Q   K   P   G   Q   A   P   R   L   L   I   Y   G   A   S   S
109      TAC CAG CAG AAA CCT GGC CAG GCT CCC AGG CTC CTC ATC TAT GGT GCA TCC AGC

CDR2
         ~~~~~~~~~~
          R   A   T   G   I   P   D   R   F   S   G   S   G   S   G   T   D   F
163      AGG GCC ACT GGC ATC CCA GAC AGG TTC AGT GGC AGT GGG TCT GGG ACA GAC TTC

CDR3
                                                                        ~~~~
          T   L   T   I   S   S   L   E   P   E   D   F   A   V   Y   Y   C   Q
217      ACT CTC ACC ATC AGC AGC CTG GAG CCT GAA GAT TTT GCA GTG TAT TAC TGT CAG

CDR3
         ~~~~~~~~~~~~~~~~~~~~~~~
          Q   Y   G   S   S   P   W   T   F   G   Q   G   T   K   V   E   I   K
271      CAG TAT GGT AGC TCA CCG TGG ACG TTC GGC CAA GGG ACC AAG GTG GAA ATC AAA
```

*Fig. 8*

Anti-2H9 CD30 VH

V-segment:     Locus: 4-34
    D segment: Locus - 5-12
    J segment: JH2

```
          Q   V   Q   L   Q   Q   W   G   A   G   L   L   K   P   S   E   T   L
  1       CAG GTG CAG CTA CAG CAG TGG GGC GCA GGA CTG TTG AAG CCT TCG GAG ACC CTG

CDR1
                                                          ~~~~~~~~~~~~~~~~~~~~
          S   L   T   C   A   V   Y   G   G   S   F   S   G   Y   Y   W   S   W
 55       TCC CTC ACC TGC GCT GTC TAT GGT GGG TCC TTC AGT GGT TAC TAC TGG AGC TGG

CDR2
                                                      ~~~~~~~~~~~~~~~~~~~~
          I   R   Q   P   P   G   K   G   L   E   W   I   G   E   I   N   H   S
109       ATC CGC CAG CCC CCA GGG AAG GGG CTG GAG TGG ATT GGG GAA ATC AAT CAT AGT

CDR2
              ~~~~~~~~~~~~~~~~~~
          G   S   T   K   Y   T   P   S   L   K   S   R   V   T   I   S   V   D
163       GGA AGC ACC AAG TAC ACC CCG TCC CTC AAG AGC CGA GTC ACC ATA TCA GTA GAC

T   S   K   H   Q   F   S   L   K   L   S   S   V   T   A   A   D   T
217       ACG TCC AAG CAC CAA TTC TCC CTG AAG CTG AGC TCT GTG ACC GCC GCG GAC ACG

CDR3
                                      ~~~~~~~~~~~~~~~~~~~~~~~~~~~~~~
          A   V   Y   Y   C   A   R   E   T   V   Y   Y   F   D   L   W   G   R
271       GCT GTG TAT TAC TGT GCG AGA GAG ACT GTC TAC TAC TTC GAT CTC TGG GGC CGT

G   T   L   V   T   V   S   S
325       GGC ACC CTG GTC ACT GTC TCC TCA
```

*Fig. 9*

Anti-2H9 CD30 VL

V-segment: Locus: L6
J segment: JK1

```
         E   I   V   L   T   Q   S   P   A   T   L   S   L   S   P   G   E   R
  1      GAA ATT GTG TTG ACA CAG TCT CCA GCC ACC CTG TCT TTG TCT CCA GGG GAA AGA
```

CDR1
                  ~~~~~~~~~~~~~~~~~~~~~~~~~~~~~~~~~~~~~~~~~~~~~~~~~~~~~~~

```
         A   T   L   S   C   R   A   S   Q   S   V   S   S   N   L   A   W   Y
  55     GCC ACC CTC TCC TGC AGG GCC AGT CAG AGT GTA AGC AGC AAC TTA GCC TGG TAC
```

CDR2
                                                  ~~~~~~~~~~~~~~~~~~~~~~~~~

```
         Q   Q   K   P   G   Q   A   P   R   L   L   I   Y   D   A   S   N   R
  109    CAA CAG AAA CCT GGC CAG GCT CCC AGG CTC CTC ATC TAT GAT GCA TCC AAC AGG
```

CDR2
~~~~~~

```
         A   T   G   I   P   A   R   L   S   G   S   G   S   G   T   D   F   T
  163    GCC ACT GGC ATC CCA GCC AGG CTC AGT GGC AGT GGG TCT GGG ACA GAC TTC ACT
```

CDR3
                                                                  ~~~~~~

```
         L   T   I   S   S   L   E   P   E   D   F   A   V   Y   Y   C   Q   Q
  217    CTC ACC ATC AGC AGC CTA GAG CCT GAA GAT TTT GCA GTT TAT TAC TGT CAA CAG
```

CDR3
         ~~~~~~~~~~~~~~~~~~~~~~~~~~

```
         R   S   N   W   P   W   T   F   G   Q   G   T   K   V   E   I   K
  271    CGT AGC AAC TGG CCG TGG ACG TTC GGC CAA GGG ACC AAG GTG GAA ATC AAA
```

*Fig. 10*

Anti-CD30 5F11 VH

V-segment:      Locus: 4-34
    D segment: Locus - 7-27
    J segment: JH4b

```
         Q   V   Q   L   Q   Q   W   G   A   G   L   L   K   P   S   E   T   L
  1     CAG GTG CAG CTA CAG CAG TGG GGC GCA GGA CTG TTG AAG CCT TCG GAG ACC CTG

CDR1
                                                         ~~~~~~~~~~~~~~~~~~
         S   L   T   C   A   V   Y   G   G   S   F   S   A   Y   Y   W   S   W
 55     TCC CTC ACC TGC GCT GTC TAT GGT GGG TCC TTC AGT GCT TAC TAC TGG AGC TGG

CDR2
                                                         ~~~~~~~~~~~~~~
         I   R   Q   P   P   G   K   G   L   E   W   I   G   D   I   N   H   G
109     ATC CGC CAG CCC CCA GGG AAG GGG CTG GAG TGG ATT GGG GAC ATC AAT CAT GGT

CDR2
        ~~~~~~~~~~~~~~~~~~~~~~~~~~~~~~~~~~~~
         G   G   T   N   Y   N   P   S   L   K   S   R   V   T   I   S   V   D
163     GGA GGC ACC AAC TAC AAC CCG TCC CTC AAG AGT CGA GTC ACC ATA TCA GTA GAC

T   S   K   N   Q   F   S   L   K   L   N   S   V   T   A   A   D   T
217     ACG TCC AAG AAC CAG TTC TCC CTG AAG CTG AAC TCT GTA ACC GCC GCG GAC ACG

CDR3
                                    ~~~~~~~~~~~~~~~~
         A   V   Y   Y   C   A   S   L   T   A   Y   W   G   Q   G   S   L   V
271     GCT GTG TAT TAC TGT GCG AGC CTA ACT GCC TAC TGG GGC CAG GGA AGC CTG GTC

T   V   S   S
325     ACC GTC TCC TCA
```

*Fig. 11*

Anti-CD30 5F11 VL

V-segment:     Locus: L15
J segment: JK5

```
       D   I   Q   M   T   Q   S   P   T   S   L   S   A   S   V   G   D   R
  1    GAC ATC CAG ATG ACC CAG TCT CCA ACC TCA CTG TCT GCA TCT GTA GGA GAC AGA

CDR1
                                 ~~~~~~~~~~~~~~~~~~~~~~~~~~~~~~~~~~~~~~~~~~~~
       V   T   I   T   C   R   A   S   Q   G   I   S   S   W   L   T   W   Y
 55    GTC ACC ATC ACT TGT CGG GCG AGT CAG GGT ATT AGC AGC TGG TTA ACC TGG TAT

CDR2
                                                                 ~~~~~~~~~~~~
       Q   Q   K   P   E   K   A   P   K   S   L   I   Y   A   A   S   S   L
109    CAG CAG AAA CCA GAG AAA GCC CCT AAG TCC CTG ATC TAT GCT GCA TCC AGT TTG

CDR2
       ~~~~
       Q   S   G   V   P   S   R   F   S   G   S   G   S   G   T   D   F   T
163    CAA AGT GGG GTC CCA TCA AGG TTC AGC GGC AGT GGA TCT GGG ACA GAT TTC ACT

CDR3
                                                                        ~~~~
       L   T   I   S   S   L   Q   P   E   D   F   A   T   Y   Y   C   Q   Q
217    CTC ACC ATC AGC AGC CTG CAG CCT GAA GAT TTT GCA ACT TAT TAC TGC CAA CAG

CDR3
       ~~~~~~~~~~~~~~~~
       Y   D   S   Y   P   I   T   F   G   Q   G   T   R   L   E   I   K
271    TAT GAT AGT TAC CCT ATC ACC TTC GGC CAA GGG ACA CGA CTG GAG ATT AAA
```

*Fig. 12*

ANTI-CD30 GERMLINE SEQUENCES

VH4-34 (5F11 & 2H9 VH)
CAG GTG CAG CTA CAG CAG TGG GGC GCA GGA CTG TTG AAG CCT TCG GAG ACC
CTG TCC CTC ACC TGC GCT GTC TAT GGT GGG TCC TTC AGT GGT TAC TAC TGG
AGC TGG ATC CGC CAG CCC CCA GGG AAG GGG CTG GAG TGG ATT GGG GAA ATC
AAT CAT AGT GGA AGC ACC AAC TAC AAC CCG TCC CTC AAG AGT CGA GTC ACC
ATA TCA GTA GAC ACG TCC AAG AAC CAG TTC TCC CTG AAG CTG AGC TCT GTG
ACC GCC GCG GAC ACG GCT GTG TAT TAC TGT GCG AGA

L15 (5F11 VL)
GAC ATC CAG ATG ACC CAG TCT CCA TCC TCA CTG TCT GCA TCT GTA GGA GAC
AGA GTC ACC ATC ACT TGT CGG GCG AGT CAG GGT ATT AGC AGC TGG TTA GCC
TGG TAT CAG CAG AAA CCA GAG AAA GCC CCT AAG TCC CTG ATC TAT GCT GCA
TCC AGT TTG CAA AGT GGG GTC CCA TCA AGG TTC AGC GGC AGT GGA TCT GGG
ACA GAT TTC ACT CTC ACC ATC AGC AGC CTG CAG CCT GAA GAT TTT GCA ACT
TAT TAC TGC CAA CAG TAT AAT AGT TAC CCT

VH3-11 (17G1 VH)
GAG GTG CAG CTG GTG GAG TCT GGG GGA GGC TTG GTC CAG CCT GGG GGG TCC
CTG AGA CTC TCC TGT GCA GCC TCT GGA TTC ACC TTT AGT AGC TAT TGG ATG
AGC TGG GTC CGC CAG GCT CCA GGG AAA GGG CTG GAG TGG GTG GCC AAC ATA
AAG CAA GAT GGA AGT GAG AAA TAC TAT GTG GAC TCT GTG AAG GGC CGA TTC
ACC ATC TCC AGA GAC AAC GCC AAG AAC TCA CTG TAT CTG CAA ATG AAC AGC
CTG AGA GCC GAG GAC ACG GCT GTG TAT TAC TGT GCG AGA

A27 (17G1 VL)
GAA ATT GTG TTG ACG CAG TCT CCA GGC ACC CTG TCT TTG TCT CCA GGG GAA
AGA GCC ACC CTC TCC TGC AGG GCC AGT CAG AGT GTT AGC AGC AGC TAC TTA
GCC TGG TAC CAG CAG AAA CCT GGC CAG GCT CCC AGG CTC CTC ATC TAT GGT
GCA TCC AGC AGG GCC ACT GGC ATC CCA GAC AGG TTC AGT GGC AGT GGG TCT
GGG ACA GAC TTC ACT CTC ACC ATC AGC AGA CTG GAG CCT GAA GAT TTT GCA
GTG TAT TAC TGT CAG CAG TAT GGT AGC TCA CCT

L6 (2H9 VL)
GAA ATT GTG TTG ACA CAG TCT CCA GCC ACC CTG TCT TTG TCT CCA GGG GAA
AGA GCC ACC CTC TCC TGC AGG GCC AGT CAG AGT GTT AGC AGC TAC TTA GCC
TGG TAC CAA CAG AAA CCT GGC CAG GCT CCC AGG CTC CTC ATC TAT GAT GCA
TCC AAC AGG GCC ACT GGC ATC CCA GCC AGG TTC AGT GGC AGT GGG TCT GGG
ACA GAC TTC ACT CTC ACC ATC AGC AGC CTA GAG CCT GAA GAT TTT GCA GTT
TAT TAC TGT CAG CAG CGT AGC AAC TGG CCT

*Fig. 13*

HUMAN MONOCLONAL ANTIBODIES AGAINST CD30

RELATED APPLICATIONS

This application claims priority to U.S. Ser. No. 60/347,649, filed on Jan. 9, 2002, U.S. Ser. No. 60/404,427 filed on Aug. 19, 2002, and U.S. Ser. No. 60/431,684 filed on Dec. 6, 2002, the contents of which are incorporated herein by reference.

BACKGROUND OF THE INVENTION

The CD30 cell surface molecule is a member of the tumor necrosis factor receptor (TNF-R) superfamily. This family of molecules has variable homology among its members and includes nerve growth factor receptor (NGFR), CD120(a), CD120(b), CD27, CD40 and CD95. These molecules are typically characterized by the presence of multiple cysteine-rich repeats in the extracytoplasmic region (de Bruin, P. C., et al. *Leukemia* 9:1620-1627 (1995)). Members of this family are considered crucial for regulating proliferation and differentiation of lymphocytes.

CD30 is a type I transmembrane glycoprotein with six (human) or three (murine and rat) cysteine-rich repeats with a central hinge sequence. CD30 exists as a 120 kDa membrane molecule which develops from an intercellular precursor protein of 90 kDa. It is shed from the cell surface as a soluble protein (sCD30) of approximately 90 kDa. Shedding of sCD30 occurs as an active process of viable CD30 cells and is not merely caused by the release from dying or dead cells. cDNAs encoding the CD30 protein have been cloned from expression libraries of the HLTV-1 human T-cell line HUT-102 by immunoscreening with monoclonal antibodies Ki-1 and Ber-H2 (Schwab, U., et al. *Nature* 299:65 (1982)). The mouse and rat CD30 cDNA has been found to encode 498 and 493 amino acids, respectively. Human CD30 cDNA encodes an additional 90 amino acids, partially duplicated from one of the cysteine rich domains. The CD30 gene has been mapped to 1p36 in humans and 5q36.2 in rats.

CD30 is preferentially expressed by activated lymphoid cells. Specifically, stimulation of CD30 in lymphoid cells has been shown to induce pleiotropic biological effects, including proliferation, activation, differentiation and cell death, depending on cell type, stage of differentiation and presence of other stimuli (Gruss, H. J. et al., *Blood* 83:2045-2056 (1994)). CD30 was originally identified by the monoclonal antibody Ki-1, which is reactive with antigens expressed on Hodgkin and Reed-Sternberg cells of Hodgkin's disease (Schwab et al., *Nature* 299:65 (1982)). Accordingly, CD30 is widely used as a clinical marker for Hodgkin's lymphoma and related hematological malignancies (Froese et al., *J. Immunol.* 139:2081 (1987); Carde et al., *Eur. J. Cancer* 26:474 (1990)).

CD30 was subsequently shown to be expressed on a subset of non-Hodgkin's lymphomas (NHL), including Burkitt's lymphoma, anaplastic large-cell lymphomas (ALCL), cutaneous T-cell lymphomas, nodular small cleaved-cell lymphomas, lymphocytic lymphomas, peripheral T-cell lymphomas, Lennert's lymphomas, immunoblastic lymphomas, T-cell leukemia/lymphomas (ATLL), adult T-cell leukemia (T-ALL), and entroblastic/centrocytic (cb/cc) follicular lymphomas (Stein et al., *Blood* 66:848 (1985); Miettinen, *Arch. Pathol. Lab. Med.* 116:1197 (1992); Piris et al., *Histopathology* 17:211 (1990); Bums et al., *Am. J. Clin. Pathol.* 93:327(1990); and Eckert et al., *Am. J. Dermatopathol.* 11:345 (1989)), as well as several virally-transformed lines such as human T-Cell Lymphotrophic Virus I or II transformed T-cells, and Epstein-Barr Virus transformed B-cells (Stein et al., *Blood* 66:848 (1985); Andreesen et al., *Blood* 63:1299 (1984)). In addition, CD30 expression has been documented in embryonal carcinomas, nonembryonal carcinomas, malignant melanomas, mesenchymal tumors, and myeloid cell lines and macrophages at late stages of differentiation (Schwarting et al., Blood 74:1678 (1989); Pallesen et al., Am J. Pathol. 133:446 (1988); Mechtersheimer et al., Cancer 66:1732 (1990); Andreesen et al., Am. J. Pathol. 134:187 (1989)).

Since the percentage of CD30-positive cells in normal individuals is quite small, the expression of CD30 in tumor cells renders it an important target for antibody mediated therapy to specifically target therapeutic agents against CD30-positive neoplastic cells (Chaiarle, R., et al. *Clin. Immunol.* 90(2):157-164 (1999)). However, while the results obtained to date clearly establish CD30 as a useful target for immunotherapy, they also show that currently available murine antibodies do not constitute ideal therapeutic agents.

Accordingly, the need exists for improved therapeutic antibodies against CD30 which are effective at treating and/or preventing diseases mediated by CD30.

SUMMARY OF THE INVENTION

The present invention provides isolated human monoclonal antibodies which bind to human CD30, as well as derivatives (e.g., immunoconjugates and bispecific molecules) and other therapeutic compositions containing such antibodies, alone or in combination with additional therapeutic agents. Also provided are methods for treating a variety CD30 mediated diseases using the antibodies and compositions of the invention.

The human antibodies of the present invention bind to CD30 and inhibit CD30 function (and CD30 mediated effects) and/or inhibit the growth (e.g., mediate killing) of cells expressing CD30, such as tumor cells and cells involved in immune diseases. Such cells include, for example, bone marrow cells, liver cells, lymph node cells, skin cells, spleen cells, thymus cells, tonsil cells, decidua cells, endometrial cells, Hodgkin's cells, Reed-Sternberg cells, anaplastic large cell lymphoma (ALCL) cells, pleomorphic and immunoblastic lymphoma cells, T cells, B cells, NK cells and monocytes. In a particular embodiment, the human antibodies are used to inhibit growth/mediate killing of Hodgkin's cells in the treatment of lymphoma.

In one embodiment of the invention, the human antibodies inhibit growth/mediate killing of tumor cells by inducing antibody dependent cellular cytotoxicity (ADCC) in the presence of human effector cells (e.g., monocytes or mononuclear cells). In another embodiment, the human antibodies induce phagocytosis of tumor cells expressing CD30 in the presence of macrophages. Accordingly, the antibodies of the present invention provide an improved means for treating and preventing disorders mediated by CD30 activity attributable in part to their unique specificity (e.g., epitope specificity and lack of cross-reactivity with related cell surface antigens), affinity, structure, functional activity and the fact that they are fully human, making them significantly less immunogenic and more therapeutically effective and useful when administered to human patients than other CD30 antibodies previously generated (e.g., murine and humanized antibodies).

Isolated human antibodies of the invention include a variety of antibody isotypes, such as IgG1, IgG2, IgG3, IgG4, IgM, IgA1, IgA2, IgAsec, IgD, and IgE. Typically, they include IgG1 (e.g., IgG1), IgG3 and IgM isotypes. The antibodies can be full-length (e.g., an IgG1 or IgG3 antibody) or can include only an antigen-binding portion (e.g., a Fab, F(ab')$_2$, Fv or a single chain Fv fragment).

A particular therapeutic antibody of the present invention includes human monoclonal antibody (HuMab) 17G1 and functionally equivalent antibodies which (a) are encoded by human heavy chain and human light chain nucleic acids comprising nucleotide sequences in their variable regions as set forth in SEQ ID NO:1 and SEQ ID NO:3, respectively, and conservative sequence modifications thereof, or (b) include heavy chain and light chain variable regions which comprise the amino acid sequences shown in SEQ ID NO:2 and SEQ ID NO:4, respectively, and conservative sequence modifications thereof.

Another particular therapeutic antibody of the present invention includes human monoclonal antibody 2H9 and functionally equivalent antibodies which (a) are encoded by human heavy chain and human light chain nucleic acids comprising nucleotide sequences in their variable regions as set forth in SEQ ID NO:5 and SEQ ID NO:7, respectively, and conservative sequence modifications thereof, or (b) include heavy chain and light chain variable regions.which comprise the amino acid sequences shown in SEQ ID NO:6 and SEQ ID NO:8, respectively, and conservative sequence modifications thereof.

Yet another particular therapeutic antibody of the present invention includes human monoclonal antibody 5F11 and functionally equivalent antibodies which (a) are encoded by human heavy chain and human light chain nucleic acids comprising nucleotide sequences in their variable regions as set forth in SEQ ID NO:9 and SEQ ID NO:11, respectively, and conservative sequence modifications thereof, or (b) include heavy chain and light chain variable regions which comprise the amino acid sequences shown in SEQ ID NO:10 and SEQ ID NO:12, respectively, and conservative sequence modifications thereof.

Also included within the present invention are antibodies which bind to an epitope on human CD30 defined by antibody 17G1, 2H9 or 5F11, and/or which compete for binding to CD30 with antibody 17G1, 2H9 or 5F11, or which have other functional binding characteristics exhibited by antibody 17G1, 2H9 or 5F11. Such antibodies include those which bind to CD30 with a dissociation equilibrium constant (Kd) of approximately $10^{-11}$ M, and/or with an association equilibrium constant (Ka) of at least about $10^7$ $M^{-11}$. Such antibodies also include those which do not cross-react with related cell-surface antigens and thus do not inhibit their function.

Still other particular human antibodies of the invention include those which comprise a CDR domain having a human heavy and light chain CDR1 region, a human heavy and light chain CDR2 region, and a human heavy and light chain CDR3 region, wherein (a) the CDR1, CDR2, and CDR3 of the human heavy chain regions comprise an amino acid sequence selected from the group consisting of the amino acid sequences of the CDR1, CDR2, and CDR3 regions shown in FIG. 7 (SEQ ID NOs:16, 17 and 18, respectively), FIG. 9 (SEQ ID NOs:28, 29 and 30, respectively), and FIG. 11 (SEQ ID NOs:40, 41 and 42, respectively) and conservative sequence modifications thereof, and (b) the CDR1, CDR2, and CDR3 of the human light chain regions comprise an amino acid sequence selected from the group consisting of the amino acid sequences of the CDR1, CDR2, and CDR3 regions shown in FIG. 8 (SEQ ID NOs:22, 23 and 24, respectively), FIG. 10 (SEQ ID NOs:34, 35 and 36, respectively), and FIG. 12 (SEQ ID NOs:46, 47 and 48, respectively) and conservative sequence modifications thereof.

Alternatively, particular human antibodies of the invention include those which comprise a CDR domain having a human heavy and light chain CDR1 region, a human heavy and light chain CDR2 region, and a human heavy and light chain CDR3 region which comprise an amino acid sequence at least 80% homologous, preferably 85% homologous, more preferably 90%, 95%, 98%, and 99% homologous to the amino acid sequence of the CDR1, CDR2, and CDR3 regions shown in FIGS. 7-12 (SEQ ID NOs: 16, 17, 18, 22, 23, 24, 28, 29, 30, 34, 35, 36, 40, 41, 42, 46, 47 and 48).

In another embodiment, a human antibody of the present invention binds to CD30 and inhibits CD30 function (e.g., CD30 mediated effects) by partially or completely blocking CD30 ligand binding to CD30. Examples of CD30 ligands include CD153, TRAF1, TRAF2, TRAF3 and TRAF5

In still another embodiment, the human antibodies of the present invention can be characterized by one or more of the following properties:

a) specificity for the CD30;

b) a binding affinity to CD30 with an affinity constant of at least about $10^7$ $M^{-1}$, preferably about $10^8$ $M^1$, and more preferably, about $10^9$ $M^{-1}$ to $10^{10}$ $M^{-1}$ or higher;

c) an association constant ($K_{assoc}$) with CD30 of at least about $10^3$, more preferably about $10^4$ and most preferably about $10^5$ $M^{-1}S^{-1}$;

d) a dissociation constant ($K_{dis}$) from CD30 of about $10^{-3}$ $s^{-1}$, preferably about $10^{-4}$ $s^{-1}$, more preferably, $10^{-5}$ $s^{-1}$, and most preferably, $10^{-6}$ $s^{-1}$;

e) the ability to opsonize a cell expressing CD30; or f) the ability to inhibit growth and/or mediate phagocytosis and killing of cells expressing CD30 (e.g., a tumor cell) in the presence of human effector cells at a concentration of about 10 µg/ml or less (e.g., in vitro).

Human anti-CD30 antibodies of the invention can be produced recombinantly in a host cell (e.g., a CHO cell or a lymphocytic cell) or be obtained directly from a hybridoma which expresses the antibody (i.e., which includes a B cell obtained from a transgenic non-human animal, e.g., a transgenic mouse, having a genome comprising a human heavy chain transgene and a human light chain transgene that encode the antibody, fused to an immortalized cell). In a particular embodiment, the antibodies are produced by a hybridoma referred to herein as 17G1 (SEQ ID NOs:1-4), 2H9 (SEQ ID NOs:5-8) and 5F11 (SEQ ID NOs:9-12).

In yet another aspect, the invention provides a transgenic non-human animal, such as a transgenic mouse (also referred to herein as a "HuMAb mouse"), which expresses human monoclonal antibodies that bind to CD30. In a particular embodiment, the transgenic non-human animal is a transgenic mouse having a genome comprising a human heavy chain transgene and a human light chain transgene encoding all or a portion of an antibody of the invention. The transgenic non-human animal can be immunized with a purified or enriched preparation of CD30 antigen and/or cells expressing CD30. Preferably, the transgenic non-human animal, e.g., the transgenic mouse, is capable of producing multiple isotypes of human monoclonal antibodies to CD30 (e.g., IgG, IgA and/or IgM) by undergoing V-D-J recombination and isotype switching. Isotype switching may occur by, e.g., classical or non-classical isotype switching.

Accordingly, in yet another aspect, the invention provides isolated B-cells from a transgenic non-human animal as described above, e.g., a transgenic mouse, which expresses human anti-CD30 antibodies. The isolated B-cells can then be immortalized by fusion to an immortalized cell to provide a source (e.g., a hybridoma) of human anti-CD30 antibodies. Such hybridomas (i.e., which produce human antiCD30 antibodies) are also included within the scope of the invention.

As exemplified herein, human antibodies of the invention can be obtained directly from hybridomas which express the antibody, or can be cloned and recombinantly expressed in a host cell (e.g., a CHO cell or a lymphocytic cell). Accordingly, in another aspect, the present invention provides methods for producing human monoclonal antibodies which bind to human CD30. In one embodiment, the method includes immunizing a transgenic non-human animal, e.g., a transgenic mouse, as previously described (e.g., having a genome comprising a human heavy chain transgene and a human light chain transgene encoding all or a portion of an anti-CD30 antibody), with a purified or enriched preparation of human CD30 antigen and/or cells expressing human CD30. B cells (e.g., splenic B cells) of the animal are then obtained and fused with myeloma cells to form immortal, hybridoma cells that secrete human monoclonal antibodies against CD30.

In yet another aspect, human anti-CD30 antibodies of the invention are derivatized, linked to or co-expressed with another functional molecule, e.g., another peptide or protein (e.g., a Fab' fragment). For example, an antibody or antigen-binding portion of the invention can be functionally linked (e.g., by chemical coupling, genetic fusion, noncovalent association or otherwise) to one or more other molecular entities, such as another antibody (e.g., to produce a bispecific or a multispecific antibody), a cytotoxin, cellular ligand or antigen (e.g., to produce an immunoconjugate, such as an immunotoxin). Accordingly, the present invention encompasses a large variety of antibody conjugates, bispecific and multispecific molecules, and fusion proteins, all of which bind to CD30 expressing cells and which can be used to target other molecules to such cells.

In a particular embodiment, the invention provides a bispecific or multispecific molecule comprising at least one first binding specificity for CD30 (e.g., a human anti-CD30 antibody or fragment or mimetic thereof), and a second binding specificity for a human effector cell, such as a binding specificity for an Fc receptor (e.g., a human Fcγ receptor, such as FcγRI, or a human Fcα receptor). Typically, bispecific and multi specific molecules of the invention comprise at least one antibody, or fragment thereof (e.g., a Fab, Fab', F(ab')$_2$, Fv, or a single chain Fv), preferably a human antibody or a portion thereof, or a "chimeric" or a "humanized" antibody or a portion thereof (e.g., has a variable region or complementarity determining region (CDR) derived from a non-human antibody (e.g., murine) with the remaining portion(s) being human in origin).

Accordingly, the present invention includes bispecific and multispecific molecules that bind to both human CD30 and to an Fc receptor, e.g., a human IgG receptor, e.g., an Fc-gamma receptor (FcγR), such as FcγRI (CD64), FcγRII (CD32), and FcγRIII (CD16). Other Fc receptors, such as human IgA receptors (e.g. FcαRI), also can be targeted. The Fc receptor is preferably located on the surface of an effector cell, e.g., a monocyte, macrophage or an activated mononuclear cell. In a preferred embodiment, the bispecific and multispecific molecules bind to an Fc receptor at a site which is distinct from the immunoglobulin Fc (e.g., IgG or IgA) binding site of the receptor. Therefore, the binding of the bispecific and multispecific molecules is not blocked by physiological levels of immunoglobulins.

In yet another aspect, the present invention provides methods for inhibiting growth of cells expressing CD30 by contacting the cells with an effective amount of an antibody, antibody derivative or other therapeutic composition of the invention, such that the growth of the cell is inhibited. In one embodiment, the method includes killing of the cell expressing CD30 in the presence of effector cells, for example, by ADCC. In yet another embodiment, the method includes killing of the cell expressing CD30 by phagocytosis. The cells are preferably killed or inhibited without killing or inhibiting the activity of cells which do not express CD30 but which may, for example, express a structurally related cell-surface antigen (i.e., without cross-reactivity to related but functionally distinct cell surface antigens). Cells expressing CD30 which can be inhibited or killed using the human antibodies of the invention include, for example, tumor cells, bone marrow cells, liver cells, lymph node cells, skin cells, spleen cells, thymus cells, tonsil cells, decidua cells, endometrial cells, Hodgkin cells, Reed-Sternberg cells, anaplastic large cell lymphoma (ALCL) cells, pleomorphic and immunoblastic lymphoma cells, T cells, B cells, NK cells and monocytes.

Accordingly, human antibodies of the present invention can be used to treat and/or prevent a variety of CD30 mediated diseases by administering the antibodies to patients suffering from such diseases. Exemplary diseases that can be treated (e.g., ameliorated) or prevented include, but are not limited to, tumorigenic diseases and autoimmune diseases. Examples of tumorigenic diseases which can be treated and/or prevented include Hodgkin's disease, anaplastic large cell lymphoma (ALCL), adult T-cell lymphoma. (ATL), angioimmunoblastic lymphadenopathy (AILD)-like T cell lymphoma, HIV associated body cavity based lymphomas, Embryonal Carcinomas, undifferentiated carcinomas of the rhino-pharynx (e.g., Schmincke's tumor), Castleman's disease, Kaposi's Sarcoma and other T-cell or B-cell lymphomas. Examples of autoimmune diseases which can be treated and/or prevented include Rheumatoid arthritis, Systemic Lupus Erythematosus, Systemic Sclerosis, Atopic Dermatitis, Graves' disease, Hashimoto's thyroiditis, Wegner's granulomatosis, Omen's syndrome, chronic renal failure, acute infectious mononucleosis, HIV and herpes virus associated diseases.

In a particular embodiment of the invention, the subject being administered the antibody is additionally treated with a chemotherapeutic agent, radiation, or an agent that modulates, e.g., enhances or inhibits, the expression or activity of an Fc receptor, e.g., an Fcα receptor or an Fcγ receptor, such as a cytokine. Typical cytokines for administration during treatment include granulocyte colony-stimulating factor (G-CSF), granulocyte- macrophage colony-stimulating factor (GM-CSF), interferon-γ (IFN-γ), and tumor necrosis factor (TNF). Typical therapeutic agents include, among others, anti-neoplastic agents such as doxorubicin (adriamycin), cisplatin bleomycin sulfate, carmustine, chlorambucil, and cyclophosphamide hydroxyurea.

To increase the therapeutic efficacy of human anti-CD30 antibodies of the invention against cancer cells which do not highly express CD30, the antibodies can be co-administered with an agent which upregulates or otherwise effects expression of CD30, such as a lymphokine preparation which causes upregulated and more homogeneous expression of CD30 on tumor cells. Lymphokine preparations suitable for administration include interferon-gamma, tumor necrosis factor, and combinations thereof. These can be administered intravenously. Suitable dosages of lymphokine typically range from 10,000 to 1,000,000 units/patient.

In yet another aspect, the present invention provides a method for detecting in vitro or in vivo the presence of CD30 in a sample, e.g., for diagnosing a CD30-related disease. In one embodiment, this is achieved by contacting a sample to be tested, optionally along with a control sample, with a human monoclonal antibody of the invention (or an antigen-binding portion thereof) under conditions that allow for formation of a complex between the antibody and CD30. Complex formation is then detected (e.g., using an ELISA). When using a control sample along with the test sample, complex is detected in both samples and any statistically significant difference in the formation of complexes between the samples is indicative the presence of CD30 in the test sample.

In yet another aspect, the invention provides nucleic acid molecules encoding human anti-CD30 antibodies and portions thereof (e.g., variable regions thereof), as well as recombinant expression vectors which include the nucleic acids of the invention, and host cells transfected with such vectors. Methods of producing the antibodies by culturing these host cells are also encompassed by the invention. Particular nucleic acids provided by the invention comprise the nucleotide sequences shown in SEQ ID NO:1 and SEQ ID NO:3, encoding to the heavy and light chains respectively of human anti-CD30 antibody (HuMab) 17G1, the nucleotide sequences shown in SEQ ID NO:5 and SEQ ID NO:7, encoding to the heavy and light chains respectively of human anti-CD30 antibody (HuMab) 2H9 and the nucleotide sequences shown in SEQ ID NO:9 and SEQ ID NO:11, encoding to the heavy and light chains respectively of human anti-CD30 antibody (HuMab) SF11.

In another aspect, the present invention provides therapeutic and diagnostic compositions comprising one or more (i.e., a combination of) human anti-CD30 antibodies together with a carrier. In a particular embodiment, the composition further includes one or more other therapeutic agents, such as cytotoxic or radiotoxic agents, or agents which upregulate CD30 expression or expression of molecules expressed on effector cells, such as GM-CSF which upregulates expression of Fc receptors.

For use in in vivo treatment and prevention of CD30 mediated diseases, human antibodies of the present invention are administered to patients (e.g., human subjects) at therapeutically effective dosages using any suitable route of administration, such as injection and other routes of administration known in the art for antibody-based clinical products.

In another aspect, the present invention provides an immunoconjugate, e.g., an immunotoxin, which includes a fully human anti-CD30 antibody of the invention conjugated to a therapeutic agent, such as a cytotoxic agent, a radiotoxic agent, a chemotherapeutic drug, an immunosuppressive agent, or an anti-inflammatory agent, for example, a steroidal and nonsteroidal anti-inflammatory agent.

Alternatively, human antibodies of the invention can be co-administered with such therapeutic and cytotoxic agents, but not linked to them. They can be coadministered simultaneously with such agents (e.g., in a single composition or separately) or can be administered before or after administration of such agents. As described above, such agents can include cytotoxic agents, radiotoxic agents or chemotherapeutic agents, such as doxorubicin (adriamycin), cisplatin bleomycin sulfate, carmustine, chlorambucil, cyclophosphamide hydroxyurea and combinations thereof.

Other features and advantages of the instant invention be apparent from the following detailed description and examples which should not be construed as limiting. The contents of all references, patents and published patent applications cited throughout this application are expressly incorporated herein by reference

BRIEF DESCRIPTION OF THE DRAWINGS

FIG. 7 shows the nucleotide sequence (SEQ ID NO: 1) and corresponding amino acid sequence (SEQ ID NO: 2) of the $V_H$-region from HuMab 17G1. CDR regions are indicated.

FIG. 8 shows the nucleotide sequence (SEQ ID NO: 3) and corresponding amino acid sequence (SEQ ID NO: 4) of the $V_L$-region from HuMab 17G1. CDR regions are indicated.

FIG. 9 shows the nucleotide sequence (SEQ ID NO: 5) and corresponding amino acid sequence (SEQ ID NO: 6) of the $V_H$-region from HuMab 2H9. CDR regions are indicated.

FIG. 10 shows the nucleotide sequence (SEQ ID NO: 7) and corresponding amino acid sequence (SEQ ID NO: 8) of the $V_L$-region from HuMab 2H9. CDR regions are indicated.

FIG. 11 shows the nucleotide sequence (SEQ ID NO: 9) and corresponding amino acid sequence (SEQ ID NO: 10) of the $V_H$-region from HuMab 5F11. CDR regions are indicated.

FIG. 12 shows the nucleotide sequence (SEQ ID NO: 11) and corresponding amino acid sequence (SEQ ID NO: 12) of the $V_L$-region from HuMab 5F11. CDR regions are indicated.

FIG. 13 shows the nucleotide sequences (SEQ ID NOs: 49, 50, 51, 52, and 53) of the germline sequences $V_{H4}$-34, L15, $V_H$3-11, A27, and L6, respectively.

DETAILED DESCRIPTION OF THE INVENTION

Figure 1:
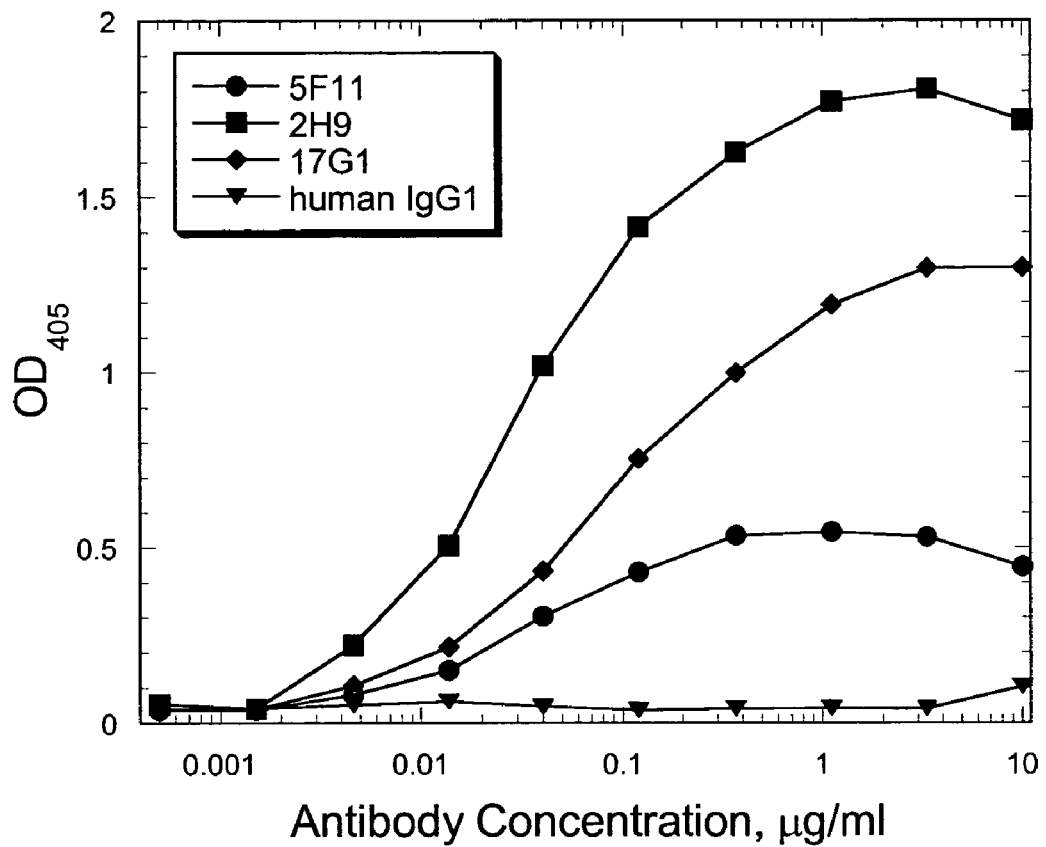
FIG. 1 is a graph comparing dose dependent binding of anti-CD30 HuMabs, 17G1, 5F11, 2H9 and an isotype control to recombinant CD30.

The present invention provides improved antibody-based therapies for treating and diagnosing a variety of disorders mediated by CD30 and/or CD30 expressing cells (e.g., disorders caused by the proliferative effects of CD30). Therapies of the invention employ isolated human monoclonal antibodies, or antigen binding portions thereof, which bind to and inhibit such functions of CD30 or CD30 expressing cells, particularly in human therapy.

In one embodiment, the human antibodies are produced in a non-human transgenic animal, e.g., a transgenic mouse, capable of producing multiple isotypes of human monoclonal antibodies to CD30 (e.g., IgG, IgA and/or IgE) by undergoing V-D-J recombination and isotype switching. Accordingly, particular aspects of the invention include not only antibodies, antibody fragments, and pharmaceutical compositions thereof, but also non-human transgenic animals, B-cells and hybridomas which produce monoclonal antibodies. Methods of using the antibodies of the invention to detect a cell expressing CD30, either in vitro or in vivo, are also encompassed by the invention. Methods of using the antibodies of the invention to block or inhibit CD30 induced activities, e.g., proliferative activities, are also provided and are useful in the treatment of disorders associated with CD30, such as tumorigenic diseases (e.g., Hodgkin's disease) and autoimmune diseases (e.g., HIV).

In order that the present invention may be more readily understood, certain terms are first defined. Additional definitions are set forth throughout the detailed description.

The terms "CD30" and "CD30 antigen" are used interchangeably herein, and include any variants, isoforms and species homologs of human CD30 which are naturally expressed by cells. In a preferred embodiment, binding of an antibody of the invention to the CD30-antigen-inhibits the growth of cells expressing CD30 (e.g., a tumor cell) by inhibiting or blocking binding of CD30 ligand to CD30. The term "CD30 ligand" encompasses all (e.g., physiological) ligands for CD30. In a preferred embodiment, the CD30 ligand is CD30L, CD153, TRAF1, TRAF2, TRAF3 or TRAF5. In another preferred embodiment, binding of an antibody of the invention to the CD30-antigen mediates effector cell phagocytosis and/or killing of cells expressing CD30. In yet another preferred embodiment, binding of an antibody of the invention to the CD30-antigen mediates effector cell ADCC of cells expressing CD30.

As used herein, the term "inhibits growth" (e.g., referring to cells) is intended to include any measurable decrease in the growth of a cell when contacted with an anti-CD30 antibody as compared to the growth of the same cell not in contact with an anti-CD30 antibody, e.g., the inhibition of growth of a cell by at least about 10%, 20%, 30%, 40%, 50%, 60%, 70%, 80%, 90%, 99%, or 100%.

The term "antibody" as referred to herein includes whole antibodies and any antigen binding fragment (i.e., "antigen-binding portion") or single chain thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, $C_{H1}$, $C_{H2}$ and $C_{H3}$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding portion" of an antibody (or simply "antibody portion"), as used herein, refers to one or more fragments of an antibody that retain the ability to bind to an antigen (e.g., CD30). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

As used herein, the terms "inhibits binding" and "blocks binding" (e.g., referring to inhibition/blocking of binding of CD30 ligand to CD30. Inhibition/blocking are used interchangeably and encompass both partial and complete inhibition/blocking. The inhibition/blocking of CD30 preferably reduces or alters the normal level or type of activity that occurs when CD30 binding occurs without inhibition or blocking, e.g., inhibition of CD30 induced proliferation. Inhibition and blocking are also intended to include any measurable decrease in the binding affinity of CD30 when in contact with an anti-CD30 antibody as compared to CD30 not in contact with an anti-CD30 antibody, e.g., the blocking of CD30 to its receptor by at least about 10%, 20%, 30%, 40%, 50%, 60%, 70%, 80%, 90% 99%, or 100%.

The term "bispecific molecule" is intended to include any agent, e.g., a protein, peptide, or protein or peptide complex, which has two different binding specificities. For example, the molecule may bind to, or interact with, (a) a cell surface antigen and (b) an Fc receptor on the surface of an effector cell. The term "multispecific molecule" or "heterospecific molecule" is intended to include any agent, e.g., a protein, peptide, or protein or peptide complex, which has more than two different binding specificities. For example, the molecule may bind to, or interact with, (a) a cell surface antigen, (b) an Fc receptor on the surface of an effector cell, and (c) at least one other component. Accordingly, the invention includes, but is not limited to, bispecific, trispecific, tetraspecific, and other multispecific molecules which are directed to cell surface antigens, such as CD30, and to other targets, such as Fc receptors on effector cells.

The term "bispecific antibodies" also includes diabodies. Diabodies are bivalent, bispecific antibodies in which the $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123).

As used herein, the term "heteroantibodies" refers to two or more antibodies, antibody binding fragments (e.g., Fab), derivatives therefrom, or antigen binding regions linked together, at least two of which have different specificities. These different specificities include a binding specificity for an Fc receptor on an effector cell, and a binding specificity for an antigen or epitope on a target cell, e.g., a tumor cell.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The terms "monoclonal antibody" or "monoclonal antibody composition" as used herein refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences. In one embodiment, the human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

The term "recombinant human antibody", as used herein, is intended to include all human antibodies that are prepared, expressed, created or isolated by recombinant means, such as (a) antibodies isolated from an animal (e.g., a mouse) that is transgenic for human immunoglobulin genes (described further in Section I, below), (b) antibodies expressed using a recombinant expression vector transfected into a host cell, (c) antibodies isolated from a recombinant, combinatorial human antibody library, and (c) antibodies prepared, expressed, created or isolated by any other means that involve splicing of human immunoglobulin gene sequences to other DNA sequences. Such recombinant human antibodies have variable and constant regions derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, a "heterologous antibody" is defined in relation to the transgenic non-human organism producing such an antibody. This term refers to an antibody having an amino acid sequence or an encoding nucleic acid sequence corresponding to that found in an organism not consisting of the transgenic non-human animal, and generally from a species other than that of the transgenic non-human animal.

As used herein, a "heterohybrid antibody" refers to an antibody having a light and heavy chains of different organismal origins. For example, an antibody having a human heavy chain associated with a murine light chain is a heterohybrid antibody. Examples of heterohybrid antibodies include chimeric and humanized antibodies, discussed supra.

An "isolated antibody," as used herein, is intended to refer to an antibody which is substantially free of other antibodies having different antigenic specificities (e.g., an isolated antibody that binds to CD30 is substantially free of antibodies that bind antigens other than CD30). An isolated antibody that binds to an epitope, isoform or variant of human CD30 may, however, have cross-reactivity to other related antigens, e.g., from other species (e.g., CD30 species homologs). Moreover, an isolated antibody may be substantially free of other cellular material and/or chemicals. In one embodiment of the invention, a combination of "isolated" monoclonal antibodies having different specificities are combined in a well defined composition.

As used herein, "specific binding" refers to antibody binding to a predetermined antigen. Typically, the antibody binds with an affinity of at least about $1\times10^7$ $M^{-1}$, and binds to the predetermined antigen with an affinity that is at least two-fold greater than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen".

As used herein, the term "high affinity" for an IgG antibody refers to a binding affinity of at least about $10^7 M^{-1}$, preferably at least about $10^8 M^{-1}$, more preferably at least about $10^9 M^{-1}, 10^{10} M^{-1}$, $10 M^{-1}$ or greater, e.g., up to $10^{13} M^{-1}$ or greater. However, "high affinity" binding can vary for other antibody isotypes. For example, "high affinity" binding for an IgM isotype refers to a binding affinity of at least about $1\times10^7 M^{-1}$.

The term "$K_{assoc}$" or "$K_a$", as used herein, is intended to refer to the association constant of a particular antibody-antigen interaction.

The term "$K_{dis}$" or "$K_d$", as used herein, is intended to refer to the dissociation constant of a particular antibody-antigen interaction.

As used herein, "isotype" refers to the antibody class (e.g., IgM or IgG1) that is encoded by heavy chain constant region genes.

As used herein, "isotype switching" refers to the phenomenon by which the class, or isotype, of an antibody changes from one Ig class to one of the other Ig classes.

As used herein, "nonswitched isotype" refers to the isotypic class of heavy chain that is produced when no isotype switching has taken place; the CH gene encoding the nonswitched isotype is typically the first CH gene immediately downstream from the functionally rearranged VDJ gene.

Isotype switching has been classified as classical or non-classical isotype switching. Classical isotype switching occurs by recombination events which involve at least one switch sequence region in the transgene. Non-classical isotype switching may occur by, for example, homologous recombination between human $\sigma_\mu$ and human $\Sigma_\mu$ ($\delta$-associated deletion). Alternative non-classical switching mechanisms, such as intertransgene and/or interchromosomal recombination, among others, may occur and effectuate isotype switching.

As used herein, the term "switch sequence" refers to those DNA sequences responsible for switch recombination. A "switch donor" sequence, typically a $\mu$ switch region, will be 5' (i.e., upstream) of the construct region to be deleted during the switch recombination. The "switch acceptor" region will be between the construct region to be deleted and the replacement constant region (e.g., $\gamma$, $\square$, etc.). As there is no specific site where recombination always occurs, the final gene sequence will typically not be predictable from the construct.

As used herein, "glycosylation pattern" is defined as the pattern of carbohydrate units that are covalently attached to a protein, more specifically to an immunoglobulin protein. A glycosylation pattern of a heterologous antibody can be characterized as being substantially similar to glycosylation patterns which occur naturally on antibodies produced by the species of the nonhuman transgenic animal, when one of ordinary skill in the art would recognize the glycosylation pattern of the heterologous antibody as being more similar to said pattern of glycosylation in the species of the nonhuman transgenic animal than to the species from which the CH genes of the transgene were derived.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "rearranged" as used herein refers to a configuration of a heavy chain or light chain immunoglobulin locus wherein a V segment is positioned immediately adjacent to a D-J or J segment in a conformation encoding essentially a complete $V_H$ or $V_L$ domain, respectively. A rearranged immunoglobulin gene locus can be identified by comparison to germline DNA; a rearranged locus will have at least one recombined heptamer/nonamer homology element.

The term "unrearranged" or "germline configuration" as used herein in reference to a V segment refers to the configuration wherein the V segment is not recombined so as to be immediately adjacent to a D or J segment.

The term "nucleic acid molecule", as used herein, is intended to include DNA molecules and RNA molecules. A nucleic acid molecule may be single-stranded or double-stranded, but preferably is double-stranded DNA.

The term "isolated nucleic acid molecule," as used herein in reference to nucleic acids encoding antibodies or antibody portions (e.g., $V_H$, $V_L$, CDR3) that bind to CD30, is intended to refer to a nucleic acid molecule in which the nucleotide sequences encoding the antibody or antibody portion are free of other nucleotide sequences encoding antibodies or antibody portions that bind antigens other than CD30, which other sequences may naturally flank the nucleic acid in human genomic DNA. In one embodiment, the human anti-CD30 antibody, or portion thereof, includes the nucleotide or amino acid sequence of 17G1, 2H9 or 5F11, and heavy chain ($V_H$) variable regions having the sequence shown in SEQ ID NOs: 1 and 2, 5 and 6, and 9 and 10, respectively, and light chain (VL) variable regions having the sequences shown in SEQ ID NOs: 3 and 4, 7 and 8, and 11 and 12, respectively.

As disclosed and claimed herein, the sequences set forth in SEQ ID NOs: 1-12 include "conservative sequence modifications", i.e., nucleotide and amino acid sequence modifications which do not significantly affect or alter the binding characteristics of the antibody encoded by the nucleotide sequence or containing the amino acid sequence. Such conservative sequence modifications include nucleotide and amino acid substitutions, additions and deletions. Modifications can be introduced into SEQ ID NOs: 1-12 by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in a human anti-CD30 antibody is preferably replaced with another amino acid residue from the same side chain family.

Alternatively, in another embodiment, mutations can be introduced randomly along all or part of an anti-CD30 antibody coding sequence, such as by saturation mutagenesis, and the resulting modified anti-CD30 antibodies can be screened for binding activity.

Accordingly, antibodies encoded by the (heavy and light chain variable region) nucleotide sequences disclosed herein and/or containing the (heavy and light chain variable region) amino acid sequences disclosed herein (i.e., SEQ ID NOs: 1-12) include substantially similar antibodies encoded by or containing similar sequences which have been conservatively modified. Further discussion as to how such substantially similar antibodies can be generated based on the partial (i.e., heavy and light chain variable regions) sequences disclosed herein as SEQ ID NOs: 1-12 is provided below.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial homology exists when the segments will hybridize under selective hybridization conditions, to the complement of the strand.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also determined using the algorithm of E. Meyers and W. Miller (*Comput. Appl. Biosci.*, 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* 48:444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences of the present invention can further be used as a "query sequence" to perform a search against public databases to, for example, identify related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See http://www.ncbi.nlm.nih.gov.

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. *Current Protocols in Molecular Biology*, Greene Publishing and Wiley Interscience, New York (1987).

The nucleic acid compositions of the present invention, while often in a native sequence (except for modified restriction sites and the like), from either cDNA, genomic or mixtures may be mutated, thereof in accordance with standard techniques to provide gene sequences. For coding sequences, these mutations, may affect amino acid sequence as desired. In particular, DNA sequences substantially homologous to or derived from native V, D, J, constant, switches and other such sequences described herein are contemplated (where "derived" indicates that a sequence is identical or modified from another sequence).

A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. Recombinant host cells include, for example, CHO cells and lymphocytic cells.

The term "transfectoma", as used herein, includes recombinant eukaryotic host cell expressing the antibody, such as CHO cells or NS/0 cells.

As used herein, the term "subject" includes any human or nonhuman animal. The term "nonhuman animal" includes all vertebrates, e.g., mammals and non-mammals, such as nonhuman primates, sheep, dog, cow, chickens, amphibians, reptiles, etc.

The terms "transgenic, nonhuman animal" refers to a nonhuman animal having a genome comprising one or more human heavy and/or light chain transgenes or transchromosomes (either integrated or non-integrated into the animal's natural genomic DNA) and which is capable of expressing fully human antibodies. For example, a transgenic mouse can have a human light chain transgene and either a human heavy chain transgene or human heavy chain transchromosome, such that the mouse produces human anti-CD64 antibodies when immunized with CD64 antigen and/or cells expressing CD64. The human heavy chain transgene can be integrated into the chromosomal DNA of the mouse, as is the case for transgenic, e.g., HuMAb mice, or the human heavy chain transgene can be maintained extrachromosomally, as is the case for transchromosomal (e.g., KM) mice as described in WO 02/43478. Such transgenic and transchromosomal mice are capable of producing multiple isotypes of human monoclonal antibodies to CD64 (e.g., IgG, IgA and/or IgE) by undergoing V-D-J recombination and isotype switching.

Various aspects of the invention are described in further detail in the following subsections.

I. Production of Human Antibodies to CD30

The monoclonal antibodies (MAbs) of the invention can be produced by a variety of techniques, including conventional monoclonal antibody methodology e.g., the standard somatic cell hybridization technique of Kohler and Milstein (1975) *Nature* 256: 495. Although somatic cell hybridization procedures are preferred, in principle, other techniques for producing monoclonal antibody can be employed e.g., viral or oncogenic transformation of B lymphocytes.

The preferred animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known.

In a preferred embodiment, human monoclonal antibodies directed against CD30 can be generated using transgenic mice carrying parts of the human immune system rather than the mouse system. These transgenic mice, referred to herein as "HuMAb" mice, contain a human immunoglobulin gene miniloci that encodes unrearranged human heavy ($\mu$ and $\gamma$) and $\kappa$ light chain immunoglobulin sequences, together with targeted mutations that inactivate the endogenous $\mu$ and $\kappa$ chain loci (Lonberg, et al. (1994) *Nature* 368(6474): 856-859). Accordingly, the mice exhibit reduced expression of mouse IgM or $\kappa$ and in response to immunization, the introduced human heavy and light chain transgenes undergo class switching and somatic mutation to generate high affinity human IgG$\kappa$ monoclonal (Lonberg, N. et al. (1994), supra; reviewed in Lonberg, N. (1994) *Handbook of Experimental Pharmacology* 113:49-101; Lonberg, N. and Huszar, D. (1995) *Intern. Rev. Immunol*. Vol. 13: 65-93, and Harding, F. and Lonberg, N. (1995) *Ann. N.Y. Acad. Sci* 764:536-546). The preparation of HuMAb mice is described in detail Section II below and in Taylor, L. et al. (1992) *Nucleic Acids Research* 20:6287-6295; Chen, J. et al. (1993) *International Immunology* 5: 647-656; Tuaillon et al. (1993) *Proc. Natl. Acad. Sci USA* 90:3720-3724; Choi et al. (1993) *Nature Genetics* 4:117-123; Chen, J. et al. (1993) *EMBO J*. 12: 821-830; Tuaillon et al. (1994) *J. Immunol*. 152:2912-2920; Lonberg et al., (1994) *Nature* 368(6474): 856-859; Lonberg, N. (1994) *Handbook of Experimental Pharmacology* 113: 49-101; Taylor, L. et al. (1994) *International Immunology* 6: 579-591; Lonberg, N. and Huszar,.D. (1995) *Intern. Rev. Immunol*. Vol. 13: 65-93; Harding, F. and Lonberg, N. (1995) *Ann. N.Y. Acad. Sci* 764:536-546; Fishwild, D. et al. (1996) *Nature Biotechnolgy* 14: 845-851, the contents of all of which are hereby incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay, and GenPharm International; U.S. Pat. No. 5,545,807 to Surani et al.; International Publication Nos. WO 98/24884, published on Jun. 11, 1998; WO 94/25585, published Nov. 10, 1994; WO 93/1227, published Jun. 24, 1993; WO 92/22645, published Dec. 23, 1992; WO 92/03918, published Mar. 19, 1992, the disclosures of all of which are hereby incorporated by reference in their entity. Alternatively, the HCO12 transgenic mice described in Example 2, can be used to generate human anti-CD30 antibodies.

HuMAb Immunizations

To generate fully human monoclonal antibodies to CD30, HuMAb mice can be immunized with a purified or enriched preparation of CD30 antigen and/or cells expressing CD30, as described by Lonberg, N. et al. (1994) *Nature* 368(6474): 856-859; Fishwild, D. et al. (1996) *Nature Biotechnology* 14: 845-851 and WO 98/24884. Preferably, the mice will be 6-16 weeks of age upon the first infusion. For example, a purified or enriched preparation (5-20 µg) of CD30 antigen (e.g., purified from CD30-expressing LNCaP cells) can be used to immunize the HuMAb mice intraperitoneally. In the event that immunizations using a purified or enriched preparation of CD30 antigen do not result in antibodies, mice can also be immunized with cells expressing CD30, e.g., a tumor cell line, to promote immune responses.

Cumulative experience with various antigens has shown that the HuMAb transgenic mice respond best when initially immunized intraperitoneally (IP) with antigen in complete Freund's adjuvant, followed by every other week i.p. immunizations (up to a total of 6) with antigen in incomplete Freund's adjuvant. The immune response can be monitored over the course of the immunization protocol with plasma samples being obtained by retroorbital bleeds. The plasma can be screened by ELISA (as described below), and mice with sufficient titers of anti-CD30 human immunoglobulin can be used for fusions. Mice can be boosted intravenously with antigen 3 days before sacrifice and removal of the spleen. It is expected that 2-3 fusions for each antigen may need to be performed. Several mice will be immunized for each antigen. For example, a total of twelve HuMAb mice of the HC07 and HC012 strains can be immunized.

Generation of Hybridomas Producing Human Monoclonal Antibodies to CD30

The mouse splenocytes can be isolated and fused with PEG to a mouse myeloma cell line based upon standard protocols. The resulting hybridomas are then screened for the production of antigen-specific antibodies. For example, single cell suspensions of splenic lymphocytes from immunized mice are fused to one-sixth the number of P3X63-Ag8.653 nonsecreting mouse myeloma cells (ATCC, CRL 1580) with 50% PEG. Cells are plated at approximately $2 \times 10^5$ in flat bottom microtiter plate, followed by a two week incubation in selective medium containing 20% fetal Clone Serum, 18% "653" conditioned media, 5% origen (IGEN), 4 mM L-glutamine, 1 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin and 1X HAT (Sigma; the HAT is added 24 hours after the fusion). After two weeks, cells are cultured in medium in which the HAT is replaced with HT. Individual wells are then screened by ELISA for human anti-CD30 monoclonal IgM and IgG antibodies. Once extensive hybridoma growth occurs, medium is observed usually after 10-14 days. The antibody secreting hybridomas are replated, screened again, and if still positive for human IgG, anti-CD30 monoclonal antibodies, can be subcloned at least twice by limiting dilution. The stable subcloned are then cultured in vitro to generate small amounts of antibody in tissue culture medium for characterization.

Generation of Transfectomas Producing Human Monoclonal Antibodies to CD30

Human antibodies of the invention also can be produced in a host cell transfectoma using, for example, a combination of recombinant DNA techniques and gene transfection methods as is well known in the art (e.g., Morrison, S. (1985) *Science* 229:1202).

For example, to express the antibodies, or antibody fragments thereof, DNAs encoding partial or full-length light and heavy chains, can be obtained by standard molecular biology techniques (e.g., PCR amplification, site directed mutagenesis) and can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to includes promoters, enhancers and other expression control elements (e.g., polyadenylation signals) that control the transcription or translation of the antibody chain genes. Such regulatory sequences are described, for example, in Goeddel; Gene Expression Technology. Methods in Enzymology 185, Academic Press, San Diego, Calif. (1990). It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP)) and polyoma. Alternatively, nonviral regulatory sequences may be used, such as the ubiquitin promoter or β-globin promoter.

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399, 216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr- host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) Inmunology Today 6:12-13).

Preferred mammalian host cells for expressing the recombinant antibodies of the invention include Chinese Hamster Ovary (CHO cells) (including dhfr- CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *Mol. Biol.* 159:601-621), NSO myeloma cells, COS cells and SP2 cells. In particular, for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Use of Partial Antibody Sequences to Express Intact Antibodies

Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al., 1998, *Nature* 332:323-327; Jones, P. et al., 1986, *Nature* 321:522-525; and Queen, C. et al., 1989, *Proc. Natl. Acad. See. U.S.A.* 86:10029-10033). Such framework sequences can be obtained from public DNA databases that include germline antibody gene sequences. These germline sequences will differ from mature antibody gene sequences because they will not include completely assembled variable genes, which are formed by V(D)J joining during B cell maturation. Germline gene sequences will also differ from the sequences of a high affinity secondary repertoire antibody at individual evenly across the variable region. For example, somatic mutations are relatively infrequent in the amino-terminal portion of framework region. For example, somatic mutations are relatively infrequent in the amino terminal portion of framework region 1 and in the carboxy-terminal portion of framework region 4. Furthermore, many somatic mutations do not significantly alter the binding properties of the antibody. For this reason, it is not necessary to obtain the entire DNA sequence of a particular antibody in order to recreate an intact recombinant antibody having binding properties similar to those of the original antibody (see PCT/US99/05535 filed on Mar. 12, 1999, which is herein incorporated by referenced for all purposes). Partial heavy and light chain sequence spanning the CDR regions is typically sufficient for this purpose. The partial sequence is used to determine which germline variable and joining gene segments contributed to the recombined antibody variable genes. The germline sequence is then used to fill in missing portions of the variable regions. Heavy and light chain leader sequences are cleaved during protein maturation and do not contribute to the properties of the final antibody. For this reason, it is necessary to use the corresponding germline leader sequence for expression constructs. To add missing sequences, cloned cDNA sequences cab be combined with synthetic oligonucleotides by ligation or PCR amplification. Alternatively, the entire variable region can be synthesized as a set of short, overlapping, oligonucleotides and combined by PCR amplification to create an entirely synthetic variable region clone. This process has certain advantages such as elimination or inclusion or particular restriction sites, or optimization of particular codons.

The nucleotide sequences of heavy and light chain transcripts from a hybridomas are used to design an overlapping set of synthetic oligonucleotides to create synthetic V sequences with identical amino acid coding capacities as the natural sequences. The synthetic heavy and kappa chain sequences can differ from the natural sequences in three ways: strings of repeated nucleotide bases are interrupted to facilitate oligonucleotide synthesis and PCR amplification; optimal translation initiation sites are incorporated according to Kozak's rules (Kozak, 1991, J. Biol. Chem. 266: 19867-19870); and, HindIII sites are engineered upstream of the translation initiation sites.

For both the heavy and light chain variable regions, the optimized coding, and corresponding non-coding, strand sequences are broken down into 30-50 nucleotide approximately the midpoint of the corresponding non-coding oligonucleotide. Thus, for each chain, the oligonucleotides can be assemble into overlapping double stranded sets that span segments of 150-400 nucleotides. The pools are then used as templates to produce PCR amplification products of 150-400 nucleotides. Typically, a single variable region oligonucleotide set will be broken down into two pools which are separately amplified to generate two overlapping PCV products. These overlapping products are then combined by PCT amplification to form the complete variable region. It may also be desirable to include an overlapping fragment of the heavy or light chain constant region (including the BbsI site of the kappa light chain, or the AgeI site if the gamma heavy chain) in the PCR amplification to generate fragments that can easily be cloned into the expression vector constructs.

The reconstructed heavy and light chain variable regions are then combined with cloned promoter, translation initiation, constant region, 3' untranslated, polyadenylation, and transcription termination, sequences to form expression vector constructs. The heavy and light chain expression constructs can be combined into a single vector, co-transfected, serially transfected, or separately transfected into host cells which are then fused to form a host cell expressing both chains.

Plasmids for use in construction of expression vectors for human IgGκ are described below. The plasmids were constructed so that PCR amplified V heavy and V kappa light chain cDNA sequences could be used to reconstruct complete heavy and light chain minigenes. These plasmids can be used to express completely human, or chimeric $IgG_1\kappa$ or $IgG_4\kappa$ antibodies. Similar plasmids can be constructed for expression of other heavy chain isotypes, or for expression of antibodies comprising lambda light chains.

Thus, in another aspect of the invention, the structural features of a human anti-CD30 antibody of the invention, e.g., 17G1, 2H9, or 5F11, are used to create structurally related human anti-CD30 antibodies that retain at least one functional property of the antibodies of the invention, such as binding to CD30. More specifically, one or more CDRs of 17G1, 2H9, or 5F11 can be combined recombinantly with known human framework regions and CDRs to create additional, recombinantly-engineered, human anti-CD30 antibodies of the invention.

Accordingly, in another embodiment, the invention provides a method for preparing an anti-CD30 antibody comprising:

preparing an antibody comprising (1) human heavy chain framework regions and human heavy chain CDRs, wherein at least one of the human heavy chain CDRs comprises an amino acid sequence selected from the amino acid sequences of CDRs shown in FIG. 7, 9, or 11 (SEQ ID NOs: 16, 17, 18, 28, 29, 30, 40, 41 and 42); and (2) human light chain framework regions and human light chain CDRs, wherein at least one of the light chain CDRs comprises an amino acid sequence selected from the amino acid sequences of CDRs shown in FIG. 8, 10, or 12 (SEQ ID NOs: 22, 23, 24, 34, 35, 36, 46, 47 and 48);

wherein the antibody retains the ability to bind to CD30. The ability of the antibody to bind CD30 can be determined using standard binding assays, such as those set forth in the Examples (e.g., an ELISA).

Since it is well known in the art that antibody heavy and light chain CDR3 domains play a particularly important role in the binding specificity/affinity of an antibody for an antigen, the recombinant antibodies of the invention prepared, as set forth above, preferably comprise the heavy and light chain CDR3s of 10F8. The antibodies further can comprise the CDR2s of 17G1, 2H9, or 5F11. The antibodies further can comprise the CDR1s of 17G1, 2H9, or 5F11. The antibodies can further comprise any combinations of the CDRs.

Accordingly, in another embodiment, the invention further provides anti-CD30 antibodies comprising: (1) human heavy chain framework regions, a human heavy chain CDR1 region, a human heavy chain CDR2 region, and a human heavy chain CDR3 region, wherein the human heavy chain CDR3 region is the heavy chain CDR3 of 17G1, 2H9, or 5F11 as shown in FIG. 7, 9, or 11 (SEQ ID NOs: 18, 30, or 42); and (2) human light chain framework regions, a human light chain CDR1 region, a human light chain CDR2 region, and a human light chain CDR3 region, wherein the human light chain CDR3 region is the light chain CDR3 of 17G1, 2H9, or 5F11 as shown in FIG. 8, 10, or 12 (SEQ ID NO: 24, 36, or 48), wherein the antibody binds CD30. The antibody may further comprise the heavy chain CDR2 and/or the light chain CDR2 of 17G1, 2H9, or 5F11. The antibody may further comprise the heavy chain CDR1 and/or the light chain CDR1 of 17G1, 2H9, or 5F11.

The CDR1, 2, and/or 3 regions of the engineered antibodies described above can comprise the exact amino acid sequence(s) as those of 17G1, 2H9, or 5F11 disclosed herein. However, the ordinarily skilled artisan will appreciate that some deviation from the exact CDR sequences of 17G1, 2H9, or 5F11 may be possible while still retaining the ability of the antibody to bind CD30 effectively. Accordingly, in another embodiment, the engineered antibody may be composed of one or more CDRs that are, for example, 95%, 98% or 99.5% identical to one or more CDRs of 17G1, 2H9, or 5F11.

In addition, or alternative, to simply binding CD30, engineered antibodies such as those described above may be selected for their retention of other functional properties of antibodies of the invention, such as:

(1) binding to human CD30 and inhibiting growth of tumor cells expressing CD30;

(2) inhibiting binding of CD30 ligand binding to human CD30;

(3) inducing ADCC of tumor cells expressing CD30 in the presence of effector cells;

(4) inducing phagocytosis of tumor cells expressing CD30 in the presence of macrophages; and/or (5) binding to human CD30 with an equilibrium constant (Ka) of at least $10^8$ $M^{-1}$.

Characterization of Binding of Human Monoclonal Antibodies to CD30

To characterize binding of human monoclonal CD30 antibodies of the invention, sera from immunized mice can be tested, for example, by ELISA. In a typical (but non-limiting) example of an ELISA protocol, microtiter plates are coated with purified CD30 at 0.25 μg/ml in PBS, and then blocked with 5% bovine serum albumin in PBS. Dilutions of plasma from CD30-immunized mice are added to each well and incubated for 1-2 hours at 37° C. The plates are washed with PBS/Tween and then incubated with a goat-anti-human IgG Fc-specific polyclonal reagent conjugated to alkaline phosphatase for 1 hour at 37° C. After washing, the plates are developed with pNPP substrate (1 mg/ml), and analyzed at OD of 405-650. Preferably, mice which develop the highest titers will be used for fusions.

An ELISA assay as described above can also be used to screen for hybridomas that show positive reactivity with CD30 immunogen. Hybridomas that bind with high avidity to CD30 will be subcloned and further characterized. One clone from each hybridoma, which retains the reactivity of the parent cells (by ELISA), can be chosen for making a 5-10 vial cell bank stored at −140° C., and for antibody purification.

To purify human anti-CD30 antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by $OD_{280}$ using 1.43 extinction coefficient. The monoclonal antibodies can be aliquoted and stored at −80° C.

To determine if the selected human anti-CD30 monoclonal antibodies bind to unique epitopes, each antibody can be biotinylated using commercially available reagents (Pierce, Rockford, Ill.). Competition studies using unlabeled monoclonal antibodies and biotinylated monoclonal antibodies can be performed using CD30 coated-ELISA plates as described above. Biotinylated MAb binding can be detected with a strep-avidin-alkaline phosphatase probe.

To determine the isotype of purified antibodies, isotype ELISAs can be performed. For example, wells of microtiter plates can be coated with 10 μg/ml of anti-human Ig overnight at 4° C. After blocking with 5% BSA, the plates are reacted with 10 μg/ml of monoclonal antibodies or purified isotype controls, at ambient temperature for two hours. The wells can then be reacted with either human IgG1 or human IgM-specific alkaline phosphatase-conjugated probes. Plates are developed and analyzed as described above.

In order to demonstrate binding of monoclonal antibodies to live cells expressing the CD30, flow cytometry can be used. In a typical (but non-limiting) example of a flow cytometry protocol, cell lines expressing CD30 (grown under standard growth conditions) are mixed with various concentrations of monoclonal antibodies in PBS containing 0.1% BSA and 20% mouse serum, and incubated at 37° C. for 1 hour. After washing, the cells are reacted with Fluorescein-labeled anti-human IgG antibody under the same conditions as the primary antibody staining. The samples can be analyzed by FACScan instrument using light and side scatter properties to gate on single cells. An alternative assay using fluorescence microscopy may be used (in addition to or instead of) the flow cytometry assay. Cells can be stained exactly as described above and examined by fluorescence microscopy. This method allows visualization of individual cells, but may have diminished sensitivity depending on the density of the antigen.

Anti-CD30 human IgGs can be further tested for reactivity with CD30 antigen by Western blotting. For example, cell extracts from cells expressing CD30 can be prepared and subjected to sodium dodecyl sulfate (SDS) polyacrylamide gel electrophoresis. After electrophoresis, the separated antigens will be transferred to nitrocellulose membranes, blocked with 20% mouse serum, and probed with the monoclonal antibodies to be tested. Human IgG binding can be detected using anti-human IgG alkaline phosphatase and developed with BCIP/NBT substrate tablets (Sigma Chem. Co., St. Louis, Mo.).

Phagocytic and Cell Killing Activities of Human Monoclonal Antibodies to CD30

In addition to binding specifically to CD30, human monoclonal anti-CD30 antibodies can be tested for their ability to mediate phagocytosis and killing of cells expressing CD30. The testing of monoclonal antibody activity in vitro will provide an initial screening prior to testing in vivo models. Briefly, polymorphonuclear cells (PMN), or other effector cells, from healthy donors can be purified by Ficoll Hypaque density centrifugation, followed by lysis of contaminating erythrocytes. Washed PMNs, can be suspended in RPMI supplemented with 10% heat-inactivated fetal calf serum and mixed with $^{51}Cr$ labeled cells expressing CD30, at various ratios of effector cells to tumor cells (-effector cells:tumor cells). Purified human anti-CD30 IgGs can then be added at various concentrations. Irrelevant human IgG can be used as negative control. Assays can be carried out for 4-18 hours at 37° C. Samples can be assayed for cytolysis by measuring $^{51}Cr$ release into the culture supernatant. Anti-CD30 monoclonal can also be tested in combinations with each other to determine whether cytolysis is enhanced with multiple monoclonal antibodies.

Human monoclonal antibodies which bind to CD30 also can be tested in an in vivo model (e.g., in mice) to determine their efficacy in mediating phagocytosis and killing of cells expressing CD30, e.g., tumor cells. These antibodies can be selected, for example, based on the following criteria, which are not intended to be exclusive:

1.) binding to live cells expressing CD30;
2.) high affinity of binding to CD30;
3.) binding to a unique epitope on CD30 (to eliminate the possibility that monoclonal antibodies with complimentary activities when used in combination would compete for binding to the same epitope);
4.) opsonization of cells expressing CD30;
5.) mediation of growth inhibition, phagocytosis and/or killing of cells expressing CD30 in the presence of human effector cells.

Preferred human monoclonal antibodies of the invention meet one or more, and preferably all, of these criteria. In a particular embodiment, the human monoclonal antibodies are used in combination, e.g., as a pharmaceutical composition comprising two or more anti-CD30 monoclonal antibodies or fragments thereof. For example, human anti-CD30 monoclonal antibodies having different, but complementary activities can be combined in a single therapy to achieve a desired therapeutic or diagnostic effect. An illustration of this would be a composition containing an anti-CD30 human monoclonal antibody that mediates highly effective killing of target cells in the presence of effector cells, combined with another human anti-CD30 monoclonal antibody that inhibits the growth of cells expressing CD30.

II. Production of Transgenic Nonhuman Animals which Generate Human Monoclonal Anti-CD30 Antibodies In yet another aspect, the invention provides transgenic and transchromosomal nonhuman animals, such as transgenic or transchromosomal mice, which are capable of expressing human monoclonal antibodies that specifically bind to CD30. In a particular embodiment, the invention provides a transgenic or transchromosomal mouse having a genome comprising a human heavy chain transgene, such that the mouse produces human anti-CD30 antibodies when immunized with CD30 antigen and/or cells expressing CD30. The human heavy chain transgene can be integrated into the chromosomal DNA of the mouse, as is the case for transgenic, e.g., HuMAb mice, as described in detail herein and exemplified. Alternatively, the human heavy chain transgene can be maintained extrachromosomally, as is the case for transchromosomal (e.g., KM) mice as described in WO 02/43478. Such transgenic and transchromosomal animals are capable of producing multiple isotypes of human monoclonal antibodies to CD30 (e.g., IgG, IgA and/or IgE) by undergoing V-D-J recombination and isotype switching. Isotype switching may occur by, e.g., classical or non-classical isotype switching.

The design of a transgenic or transchromosomal nonhuman animal that responds to foreign antigen stimulation with a heterologous antibody repertoire, requires that the heterologous immunoglobulin transgenes contained within the transgenic animal function correctly throughout the pathway of B-cell development. This includes, for example, isotype switching of the heterologous heavy chain transgene. Accordingly, transgenes are constructed so as to produce isotype switching and one or more of the following of antibodies: (1) high level and cell-type specific expression, (2) functional gene rearrangement, (3) activation of and response to allelic exclusion, (4) expression of a sufficient primary repertoire, (5) signal transduction, (6) somatic hypermutation, and (7) domination of the transgene antibody locus during the immune response.

Not all of the foregoing criteria need be met. For example, in those embodiments wherein the endogenous immunoglobulin loci of the transgenic animal are functionally disrupted, the transgene need not activate allelic exclusion. Further, in those embodiments wherein the transgene comprises a functionally rearranged heavy and/or light chain immunoglobulin gene, the second criteria of functional gene rearrangement is unnecessary, at least for that transgene which is already rearranged. For background on molecular immunology, see, *Fundamental Immunology*, 2nd edition (1989), Paul William E., ed. Raven Press, N.Y.

In certain embodiments, the transgenic or transchromosomal nonhuman animals used to generate the human monoclonal antibodies of the invention contain rearranged, unrearranged or a combination of rearranged and unrearranged heterologous immunoglobulin heavy and light chain transgenes in the germline of the transgenic animal. Each of the heavy chain transgenes comprises at least one $C_H$ gene. In addition, the heavy chain transgene may contain functional isotype switch sequences, which are capable of supporting isotype switching of a heterologous transgene encoding multiple $C_H$ genes in the B-cells of the transgenic animal. Such switch sequences may be those which occur naturally in the germline immunoglobulin locus from the species that serves as the source of the transgene $C_H$ genes, or such switch sequences may be derived from those which occur in the species that is to receive the transgene construct (the transgenic animal). For example, a human transgene construct that is used to produce a transgenic mouse may produce a higher frequency of isotype switching events if it incorporates switch sequences similar to those that occur naturally in the mouse heavy chain locus, as presumably the mouse switch sequences are optimized to function with the mouse switch recombinase enzyme system, whereas the human switch sequences are not. Switch sequences may be isolated and cloned by conventional cloning methods, or may be synthesized de novo from overlapping synthetic oligonucleotides designed on the basis of published sequence information relating to immunoglobulin switch region sequences (Mills et al, *Nucl. Acids Res.* 15:7305-7316 (1991); Sideras et al., *Intl. Immunol.* 1:631-642 (1989)). For each of the foregoing transgenic animals, functionally rearranged heterologous heavy and light chain immunoglobulin transgenes are found in a significant fraction of the B-cells of the transgenic animal (at least 10 percent).

The transgenes used to generate the transgenic nonhuman animals used to produce the human monoclonal antibodies of the invention include a heavy chain transgene comprising DNA encoding at least one variable gene segment, one diversity gene segment, one joining gene segment and at least one constant region gene segment. The immunoglobulin light chain transgene comprises DNA encoding at least one variable gene segment, one joining gene segment and at least one constant region gene segment. The gene segments encoding the light and heavy chain gene segments are heterologous to the transgenic animal in that they are derived from, or correspond to, DNA encoding immunoglobulin heavy and light chain gene segments from a species not consisting of the transgenic nonhuman animal. In one aspect of the invention, the transgene is constructed such that the individual gene segments are unrearranged, i.e., not rearranged so as to encode a functional immunoglobulin light or heavy chain. Such unrearranged transgenes support recombination of the V, D, and J gene segments (functional rearrangement) and preferably support incorporation of all or a portion of a D region gene segment in the resultant rearranged immunoglobulin heavy chain within the transgenic animal when exposed to CD30 antigen.

In an alternate embodiment, the transgenes comprise an unrearranged "mini-locus". Such transgenes typically comprise a substantial portion of the C, D, and J segments as well as a subset of the V gene segments. In such transgene constructs, the various regulatory sequences, e.g., promoters, enhancers, class switch regions, splice-donor and splice-acceptor sequences for RNA processing, recombination signals and the like, comprise corresponding sequences derived from the heterologous DNA. Such regulatory sequences may be incorporated into the transgene from the same or a related species of the nonhuman animal used in the invention. For example, human immunoglobulin gene segments may be combined in a transgene with a rodent immunoglobulin enhancer sequence for use in a transgenic mouse. Alternatively, synthetic regulatory sequences may be incorporated into the transgene, wherein such synthetic regulatory sequences are not homologous to a functional DNA sequence that is known to occur naturally in the genomes of mammals. Synthetic regulatory sequences are designed according to consensus rules, such as, for example, those specifying the permissible sequences of a splice-acceptor site or a promoter/enhancer motif. For example, a minilocus comprises a portion of the genomic immunoglobulin locus having at least one internal (i.e., not at a terminus of the portion) deletion of a non-essential DNA portion (e.g., intervening sequence; intron or portion thereof) as compared to the naturally-occurring germline Ig locus.

In a preferred embodiment of the invention, the transgenic or transchromosomal animal used to generate human antibodies to CD30 contains at least one, typically 2-10, and sometimes 25-50 or more copies of the transgene described in Example 12 of WO 98/24884 (e.g., pHC1 or pHC2) bred with an animal containing a single copy of a light chain transgene described in Examples 5, 6, 8, or 14 of WO 98/24884, and the offspring bred with the $J_H$ deleted animal described in Example 10 of WO 98/24884. Animals are bred to homozygosity for each of these three traits. Such animals have the following genotype: a single copy (per haploid set of chromosomes) of a human heavy chain unrearranged mini-locus (described in Example 12 of WO 98/24884), a single copy (per haploid set of chromosomes) of a rearranged human κ light chain construct (described in Example 14 of WO 98/24884), and a deletion at each endogenous mouse heavy chain locus that removes all of the functional $J_H$ segments (described in Example 10 of WO 98/24884). Such animals are bred with mice that are homozygous for the deletion of the $J_H$ segments (Example 10 of WO 98/24884) to produce offspring that are homozygous for the $J_H$ deletion and hemizygous for the human heavy and light chain constructs. The resultant animals are injected with antigens and used for production of human monoclonal antibodies against these antigens.

B cells isolated from such an animal are monospecific with regard to the human heavy and light chains because they contain only a single copy of each gene. Furthermore, they will be monospecific with regards to human or mouse heavy chains because both endogenous mouse heavy chain gene copies are nonfunctional by virtue of the deletion spanning the $J_H$ region introduced as described in Examples 9 and 12 of WO 98/24884. Furthermore, a substantial fraction of the B cells will be monospecific with regards to the human or mouse light chains because expression of the single copy of the rearranged human κ light chain gene will allelically and isotypically exclude the rearrangement of the endogenous mouse κ and lambda chain genes in a significant fraction of B-cells.

Preferred transgenic and transchromosomal nonhuman animals, e.g., mice, will exhibit immunoglobulin production with a significant repertoire, ideally substantially similar to that of a native mouse. Thus, for example, in embodiments where the endogenous Ig genes have been inactivated, the total immunoglobulin levels will range from about 0.1 to 10 mg/ml of serum, preferably 0.5 to 5 mg/ml, ideally at least about 1.0 mg/ml. When a transgene capable of effecting a switch to IgG from IgM has been introduced into the transgenic mouse, the adult mouse ratio of serum IgG to IgM is preferably about 10:1. The IgG to IgM ratio will be much lower in the immature mouse. in general, greater than about 10%, preferably 40 to 80% of the spleen and lymph node B cells express exclusively human IgG protein.

The repertoire will ideally approximate that shown in a native mouse, usually at least about 10% as high, preferably 25 to 50% or more. Generally, at least about a thousand different immunoglobulins (ideally IgG), preferably $10^4$ to $10^6$ or more, will be produced, depending primarily on the number of different V, J and D regions introduced into the mouse genome. These immunoglobulins will typically recognize about one-half or more of highly antigenic proteins, e.g., staphylococcus protein A. Typically, the immunoglobulins will exhibit an affinity ($K_D$) for preselected antigens of below $10^{-7}$ M, such as of below $10^{-8}$ M, $10^{-9}$ M or $10^{-10}$ M or even lower. In some embodiments, it may be preferable to generate nonhuman animals with predetermined repertoires to limit the selection of V genes represented in the antibody response to a predetermined antigen type. A heavy chain transgene having a predetermined repertoire may comprise, for example, human $V_H$ genes which are preferentially used in antibody responses to the predetermined antigen type in humans. Alternatively, some $V_H$ genes may be excluded from a defined repertoire for various reasons (e.g., have a low likelihood of encoding high affinity V regions for the predetermined antigen; have a low propensity to undergo somatic mutation and affinity sharpening; or are immunogenic to certain humans). Thus, prior to rearrangement of a transgene containing various heavy or light chain gene segments, such gene segments may be readily identified, e.g., by hybridization or DNA sequencing, as being from a species of organism other than the transgenic animal.

Transgenic and transchromosomal nonhuman animals, e.g., mice, as described above can be immunized with, for example, a purified or recombinant preparation of CD30 antigen and/or cells expressing CD30. Alternatively, the transgenic animals can be immunized with DNA encoding human CD30. The animals will then produce B cells which undergo class-switching via intratransgene switch recombination (cis-switching) and express immunoglobulins reactive with CD30. The immunoglobulins can be human antibodies (also referred to as "human sequence antibodies"), wherein the heavy and light chain polypeptides are encoded by human transgene sequences, which may include sequences derived by somatic mutation and V region recombinatorial joints, as well as germline-encoded sequences; these human antibodies can be referred to as being substantially identical to a polypeptide sequence encoded by a human $V_L$ or $V_H$ gene segment and a human $J_L$ or $D_H$ and $J_H$ segment, even though other non-germline sequences may be present as a result of somatic mutation and differential V-J and V-D-J recombination joints. The variable regions of each antibody chain are typically at least 80 percent encoded by human germline V, J, and, in the case of heavy chains, D, gene segments; frequently at least 85 percent of the variable regions are encoded by human germline sequences present on the transgene; often 90 or 95 percent or more of the variable region sequences are encoded by human germline sequences present on the transgene. However, since non-germline sequences are introduced by somatic mutation and VJ and VDJ joining, the human sequence antibodies will frequently have some variable region sequences (and less frequently constant region sequences) which are not encoded by human V, D, or J gene segments as found in the human transgene(s) in the germline of the mice. Typically, such non-germline sequences (or individual nucleotide positions) will cluster in or near CDRs, or in regions where somatic mutations are known to cluster.

Human antibodies which bind to the predetermined antigen can result from isotype switching, such that human antibodies comprising a human sequence γ chain (such as γ1, γ2a, γ2B, or γ3) and a human sequence light chain (such as kappa) are produced. Such isotype-switched human antibodies often contain one or more somatic mutation(s), typically in the variable region and often in or within about 10 residues of a CDR) as a result of affinity maturation and selection of B cells by antigen, particularly subsequent to secondary (or subsequent) antigen challenge. These high affinity human antibodies may have binding affinities ($K_D$) of below $10^{-7}$ M, such as of below $10^{-8}$ M, $10^{-9}$ M or $10^{-10}$ M or even lower.

Another aspect of the invention includes B cells derived from transgenic or transchromosomal nonhuman animals as described herein. The B cells can be used to generate hybridomas expressing human monoclonal antibodies which bind with high affinity (e.g., lower than $10^{-7}$ M) to human CD30. Thus, in another embodiment, the invention provides a hybridoma which produces a human antibody having an affinity ($K_D$) of below $10^{-7}$ M, such as of below $10^{-8}$ M, $10^{-9}$ M or $10^{-10}$ M or even lower when determined by surface plasmon resonance (SPR) technology in a BIACORE 3000 instrument using recombinant human CD30 as the analyte and the antibody as the ligand for binding human CD30, wherein the antibody comprises:

a human sequence light chain composed of (1) a light chain variable region having a polypeptide sequence which is substantially identical to a polypeptide sequence encoded by a human $V_L$ gene segment and a human $J_L$ segment, and (2) a light chain constant region having a polypeptide sequence which is substantially identical to a polypeptide sequence encoded by a human $C_L$ gene segment; and a human sequence heavy chain composed of a (1) a heavy chain variable region having a polypeptide sequence which is substantially identical to a polypeptide sequence encoded by a human $V_H$ gene segment, optionally a D region, and a human $J_H$ segment, and (2) a constant region having a polypeptide sequence which is substantially identical to a polypeptide sequence encoded by a human $C_H$ gene segment.

The development of high affinity human monoclonal antibodies against CD30 can be facilitated by a method for expanding the repertoire of human variable region gene segments in a transgenic nonhuman animal having a genome comprising an integrated human immunoglobulin transgene, said method comprising introducing into the genome a V gene transgene comprising V region gene segments which are not present in said integrated human immunoglobulin transgene. Often, the V region transgene is a yeast artificial chromosome comprising a portion of a human $V_H$ or $V_L$ ($V_K$) gene segment array, as may naturally occur in a human genome or as may be spliced together separately by recombinant methods, which may include out-of-order or omitted V gene segments. Often at least five or more functional V gene segments are contained on the YAC. In this variation, it is possible to make a transgenic animal produced by the V repertoire expansion method, wherein the animal expresses an immunoglobulin chain comprising a variable region sequence encoded by a V region gene segment present on the V region transgene and a C region encoded on the human Ig transgene. By means of the V repertoire expansion method, transgenic animals having at least 5 distinct V genes can be generated; as can animals containing at least about 24 V genes or more. Some V gene segments may be non-functional (e.g., pseudogenes and the like); these segments may be retained or may be selectively deleted by recombinant methods available to the skilled artisan, if desired.

Once the mouse germline has been engineered to contain a functional YAC having an expanded V segment repertoire, substantially not present in the human Ig transgene containing the J and C gene segments, the trait can be propagated and bred into other genetic backgrounds, including backgrounds where the functional YAC having an expanded V segment repertoire is bred into a nonhuman animal germline having a different human Ig transgene. Multiple functional YACs having an expanded V segment repertoire may be bred into a germline to work with a human Ig transgene (or multiple human Ig transgenes). Although referred to herein as YAC transgenes, such transgenes when integrated into the genome may substantially lack yeast sequences, such as sequences required for autonomous replication in yeast; such sequences may optionally be removed by genetic engineering (e.g., restriction digestion and pulsed-field gel electrophoresis or other suitable method) after replication in yeast is no longer necessary (i.e., prior to introduction into a mouse ES cell or mouse prozygote). Methods of propagating the trait of human sequence immunoglobulin expression, include breeding a transgenic animal having the human Ig transgene(s), and optionally also having a functional YAC having an expanded V segment repertoire. Both $V_H$ and $V_L$ gene segments may be present on the YAC. The transgenic animal may be bred into any background desired by the practitioner, including backgrounds harboring other human transgenes, including human Ig transgenes and/or transgenes encoding other human lymphocyte proteins. The invention also provides a high affinity human sequence immunoglobulin produced by a transgenic mouse having an expanded V region repertoire YAC transgene. Although the foregoing describes a preferred embodiment of the transgenic animal used to produce the human monoclonal antibodies of the invention, other embodiments are contemplated which have been classified in four categories:

I. Transgenic animals containing an unrearranged heavy and rearranged light immunoglobulin transgene;

II. Transgenic animals containing an unrearranged heavy and unrearranged light immunoglobulin transgene;

III. Transgenic animals containing a rearranged heavy and an unrearranged light immunoglobulin transgene; and IV. Transgenic animals containing a rearranged heavy and rearranged light immunoglobulin transgene.

Of these categories of transgenic animal, the order of preference is as follows II>I>III>IV where the endogenous light chain genes (or at least the K gene) have been knocked out by homologous recombination (or other method) and I>II>III>IV where the endogenous light chain genes have not been knocked out and must be dominated by allelic exclusion.

III. Bispecific/Multispecific Molecules Which Bind to CD30

In yet another embodiment of the invention, human monoclonal antibodies to CD30, or antigen-binding portions thereof, can be derivatized or linked to another functional molecule, e.g., another peptide or protein (e.g., an Fab' fragment) to generate a bispecific or multispecific molecule which binds to multiple binding sites or target epitopes. For example, an antibody or antigen-binding portion of the invention can be functionally linked (e.g., by chemical coupling, genetic fusion, noncovalent association or otherwise) to one or more other binding molecules, such as another antibody, antibody fragment, peptide or binding mimetic.

Accordingly, the present invention includes bispecific and multispecific molecules comprising at least one first binding specificity for CD30 and a second binding specificity for a second target epitope. In a particular embodiment of the invention, the second target epitope is an Fc receptor, e.g., human FcγRI (CD64) or a human Fcα receptor (CD89). Therefore, the invention includes bispecific and multispecific molecules capable of binding both to FcγR, FcαR or Fc□R expressing effector cells (e.g., monocytes, macrophages or polymorphonuclear cells (PMNs)), and to target cells expressing CD30. These bispecific and multispecific molecules target CD30 expressing cells to effector cell and, like the human monoclonal antibodies of the invention, trigger Fc receptor-mediated effector cell activities, such as phagocytosis of a CD30 expressing cells, antibody dependent cell-mediated cytotoxicity (ADCC), cytokine release, or generation of superoxide anion.

Bispecific and multispecific molecules of the invention can further include a third binding specificity, in addition to an anti-Fc binding specificity and an anti-CD30 binding specificity. In one embodiment, the third binding specificity is an anti-enhancement factor (EF) portion, e.g., a molecule which binds to a surface protein involved in cytotoxic activity and thereby increases the immune response against the target cell. The "anti-enhancement factor portion" can be an antibody, functional antibody fragment or a ligand that binds to a given molecule, e.g., an antigen or a receptor, and thereby results in an enhancement of the effect of the binding determinants for the $F_c$ receptor or target cell antigen. The "anti-enhancement factor portion" can bind an $F_c$ receptor or a target cell antigen. Alternatively, the anti-enhancement factor portion can bind to an entity that is different from the entity to which the first and second binding specificities bind. For example, the anti-enhancement factor portion can bind a cytotoxic T-cell (e.g. via CD2, CD3, CD8, CD28, CD4, CD40, ICAM-1 or other immune cell that results in an increased immune response against the target cell).

In one embodiment, the bispecific and multispecific molecules of the invention comprise as a binding specificity at least one antibody, or an antibody fragment thereof, including, e.g., an Fab, Fab', F(ab')$_2$, Fv, or a single chain Fv. The antibody may also be a light chain or heavy chain dimer, or any minimal fragment thereof such as a Fv or a single chain construct as described in Ladner et al. U.S. Pat. No.4,946,778, issued Aug. 7, 1990, the contents of which is expressly incorporated by reference.

In one embodiment bispecific and multispecific molecules of the invention comprise a binding specificity for an FcγR or an FcαR present on the surface of an effector cell, and a second binding specificity for a target cell antigen, e.g., CD30.

In one embodiment, the binding specificity for an Fc receptor is provided by a human monoclonal antibody, the binding of which is not blocked by human immunoglobulin G (IgG). As used herein, the term "IgG receptor" refers to any of the eight γ-chain genes located on chromosome 1. These genes encode a total of twelve transmembrane or soluble receptor isoforms which are grouped into three Fcγ receptor classes: FcγRI (CD64), Fcγ RII(CD32), and FcγRIII (CD 16). In one preferred embodiment, the Fcγ receptor a human high affinity FcγRI. The human FcγRI is a 72 kDa molecule, which shows high affinity for monomeric IgG ($10^8$-$10^9 M^{-1}$).

The production and characterization of these preferred monoclonal antibodies are described by Fanger et al. in PCT application WO 88/00052 and in U.S. Pat. No. 4,954,617, the teachings of which are fully incorporated by reference herein. These antibodies bind to an epitope of FcγRI, FcγRII or FcγRIII at a site which is distinct from the Fcγ binding site of the receptor and, thus, their binding is not blocked substantially by physiological levels of IgG. Specific anti-FcγRI antibodies useful in this invention are MAb 22, MAb 32, MAb 44, MAb 62 and MAb 197. The hybridoma producing MAb 32 is available from the American Type Culture Collection, ATCC Accession No. HB9469. Anti-FcγRI MAb 22, F(ab')$_2$ fragments of MAb 22, and can be obtained from Medarex, Inc. (Annandale, N.J.). In other embodiments, the anti-Fcγ receptor antibody is a humanized form of monoclonal antibody 22 (H22). The production and characterization of the H22 antibody is described in Graziano, R. F. et al. (1995) J. Immunol 155 (10): 4996-5002 and PCT/US93/10384. The H22 antibody producing cell line was deposited at the American Type Culture Collection on Nov. 4, 1992 under the designation HA022CL1 and has the accession no. CRL 11177.

In still other preferred embodiments, the binding specificity for an Fc receptor is provided by an antibody that binds to a human IgA receptor, e.g., an Fc-alpha receptor (Fcα RI(CD89)), the binding of which is preferably not blocked by human immunoglobulin A (IgA). The term "IgA receptor" is intended to include the gene product of one α-gene (Fcα RI) located on chromosome 19. This gene is known to encode several alternatively spliced transmembrane isoforms of 55 to 110 kDa. FcαRI (CD89) is constitutively expressed on monocytes/macrophages, eosinophilic and neutrophilic granulocytes, but not on non-effector cell populations. FcαRI has medium affinity ($\approx 5 \times 10^7$ $M^{-1}$) for both IgA1 and IgA2, which is increased upon exposure to cytokines such as G-CSF or GM-CSF (Morton, H. C. et at. (1996) *Critical Reviews in Immunology* 16:423-440). Four FcαRI-specific monoclonal antibodies, identified as A3, A59, A62 and A77, which bind FcαRI outside the IgA ligand binding domain, have been described (Monteiro, R. C. et al., 1992, *J. Immunol.* 148:1764). FcαRI and FcγRI are preferred trigger receptors for use in the invention because they are (1) expressed primarily on immune effector cells, e.g., monocytes, PMNs, macrophages and dendritic cells; (2) expressed at high levels (e.g., 5,000-100,000 per cell); (3) mediators of cytotoxic activities (e.g., ADCC, phagocytosis); (4) mediate enhanced antigen presentation of antigens, including self-antigens, targeted to them.

In other embodiments, bispecific and multispecific molecules of the invention further comprise a binding specificity which recognizes, e.g., binds to, a target cell antigen, e.g., CD30. In a preferred embodiment, the binding specificity is provided by a human monoclonal antibody of the present invention.

An "effector cell specific antibody" as used herein refers to an antibody or functional antibody fragment that binds the Fc receptor of effector cells. Preferred antibodies for use in the subject invention bind the Fc receptor of effector cells at a site which is not bound by endogenous immunoglobulin.

As used herein, the term "effector cell" refers to an immune cell which is involved in the effector phase of an immune response, as opposed to the cognitive and activation phases of an immune response. Exemplary immune cells include a cell of a myeloid or lymphoid origin, e.g., lymphocytes (e.g., B cells and T cells including cytolytic T cells (CTLs)), killer cells, natural killer cells, macrophages, monocytes, eosinophils, neutrophils, polymorphonuclear cells, granulocytes, mast cells, and basophils. Some effector cells express specific Fc receptors and carry out specific immune functions. In preferred embodiments, an effector cell is capable of inducing antibody-dependent cell-mediated cytotoxicity (ADCC), e.g., a neutrophil capable of inducing ADCC. For example, monocytes, macrophages, which express FcR are involved in specific killing of target cells and presenting antigens to other components of the immune system, or binding to cells that present antigens. In other embodiments, an effector cell can phagocytose a target antigen, target cell, or microorganism. The expression of a particular FcR on an effector cell can be regulated by humoral factors such as cytokines. For example, expression of FcγRI has been found to be up-regulated by interferon gamma (IFN-γ). This enhanced expression increases the cytotoxic activity of FcγRI-bearing cells against targets. An effector cell can phagocytose or lyse a target antigen or a target cell.

"Target cell" shall mean any undesirable cell in a subject (e.g., a human or animal) that can be targeted by a composition (e.g., a human monoclonal antibody, a bispecific or a multispecific molecule) of the invention. In preferred embodiments, the target cell is a cell expressing or overexpressing CD30. Cells expressing CD30 typically include tumor cells, such as bladder, breast, colon, kidney, ovarian, prostate, renal cell, squamous cell, lung (non-small cell), and head and neck tumor cells. Other target cells include synovial fibroblast cells.

While human monoclonal antibodies are preferred, other antibodies which can be employed in the bispecific or multispecific molecules of the invention are murine, chimeric and humanized monoclonal antibodies.

Chimeric mouse-human monoclonal antibodies (i.e., chimeric antibodies) can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted. (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al U.S. Pat. No. 4,816,567; Cabilly et al., European Patent Application 125, 023; Better et al. (1988 Science 240:1041-1043); Liu et al. (1987) PNAS 84:3439-3443; Liu et al., 1987, J. Immunol. 139:3521-3526; Sun et al. (1987) PNAS 84:214-218; Nishimura et al., 1987, Canc. Res. 47:999-1005; Wood et al (1985) Nature 314:446-449; and Shaw et al., 1988, J. Natl Cancer Inst. 80:1553-1559).

The chimeric antibody can be further humanized by replacing sequences of the Fv variable region which are not directly involved in antigen binding with equivalent sequences from human Fv variable regions. General reviews of humanized chimeric antibodies are provided by Morrison, S. L., 1985, Science 229:1202-1207 and by Oi et al., 1986, BioTechniques 4:214. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from 7E3, an anti-GPII$_b$III$_a$ antibody producing hybridoma. The recombinant DNA encoding the chimeric antibody, or fragment thereof, can then be cloned into an appropriate expression vector. Suitable humanized antibodies can alternatively be produced by CDR substitution U.S. Pat. 5,225,539; Jones et al. 1986 Nature 321:552-525; Verhoeyan et al. 1988 Science 239: 1534; and Beidler et al. 1988 J. Immunol. 141 :4053-4060.

All of the CDRs of a particular human antibody may be replaced with at least a portion of a non-human CDR or only some of the CDRs may be replaced with non-human CDRs. It is only necessary to replace the number of CDRs required for binding of the humanized antibody to the Fc receptor.

An antibody can be humanized by any method, which is capable of replacing at least a portion of a CDR of a human antibody with a CDR derived from a non-human antibody. Winter describes a method which may be used to prepare the humanized antibodies of the present invention (UK Patent Application GB 2188638A, filed on Mar. 26, 1987), the contents of which is expressly incorporated by reference. The human CDRs may be replaced with non-human CDRs-using oligonucleotide site-directed mutagenesis as described in International Application WO 94/10332 entitled, *Humanized Antibodies to Fc Receptors for Immunoglobulin G on Human Mononuclear Phagocytes.*

Also within the scope of the invention are chimeric and humanized antibodies in which specific amino acids have been substituted, deleted or added. In particular, preferred humanized antibodies have amino acid substitutions in the framework region, such as to improve binding to the antigen. For example, in a humanized antibody having mouse CDRs, amino acids located in the human framework region can be replaced with the amino acids located at the corresponding positions in the mouse antibody. Such substitutions are known to improve binding of humanized antibodies to the antigen in some instances. Antibodies in which amino acids have been added, deleted, or substituted are referred to herein as modified antibodies or altered antibodies.

The term modified antibody is also intended to include antibodies, such as monoclonal antibodies, chimeric antibodies, and humanized antibodies which have been modified by, e.g., deleting, adding, or substituting portions of the antibody. For example, an antibody can be modified by deleting the constant region and replacing it with a constant region meant to increase half-life, e.g., serum half-life, stability or affinity of the antibody. Any modification is within the scope of the invention so long as the bispecific and multispecific molecule has at least one antigen binding region specific for an FcγR and triggers at least one effector function.

Bispecific and multispecific molecules of the present invention can be made using chemical techniques (see e.g., D. M. Kranz et al. (1981) Proc. Natl. Acad. Sci. USA 78:5807), "polydoma" techniques (See U.S. Patent 4,474, 893, to Reading), or recombinant DNA techniques.

In particular, bispecific and multispecific molecules of the present invention can be prepared by conjugating the constituent binding specificities, e.g., the anti-FcR and anti-CD30 binding specificities, using methods known in the art and described in the examples provided-herein. For example, each binding specificity of the bispecific and multispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-1-carboxylate (sulfo-SMCC) (see e.g., Karpovsky et al. (1984) *J. Exp. Med.* 160:1686; Liu, M A et al. (1985) Proc. Natl. Acad. Sci. USA 82:8648). Other methods include those described by Paulus (Behring Ins. Mitt. (1985) No. 78, 118-132); Brennan et al. (Science (1985) 229:81-83), and Glennie et al. (J. Immunol. (1987) 139: 2367-2375). Preferred conjugating agents are SATA and sulfo-SMCC, both available from Pierce Chemical Co. (Rockford, Ill.).

When the binding specificities are antibodies (e.g., two humanized antibodies), they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific and multispecific molecule is a MAb ×MAb, MAb ×Fab, Fab ×F(ab')$_2$ or ligand×Fab fusion protein. A bispecific and multispecific molecule of the invention, e.g., a bispecific molecule can be a single chain molecule, such as a single chain bispecific antibody, a single chain bispecific molecule comprising one single chain antibody and a binding determinant, or a single chain bispecific molecule comprising two binding determinants. Bispecific and multispecific molecules can also be single chain molecules or may comprise at least two single chain molecules. Methods for preparing bi- and multspecific molecules are described for example in U.S. Pat. Nos. 5,260,203; 5,455,030; 4,881,175; 5,132,405; 5,091,513; 5,476,786; 5,013,653; 5,258,498; and 5,482,858.

Binding of the bispecific and multispecific molecules to their specific targets can be confirmed by enzyme-linked immunosorbent assay (ELISA), a radioimmunoassay (RIA), FACS analysis, a bioassay (e.g., growth inhibition), or a Western Blot Assay. Each of these assays generally detects the presence of protein-antibody complexes of particular interest by employing a labeled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a γ counter or a scintillation counter or by autoradiography.

IV. Immunoconjugates

In another aspect, the present invention features a human anti-CD30 monoclonal antibody, or a fragment thereof, conjugated to a therapeutic moiety, such as a cytotoxin, a drug (e.g., an immunosuppressant) or a radiotoxin. Such conjugates are referred to herein as "immunoconjugates". Immunoconjugates which include one or more cytotoxins are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin didne, mitoxantrone, mithramycin, actinomycin D, 1-dehydrotestosterone, glucocorticoids, procaine, tetracaine, lidocaine, propranolol, and puromycin and analogs or homologs thereof.

Suitable therapeutic agents for forming immunoconjugates of the invention include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincnrstine and vinblastine). In a preferred embodiment, the therapeutic agent is a cytotoxic agent or a radiotoxic agent. In another embodiment, the therapeutic agent is an immunosuppressant. In yet another embodiment, the therapeutic agent is GM-CSF. In a preferred embodiment, the therapeutic agent is doxorubicin (adriamycin), cisplatin bleomycin sulfate, carmustine, chlorambucil, cyclophosphamide hydroxyurea or ricin A.

Antibodies of the present invention also can be conjugated to a radiotoxin, e.g., radioactive iodine, to generate cytotoxic radiopharmaceuticals for treating a CD30-related disorder, such as a cancer. The antibody conjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

V. Pharmaceutical Compositions

In another aspect, the present invention provides a composition, e.g., a pharmaceutical composition, containing one or a combination of human monoclonal antibodies, or antigen-binding portion(s) thereof, of the present invention, formulated together with a pharmaceutically acceptable carrier. In a preferred embodiment, the compositions include a combination of multiple (e.g., two or more) isolated human antibodies or antigen-binding portions thereof of the invention. Preferably, each of the antibodies or antigen-binding portions thereof of the composition binds to a distinct, pre-selected epitope of CD30.

Pharmaceutical compositions of the invention also can be administered in combination therapy, i.e., combined with other agents. For example, the combination therapy can include a composition of the present invention with at least one anti-inflammatory agent or at least one immunosuppressive agent. Such therapeutic agents include, among others, steroidal and nonsteroidal anti-inflammatory drugs (NSAIDS), e.g., aspirin and other salicylates, such as ibuprofen (Motrin, Advil), naproxen (Naprosyn), sulindac (Clinoril), diclofenac (Voltaren), piroxicam (Feldene), ketoprofen (Orudis), diflunisal (Dolobid), nabumetone (Relafen), etodolac (Lodine), oxaprozin (Daypro), indomethacin (Indocin), and aspirin in high doses.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, bispecific and multispecific molecule, may be coated in a material to protect the compound from the action of acids and other natural conditions that may inactivate the compound.

A "pharmaceutically acceptable salt" refers to a salt that retains the desired biological activity of the parent compound and does not impart any undesired toxicological effects (see e.g., Berge, S. M., et al. (1977) J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A composition of the present invention can be administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al. (1984) *J. Neuroimmunol.* 7:27).

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

For the therapeutic compositions, formulations of the present invention include those suitable for oral, nasal, topical (including buccal and sublingual), rectal, vaginal and/or parenteral administration. The formulations may conveniently be presented in unit dosage form and may be prepared by any methods known in the art of pharmacy. The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred per cent, this amount will range from about 0.01 per cent to about ninety-nine percent of active ingredient, preferably from about 0.1 per cent to about 70 per cent, most preferably from about 1 per cent to about 30 per cent.

Formulations of the present invention which are suitable for vaginal administration also include pessaries, tampons, creams, gels, pastes, foams or spray formulations containing such carriers as are known in the art to be appropriate. Dosage forms for the topical or transdermal administration of compositions of this invention include powders, sprays, ointments, pastes, creams, lotions, gels, solutions, patches and inhalants.

The active compound may be mixed under sterile conditions with a pharmaceutically acceptable carrier, and with any preservatives, buffers, or propellants which may be required.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

When the compounds of the present invention are administered as pharmaceuticals, to humans and animals, they can be given alone or as a pharmaceutical composition containing, for example, 0.01 to 99.5% (more preferably, 0.1 to 90%) of active ingredient in combination with a pharmaceutically acceptable carrier.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. In general, a suitable daily dose of a compositions of the invention will be that amount of the compound which is the lowest dose effective to produce a therapeutic effect. Such an effective dose will generally depend upon the factors described above. It is preferred that administration be intravenous, intramuscular, intraperitoneal, or subcutaneous, preferably administered proximal to the site of the target. If desired, the effective daily dose of a therapeutic compositions may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical formulation (composition).

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S.

Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the human monoclonal antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134), different species of which may comprise the formulations of the inventions, as well as components of the invented molecules; p120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994) *Immunomethods* 4:273. In one embodiment of the invention, the therapeutic compounds of the invention are formulated in liposomes; in a more preferred embodiment, the liposomes include a targeting moiety. In a most preferred embodiment, the therapeutic compounds in the liposomes are delivered by bolus injection to a site proximal to the desired area, e.g., the site of inflammation or infection, or the site of a tumor. The composition must be fluid to the extent that easy syringability exists. It must be stable under the conditions of manufacture and storage and must be preserved against the contaminating action of microorganisms such as bacteria and fungi.

A "therapeutically effective dosage" preferably inhibits cell growth or tumor growth by at least about 20%, more preferably by at least about 40%, even more preferably by at least about 60%, and still more preferably by at least about 80% relative to untreated subjects. The ability of a compound to inhibit cancer can be evaluated in an animal model system predictive of efficacy in human tumors. Alternatively, this property of a composition can be evaluated by examining the ability of the compound to inhibit, such inhibition in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

The composition must be sterile and fluid to the extent that the composition is deliverable by syringe. In addition to water, the carrier can be an isotonic buffered saline solution, ethanol, polyol (for example, glycerol, propylene glycol, and liquid polyetheylene glycol, and the like), and suitable mixtures thereof. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

When the active compound is suitably protected, as described above, the compound may be orally administered, for example, with an inert diluent or an assimilable edible carrier.

VI. Uses and Methods of the Invention

The human antibodies, antibody compositions and methods of the present invention have numerous in vitro and in vivo diagnostic and therapeutic utilities involving the diagnosis and treatment of CD30 mediated disorders. For example, these molecules can be administered to cells in culture, e.g. in vitro or ex vivo, or to human subjects, e.g., in vivo, to treat, prevent and to diagnose a variety of disorders. As used herein, the term "subject" is intended to include human and non-human animals. Preferred subjects include human patients having disorders mediated by CD30 activity.

For example, the human antibodies, antibody compositions and methods of the present invention can be used to treat a subject with a tumorigenic disorder, e.g., a disorder characterized by the presence of tumor cells expressing CD30 including, for example, Hodgkin's disease, anaplastic large cell lymphoma (ALCL), adult T-cell lymphoma. (ATL), angioimmunoblastic lymphadenopathy (AILD)-like T cell lymphoma, HIV associated body cavity based lymphomas, Embryonal Carcinomas, undifferentiated carcinomas of the rhino-pharynx (e.g., Schmincke's tumor), Castleman's disease, Kaposi's Sarcoma and other T-cell or B-cell lymphomas. The human antibodies, antibody compositions and the methods of the present invention can also be used to treat a subject with other disorders, e.g., autoimmune diseases, including, for example, Rheumatoid arthritis, Systemic Lupus Erythematosus, Systemic Sclerosis, Atopic Dermatitis, Graves' disease, Hashimoto's thyroiditis, Wegner's granulomatosis, Omen's syndrome, chronic renal failure, acute infectious mononucleosis, HIV and herpes virus associated diseases.

In one embodiment, the antibodies (e.g., human monoclonal antibodies, multispecific and bispecific molecules and compositions) of the invention can be used to detect levels of CD30, or levels of cells which contain CD30 on their membrane surface, which levels can then be linked to certain disease symptoms. Alternatively, the antibodies can be used to inhibit or block CD30 function which, in turn, can be linked to the prevention or amelioration of certain disease symptoms, thereby implicating CD30 as a mediator of the disease. This can be achieved by contacting a sample and a control sample with the anti-CD30 antibody under conditions that allow for the formation of a complex between the antibody and CD30. Any complexes formed between the antibody and CD30 are detected and compared in the sample and the control.

In another embodiment, the antibodies (e.g., human antibodies, multispecific and bispecific molecules and compositions) of the invention can be initially tested for binding activity associated with therapeutic or diagnostic use in vitro. For example, compositions of the invention can be tested using the ELISA and flow cytometric assays described in the Examples below. Moreover, the activity of these molecules in triggering at least one effector-mediated effector cell activity, including inhibiting the growth of and/or killing of cells expressing CD30 can be assayed. Protocols for assaying for effector cell-mediated ADCC or phagocytosis are described in the Examples below.

The antibodies (e.g., human antibodies, multispecific and bispecific molecules and compositions) of the invention have additional utility in therapy and diagnosis of CD30-related diseases. For example, the human monoclonal antibodies, the multispecific or bispecific molecules and the immunoconjugates can be used to elicit in vivo or in vitro one or more of the following biological activities: to inhibit the growth of and/or kill a cell expressing CD30; to mediate phagocytosis or ADCC of a cell expressing CD30 in the presence of human effector cells; to inhibit shedding of soluble CD30, to block CD30 ligand binding to CD30, to inhibit IL-4 expression or to mediate expression of the Th2 phenotype, e.g., at low dosages.

In another embodiment, the antibodies (e.g., human antibodies, multispecific and bispecific molecules and compositions) of the present invention are unable to induce complement-mediated lysis of cells and, therefore, has fewer side effects in triggering complement-activated afflictions, e.g., acne. The primary cause of acne is an alteration in the pattern of keratinization within the follicle that produce sebum. Since keratinocytes express CD30, interference with CD30 signaling processes in the skin can alter the growth and differentiation of the keratinocytes in the follicles which results in the formation of acne. Direct immunofluorescent studies have shown that in early non-inflamed and inflamed acne lesions there is activation of the classical and alternative complement pathways.

In a particular embodiment, the antibodies (e.g., human antibodies, multispecific and bispecific molecules and compositions) are used in vivo to treat, prevent or diagnose a variety of CD30-related diseases. Examples of CD30-related diseases include, among others, cancer, Hodgkin's disease, non-Hodgkin's lymphoma, anaplastic large cell lymphoma (ALCL), adult T-cell lymphoma. (ATL), angioimmunoblastic lymphadenopathy (AILD)-like T cell lymphoma, HIV associated body cavity based lymphomas, Embryonal Carcinomas, undifferentiated carcinomas of the rhino-pharynx (e.g., Schmincke's tumor), Castleman's disease, Kaposi's Sarcoma and other T-cell or B-cell lymphomas. Other CD30 mediated diseases include among others, autoimmune diseases, Rheumatoid arthritis, Systemic Lupus Erythematosus, Systemic Sclerosis, Atopic Dermatitis, Graves' disease, Hashimoto's thyroiditis, Wegner's granulomatosis, Omen's syndrome, chronic renal failure, acute infectious mononucleosis, HIV and herpes virus associated diseases.

In a particular embodiment, the antibodies (e.g., human monoclonal antibodies, multispecific and bispecific molecules and compositions) of the invention are used to treat or to prevent Hodgkin's disease (HD), as the antibodies limit the role that CD30 plays in the progression of HD and other tumorigenic diseases. Hodgkin's disease is a type of lymnphoma. Lymphomas are cancers that develop in the lymph system, part of the body's immune system. Because there is lymph tissue in many parts of the body, HD can start in almost any part of the body. The cancer can spread to almost any organ or tissue in the body, including the liver, bone marrow (the spongy tissue inside the large bones of the body that makes blood cells), and the spleen. Elevated expression of CD30 in Hodgkin's and Reed-Sternberg cells has been reported to correlate with the differential diagnosis of HD.

Accordingly, CD30 inhibiting antibodies of the invention can be used to prevent or block the effects of CD30 which lead to HD and, thus, can be used to prevent or treat this disease.

Human antibodies (e.g., human monoclonal antibodies, multispecific and bispecific molecules) of the present invention also can be used to block or inhibit other effects of CD30. For example, it is known that CD30 is also regularly expressed by a variety of non-Hodgkin's lymphoma subtypes. Accordingly, yet another use for the antibodies of the invention includes the prevention or treatment of diseases involving non-Hodgkin's lymphomas. These diseases include Burkitt's lymphoma, anaplastic large-cell lymphomas (ALCL), cutaneous T-cell lymphomas, nodular small cleaved-cell lymphomas, lymphocytic lymphomas, peripheral T-cell lymphomas, Lennert's lymphomas, immunoblastic lymphomas, T-cell leukemia/lymphomas (ATLL), adult T-cell leukemia (T-ALL), and entroblastic/centrocytic (cb/cc) follicular lymphomas cancers.

In another particular embodiment, human antibodies (e.g., human monoclonal antibodies, multispecific and bispecific molecules and compositions) of the present invention can be used to block or inhibit yet other effects of CD30. For example, it is also known that soluble CD30 is regularly shed from the surface of cells expressing CD30. Elevated sCD30 levels have been reported in the serum of patients with a variety of tumorigenic and autoimmune disorders. Accordingly, yet another use for the antibodies of the invention includes the prevention or treatment of diseases involving blocking or inhibiting of shedding of sCD30. Such diseases include, but are not limited to, Rheumatoid arthritis, Systemic Lupus Erythematosus, Systemic Sclerosis, Atopic Dermatitis, Graves' disease, Hashimoto's thyroiditis, Wegner's granulomatosis, and Omen's syndrome.

Suitable routes of administering the antibody compositions (e.g., human monoclonal antibodies, multispecific and bispecific molecules and immunoconjugates ) of the invention in vivo and in vitro are well known in the art and can be selected by those of ordinary skill. For example, the antibody compositions can be administered by injection (e.g., intravenous or subcutaneous). Suitable dosages of the molecules used will depend on the age and weight of the subject and the concentration and/or formulation of the antibody composition.

As previously described, human anti-CD30 antibodies of the invention can be co-administered with one or other more therapeutic agents, e.g., an cytotoxic agent, a radiotoxic agent or an immunosuppressive agent. The antibody can be linked to the agent (as an immunocomplex) or can be administered separate from the agent. In the latter case (separate administration), the antibody can be administered before, after or concurrently with the agent or can be co-administered with other known therapies, e.g., an anti-cancer therapy, e.g., radiation. Such therapeutic agents include, among others, anti-neoplastic agents such as doxorubicin (adriamycin), cisplatin bleomycin sulfate, carmustine, chlorambucil, and cyclophosphamide hydroxyurea which, by themselves, are only effective at levels which are toxic or subtoxic to a patient. Cisplatin is intravenously administered as a 100 mg/m$^2$ dose once every four weeks and adriamycin is intravenously administered as a 60-75 mg/m$^2$ dose once every 21 days. Co-administration of the human anti-CD30 antibodies, or antigen binding fragments thereof, of the present invention with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the antibody.

Target-specific effector cells, e.g., effector cells linked to compositions (e.g., human antibodies, multispecific and bispecific molecules) of the invention can also be used as therapeutic agents. Effector cells for targeting can be human leukocytes such as macrophages, neutrophils or monocytes. Other cells include eosinophils, natural killer cells and other IgG- or IgA-receptor bearing cells. If desired, effector cells can be obtained from the subject to be treated. The target-specific effector cells, can be administered as a suspension of cells in a physiologically acceptable solution. The number of cells administered can be in the order of $10^8$-$10^9$ but will vary depending on the therapeutic purpose. In general, the amount will be sufficient to obtain localization at the target cell, e.g., a tumor cell expressing CD30, and to effect cell killing by, e.g., phagocytosis. Routes of administration can also vary.

Therapy with target-specific effector cells can be performed in conjunction with other techniques for removal of targeted cells. For example, anti-tumor therapy using the compositions (e.g., human antibodies, multispecific and bispecific molecules) of the invention and/or effector cells armed with these compositions can be used in conjunction with chemotherapy. Additionally, combination immunotherapy may be used to direct two distinct cytotoxic effector populations toward tumor cell rejection. For example, anti-CD30 antibodies linked to anti-Fc-gamma RI or anti-CD3 may be used in conjunction with IgG- or IgA-receptor specific binding agents.

Bispecific and multispecific molecules of the invention can also be used to modulate FcγR or FcαR levels on effector cells, such as by capping and elimination of receptors on the cell surface. Mixtures of anti-Fc receptors can also be used for this purpose.

The compositions (e.g., human antibodies, multispecific and bispecific molecules and immunoconjugates) of the invention which have complement binding sites, such as portions from IgG1, -2, or -3 or IgM which bind complement, can also be used in the presence of complement. In one embodiment, ex vivo treatment of a population of cells comprising target cells with a binding agent of the invention and appropriate effector cells can be supplemented by the addition of complement or serum containing complement. Phagocytosis of target cells coated with a binding agent of the invention can be improved by binding of complement proteins. In another embodiment target cells coated with the compositions (e.g., human antibodies, multispecific and bispecific molecules) of the invention can also be lysed by complement. In yet another embodiment, the compositions of the invention do not activate complement.

The compositions (e.g., human antibodies, multispecific and bispecific molecules and immunoconjugates) of the invention can also be administered together with complement. Accordingly, within the scope of the invention are compositions comprising human antibodies, multispecific or bispecific molecules and serum or complement. These compositions are advantageous in that the complement is located in close proximity to the human antibodies, multispecific or bispecific molecules. Alternatively, the human antibodies, multispecific or bispecific molecules of the invention and the complement or serum can be administered separately.

Also within the scope of the present invention are kits comprising the antibody compositions of the invention (e.g., human antibodies and immunoconjugates) and instructions for use. The kit can further contain one ore more additional reagents, such as an immunosuppressive reagent, a cytotoxic agent or a radiotoxic agent, or one or more additional human antibodies of the invention (e.g., a human antibody having a complementary activity which binds to an epitope in the CD30 antigen distinct from the first human antibody).

Accordingly, patients treated with antibody compositions of the invention can be additionally administered (prior to, simultaneously with, or following administration of a human antibody of the invention) with another therapeutic agent, such as a cytotoxic or radiotoxic agent, which enhances or augments the therapeutic effect of the human antibodies.

In other embodiments, the subject can be additionally treated with an agent that modulates, e.g., enhances or inhibits, the expression or activity of Fcγ or Fcα receptors by, for example, treating the subject with a cytokine. Preferred cytokines for administration during treatment with the multispecific molecule include of granulocyte colony-stimulating factor (G-CSF), granulocyte- macrophage colony-stimulating factor (GM-CSF), interferon-γ (IFN-γ), and tumor necrosis factor (TNF).

In another embodiment, the subject can be additionally treated with a lymphokine preparation. Cancer cells which do not highly express CD30 can be induced to do so using lymphokine preparations. Lymphokine preparations can cause a more homogeneous expression of CD30s among cells of a tumor which can lead to a more effective therapy. Lymphokine preparations suitable for administration include interferon-gamma, tumor necrosis factor, and combinations thereof. These can be administered intravenously. Suitable dosages of lymphokine are 10,000 to 1,000,000 units/patient.

The compositions (e.g., human antibodies, multispecific and bispecific molecules) of the invention can also be used to target cells expressing FcγR or CD30, for example for labeling such cells. For such use, the binding agent can be linked to a molecule that can be detected. Thus, the invention provides methods for localizing ex vivo or in vitro cells expressing Fc receptors, such as FcγR, or CD30. The detectable label can be, e.g., a radioisotope, a fluorescent compound, an enzyme, or an enzyme co-factor.

In a particular embodiment, the invention provides methods for detecting the presence of CD30 antigen in a sample, or measuring the amount of CD30 antigen, comprising contacting the sample, and a control sample, with a human monoclonal antibody, or an antigen binding portion thereof, which specifically binds to CD30, under conditions that allow for formation of a complex between the antibody or portion thereof and CD30. The formation of a complex is then detected, wherein a difference complex formation between the sample compared to the control sample is indicative the presence of CD30 antigen in the sample.

In other embodiments, the invention provides methods for treating an CD30 mediated disorder in a subject, e.g., Hodgkin's disease, adult T-cell lymphoma, infectious mononucleosis, and Systemic Lupus Erythematosus, by administering to the subject the human antibodies described above. Such antibodies and derivatives thereof are used to inhibit CD30 induced activities associated with certain disorders, e.g., proliferation and differentiation. Other CD30 induced activities which can be inhibited by the antibodies of the present invention include increased production of sCD30, increased expression of IL-4 and increased production of the Th2 phenotype. By contacting the antibody with CD30 (e.g., by administering the antibody to a subject), the ability of CD30 to induce such activities is inhibited and, thus, the associated disorder is treated. Preferred antibodies bind to epitopes which are specific to CD30 and, thus, advantageously inhibit CD30 induced activities, but do not interfere with the activity of structurally related surface antigens, such as NGFR, CD27 and CD40.

Accordingly, in another embodiment, the present invention provides a method for treating or preventing a tumorigenic disorder mediated by human CD30, e.g., Hodgkin's disease, non-Hodgkin's lymphoma, anaplastic large cell lymphoma (ALCL), adult T-cell lymphoma. (ATL), angioimmunoblastic lymphadenopathy (AILD)-like T cell lymphoma, HIV associated body cavity based lymphomas, Embryonal Carcinomas, undifferentiated carcinomas of the rhino-pharynx (e.g., Schmincke's tumor), Castleman's disease, Kaposi's Sarcoma and other T-cell or B-cell lymphomas. The method involves administering to a subject a antibody composition of the present invention in an amount effective to treat or prevent the disorder. The antibody composition can be administered alone or along with another therapeutic agent, such as a cytotoxic or a radiotoxic agent which acts in conjunction with or synergistically with the antibody composition to treat or prevent the CD30 mediated disease. In a particularly preferred embodiment, the present invention provides a method for treating Hodgkin's disease. In yet another particularly preferred embodiment, the present invention provides a method for treating ALCL.

In another embodiment, the present invention provides a method for treating or preventing an autoimmune disorder mediated by human CD30, e.g., Rheumatoid arthritis, Systemic Lupus Erythematosus, Systemic Sclerosis, Atopic Dermatitis, Graves' disease, Hashimoto's thyroiditis, Wegner's granulomatosis, Omen's syndrome, chronic renal failure, acute infectious mononucleosis, HIV and herpes virus associated diseases. The method involves administering to a subject a antibody composition of the present invention in an amount effective to treat or prevent the disorder. The antibody composition can be administered alone or along with another therapeutic agent, such as an immunosuppressant which acts in conjunction with or synergistically with the antibody composition to treat or prevent the CD30 mediated disease.

In still another embodiment, the invention provides a method for detecting the presence or quantifying the amount of Fc-expressing cells in vivo or in vitro. The method comprises (i) administering to a subject a composition (e.g., a multi- or bispecific molecule) of the invention or a fragment thereof, conjugated to a detectable marker; (ii) exposing the subject to a means for detecting said detectable marker to identify areas containing Fc-expressing cells.

In yet another embodiment, immunoconjugates of the invention can be used to target compounds (e.g., therapeutic agents, labels, cytotoxins, radiotoxoins immunosuppressants, etc.) to cells which have CD30 bound to their surface (e.g., membrane bound or bound to CD30 receptor) by linking such compounds to the antibody. Thus, the invention also provides methods for localizing ex vivo or in vitro cells expressing CD30 and CD30 receptor, such as Hodgkin's cells or Reed-Sternberg cells (e.g., with a detectable label, such as a radioisotope, a fluorescent compound, an enzyme, or an enzyme co-factor). Alternatively, the immunoconjugates can be used to kill cells which have CD30 bound to their surface (e.g., membrane bound or bound to CD30 receptor) by targeting cytotoxins or radiotoxins to CD30.

The present invention is further illustrated by the following examples which should not be construed as further limiting.

EXAMPLES

Example 1

Generation of CD30-Specific Human Monoclonal Antibodies (HuMabs)

I. Generation of Transgenic (Cmu Targeted) Mice for the Production of Fully Human Monoclonal Antibodies to CD30

Construction of a CMD Targeting Vector

The plasmid pICEmu contains an EcoRI/XhoI fragment of the murine Ig heavy chain locus, spanning the mu gene, that was obtained from a Balb/C genomic lambda phage library (Marcu et al. Cell 22: 187, 1980). This genomic fragment was subcloned into the XhoI/EcoRI sites of the plasmid pICEMI9H (Marsh et al; Gene 32, 481-485, 1984). The heavy chain sequences included in pICEmu extend downstream of the EcoRI site located just 3' of the mu intronic enhancer, to the XhoI site located approximately 1 kb downstream of the last transmembrane exon of the mu gene; however, much of the mu switch repeat region has been deleted by passage in E. coli.

The targeting vector was constructed as follows. A 1.3 kb HindIII/SmaI fragment was excised from pICEmu and subcloned into HindIII/SmaI digested pBluescript (Stratagene, La Jolla, Calif.). This pICEmu fragment extends from the HindIII site located approximately 1 kb 5' of Cmul to the SmaI site located within Cmul . The resulting plasmid was digested with SmaI/SpeI and the approximately 4 kb SmaI/XbaI fragment from pICEmu, extending from the SmaI site in Cmul 3' to the XbaI site located just downstream of the last Cmu exon, was inserted. The resulting plasmid, pTAR1, was linearized at the SmaI site, and a neo expression cassette inserted. This cassette consists of the neo gene under the transcriptional control of the mouse phosphoglycerate kinase (pgk) promoter (XbaI/TaqI fragment; Adra et al. (1987) Gene 60: 65-74) and containing the pgk polyadenylation site (PvuII/HindIII fragment; Boer et al. (1990) Biochemical Genetics 28: 299-308). This cassette was obtained from the plasmid pKJ1 (described by Tybulewicz et al. (1991) Cell 65: 1153-1163) from which the neo cassette was excised as an EcoRI/HindIII fragment and subcloned into EcoRI/HindIII digested pGEM-7Zf (+) to generate pGEM-7 (KJ1). The neo cassette was excised from pGEM-7 (KJ1) by EcoRI/SalI digestion, blunt ended and subcloned into the SmaI site of the plasmid pTAR1, in the opposite orientation of the genomic Cmu sequences. The resulting plasmid was linearized with Not I, and a herpes simplex virus thymidine kinase (tk) cassette was inserted to allow for enrichment of ES clones bearing homologous recombinants, as described by Mansour et al. (1988) Nature 336: 348-352. This cassette consists of the coding sequences of the tk gene bracketed by the mouse pgk promoter and polyadenylation site, as described by Tybulewicz et al. (1991) Cell 65: 1153-1163. The resulting CMD targeting vector contains a total of approximately 5.3 kb of homology to the heavy chain locus and is designed to generate a mutant mu gene into which has been inserted a neo expression cassette in the unique SmaI site of the first Cmu exon. The targeting vector was linearized with PvuI, which cuts within plasmid sequences, prior to electroporation into ES cells.

Generation and Analysis of Targeted ES Cells

AB-1 ES cells (McMahon, A. P. and Bradley, A., (1990) Cell 62: 1073-1085) were grown on mitotically inactive SNL76/7 cell feeder layers (ibid.) essentially as described (Robertson, E. J. (1987) in *Teratocarcinomas and Embryonic Stem Cells: a Practical Approach* (E. J. Robertson, ed.) Oxford: IRL Press, p. 71-112). The linearized CMD targeting vector was electroporated into AB-1 cells by the methods described Hasty et al. (Hasty, P. R. et al. (1991) Nature 350: 243-246). Electroporated cells were plated into 100 mm dishes at a density of $1-2\times 10^6$ cells/dish. After 24 hours, G418 (200 micrograms/ml of active component) and FIAU ($5\times 10^{-7}$M) were added to the medium, and drug-resistant clones were allowed to develop over 8-9 days. Clones were picked, trypsinized, divided into two portions, and further expanded. Half of the cells derived from each clone were then frozen and the other half analyzed for homologous recombination between vector and target sequences.

DNA analysis was carried out by Southern blot hybridization. DNA was isolated from the clones as described Laird et al. (Laird, P. W. et al., (1991) Nucleic Acids Res. 19: 4293). Isolated genomic DNA was digested with SpeI and probed with a 915 bp SacI fragment, probe A (see FIG. 1), which hybridizes to a sequence between the mu intronic enhancer and the mu switch region. Probe A detects a 9.9 kb SpeI fragment from the wild type locus, and a diagnostic 7.6 kb band from a mu locus which has homologously recombined with the CMD targeting vector (the neo expression cassette contains a SpeI site). Of 1132 G418 and FIAU resistant clones screened by Southern blot analysis, 3 displayed the 7.6 kb SpeI band indicative of homologous recombination at the mu locus. These 3 clones were further digested with the enzymes BglI, BstXI, and EcoRI to verify that the vector integrated homologously into the mu gene. When hybridized with probe A, Southern blots of wild type DNA digested with BglI, BstXI, or EcoRI produce fragments of 15.7, 7.3, and 12.5 kb, respectively, whereas the presence of a targeted mu allele is indicated by fragments of 7.7, 6.6, and 14.3 kb, respectively. All 3 positive clones detected by the SpeI digest showed the expected BglI, BstXI, and EcoRI restriction fragments diagnostic of insertion of the neo cassette into the Cmul exon.

Generation of Mice Bearing the Mutated mu Gene

The three targeted ES clones, designated number 264, 272, and 408, were thawed and injected into C57BL/6J blastocysts as described by Bradley (Bradley, A. (1987) in *Teratocarcinomas and Embryonic Stem Cells: a Practical Approach*. (E. J. Robertson, ed.) Oxford: IRL Press, p. 113-151). Injected blastocysts were transferred into the uteri of pseudopregnant females to generate chimeric mice representing a mixture of cells derived from the input ES cells and the host blastocyst. The extent of ES cell contribution to the chimera can be visually estimated by the amount of agouti coat coloration, derived from the ES cell line, on the black C57BL/6J background. Clones 272 and 408 produced only low percentage chimeras (i.e. low percentage of agouti pigmentation) but clone 264 produced high percentage male chimeras. These chimeras were bred with C57BL/6J females and agouti offspring were generated, indicative of germline transmission of the ES cell genome. Screening for the targeted mu gene was carried out by Southern blot analysis of BglI digested DNA from tail biopsies (as described above for analysis of ES cell DNA). Approximately 50% of the agouti offspring showed a hybridizing BglI band of 7.7 kb in addition to the wild type band of 15.7 kb, demonstrating a germline transmission of the targeted mu gene.

Analysis of Transgenic Mice for Functional Inactivation of mu Gene

To determine whether the insertion of the neo cassette into Cmul has inactivated the Ig heavy chain gene, a clone 264 chimera was bred with a mouse homozygous for the JHD mutation, which inactivates heavy chain expression as a result of deletion of the JH gene segments (Chen et al, (1993) Immunol. 5: 647-656). Four agouti offspring were generated. Serum was obtained from these animals at the age of 1 month and assayed by ELISA for the presence of murine IgM. Two of the four offspring were completely lacking IgM (see Table 1). Genotyping of the four animals by Southern blot analysis of DNA from tail biopsies by BglI digestion and hybridization with probe A (see FIG. 1), and by StuI digestion and hybridization with a 475 bp EcoRI/StuI fragment (ibid.) demonstrated that the animals which fail to express serum IgM are those in which one allele of the heavy chain locus carries the JHD mutation, the other allele the Cmul mutation. Mice heterozygous for the JHD mutation display wild type levels of serum Ig. These data demonstrate that the Cmul mutation inactivates expression of the mu gene.

TABLE 1

| Mouse | Serum IgM (micrograms/ml) | Ig H chain genotype |
| --- | --- | --- |
| 42 | <0.002 | CMD/JHD |
| 43 | 196 | +/JHD |
| 44 | <0.002 | CMD/JHD |
| 45 | 174 | +/JHD |
| 129 × BL6 F1 | 153 | +/+ |
| JHD | <0.002 | JHD/JHD |

Table 1 shows the levels of serum IgM, detected by ELISA, for mice carrying both the CMD and JHD mutations (CMD/JHD), for mice heterozygous for the JHD mutation (+/JHD), for wild type (129Sv×C57BL/6J)F1 mice (+/+), and for B cell deficient mice homozygous for the JHD mutation (JHD/JHD).

II. Generation of HCO12 Transgenic Mice

The HCO12 human heavy transgene was generated by coinjection of the 80 kb insert of pHC2 (Taylor et al., 1994, Int. Immunol., 6: 579-591) and the 25 kb insert of pVx6. The plasmid pVx6 was constructed as described below.

An 8.5 kb HindIII/SalI DNA fragment, comprising the germline human $V_{H1-}$ 18 (DP-14) gene together with approximately 2.5 kb of 5' flanking, and 5 kb of 3' flanking genomic sequence was subcloned into the plasmid vector pSP72 (Promega, Madison, Wis.) to generate the plasmid p343.7.16. A 7 kb BamHI/HindIII DNA fragment, comprising the germline human $V_{H5}$-51 (DP-73) gene together with approximately 5 kb of 5' flanking and 1 kb of 3' flanking genomic sequence, was cloned into the pBR322 based plasmid cloning vector pGP1f (Taylor et al. 1992, Nucleic Acids Res. 20: 6287-6295), to generate the plasmid p251f. A new cloning vector derived from pGP1f pGP1k, was digested with EcoRV/BamHI, and ligated to a 10 kb EcoRV/BamHI DNA fragment, comprising the germline human $V_{H3}$-23 (DP47) gene together with approximately 4 kb of 5' flanking and 5 kb of 3' flanking genomic sequence. The resulting plasmid, p112.2RR.7, was digested with BamHI/SalI and ligated with the 7 kb purified BamHI/SalI insert of p251f. The resulting plasmid, pVx4, was digested with XhoI and ligated with the 8.5 kb XhoI/SalI insert of p343.7.16.

A clone was obtained with the $V_{H1}$-18 gene in the same orientation as the other two V genes. This clone, designated pVx6, was then digested with NotI and the purified 26 kb insert coinjected with the purified 80 kb NotI insert of pHC2 at a 1:1 molar ratio into the pronuclei of one-half day (C57BL/6JxDBA/2J)F2 embryos as described by Hogan et al. (B. Hogan et al., Manipulating the Mouse Embryo, A Laboratory Manual, 2$^{nd}$ edition, 1994, Cold Spring Harbor Laboratory Press, Plainview N.Y.). Three independent lines of transgenic mice comprising sequences from both V×6 and HC2 were established from mice that developed from the injected embryos. These lines are designated (HCO12) 14881, (HCO12)15083, and (HCO12)15087. Each of the three lines were then bred with mice comprising the CMD mutation described in Example 1, the JKD mutation (Chen et al. 1993, EMBO J. 12: 811-820), and the (KCo5)9272 transgene (Fishwild et al. 1996, Nature Biotechnology 14: 845-851). The resulting mice express human immunoglobulin heavy and kappa light chain transgenes in a background homozygous for disruption of the endogenous mouse heavy and kappa light chain loci.

III. Production of HuMabs Against CD30

Human monoclonal antibodies against human CD30 were produced as follows in transgenic mice generated as described above.

Antigen: Soluble CD30 was mixed with Complete Freunds (Sigma F5881) adjuvant for the first immunization. Thereafter, the antigen was mixed with Incomplete Freunds (Sigma F5506). Twenty-five microgram CD30 in 100 μL PBS was mixed 1:1 with the adjuvant using a emulsifying needle. Mice were injected with 0.2 cc prepared antigen into intraperitoneal cavity.

Transgenic Mice: Mice were housed in filter cages and were evaluated to be in good physical condition on the dates of immunization, bleeds, and the day of the fusion.

Immunization Procedure: The mice were immunized with a combination of one IP injection of L540 cells in complete Freund's adjuvant and subsequent IP injections of a soluble recombinant CD30 in incomplete Freund's adjuvant every 14 days. Animals that developed anti-CD30 titers against the CD30 expressing cell line, L540, were given an TV injection of soluble recombinant CD30 seventy-two hours prior to fusion. Mouse splenocytes were harvested, purified and fused. Hybridoma Preparation: The P3 X63 ag8.653 murine myeloma cell line (ATCC CRL 1580, lot F-15183) was used for the fusions. The original ATCC vial was thawed and expanded in culture. A seed stock of frozen vials was prepared from this expansion. Cells were maintained in culture for 3-6 months, passed twice a week. P388D1 (ATCC TIB-63 FL) was expanded to 200 mL and exhausted. The supernatant was spun down and filtered and used as a media addition known as conditioned media. This cell line was passed for 3-6 months and then a new vial was thawed.

High Glucose DMEM (Mediatech, Cellgro # 10013245) containing 5% FBS, and Penicillin-Strepatientomycin (Cellgro # 30004030) was used to culture the myeloma and P388D1 cells. High Glucose DMEM (Mediatech, Cellgro # 10013245) containing 5% FBS, and Penicillin-Strepatientomycin (Cellgro # 30004030) was used to culture the myeloma and P388D1 cells. Additional media supplements were added to the Hybridoma growth media, which included: 3% Origen-Hybridoma Cloning Factor (Igen, 36335), 10% P388D1 conditioned media (Aug. 10, 1999 DH), 10% FBS (Hyclone, SH30071 lot #AGH6843), L-glutamine (Gibco # 1016483) 0.1% gentamycin (Gibco # 1020070), 2-mercapatienthanol (Gibco # 1019091) HAT (Sigma, H0262) $1.0 \times 10^4$ M Hypoxanthine, $4.0 \times 10^{-7}$ M Aminopatienterin, $1.6 \times 10^{-5}$ M Thymidine), or HT ((Sigma, H0137) $1.0 \times 10^{-4}$ M Hypoxanthine, $1.6 \times 10^{-5}$ M Thymidine).

Hybridomas were allowed to grow out for one week until visible colonies become established. Supernatant was harvested and used for initial screening for human IgG via ELISA using a human kappa chain specific capture and a human Fc specific detection. IgG positive supernatants were then assayed for CD30 specificity via flow cytometry using L540 cells and a CD30 ELISA.

Hybridomas producing specific HuMab IgG were subcloned and expanded. HuMabs were then purified by protein A column chromatography using the following procedure: (1) Loading conditions: Supernatant was loaded on a 5 ml Protein-A column that was equilibrated with Phosphate buffered Saline (PBS); (2) Wash: PBS buffer; (3) Elution: 0.1 M Glycine with 150 mM NaCl, pH 2.9. The elute was neutralized with 1M Tris buffer (30 μl for every 2 ml fraction). Each eluted fraction was run on gel before being pooled. Once the purity by coomassie staining was verified, fractions were pooled and dialyzed against 10 mM sodium phosphate buffer with 150 mM $NaCl_2$, pH 7.2. This protocol led to the isolation of three antibodies of interest: 17G1-1; 5F11 and 2H9.

The $V_H$ and $V_L$ regions of HuMab 17G1-1, 5F11 and 2H9 were isolated from RNA from hybridomas, reverse transcribed to cDNA, and V regions were amplified by PCR and the PCR product was sequenced.

Example 2

Binding Studies

I. Determination of Affinity and Rate Constants of HuMab 5F11

Materials (1) Two samples of IgG forms of clone HuMab 5F11 (Medarex, Inc., Annandale, N.J.).

(2) Human CD30 antigen (Medarex, Inc., Annandale, N.J.).

(3) anti-human CD30/TNFRSF8 polyclonal antibody (R&D Systems; catalog no. AF229).

(4) CM5 chip, coupling buffer: 10 mM acetate buffer, pH 6.0 (CD30 coupling) and pH 3.5 (Protein A coupling), regeneration buffer: 10 mM HCL.

(5) Biacore 3000, BiaEval Software v.3.0.1.

Protein A coupling

Protein A (Fc2, 2367 Rus, injection time 10 min, flow: 5 μL/min, pH 3.5) was coupled on a CH5 chip using aminocoupling chemistry.

Binding Study

HuMab 5F11 (1μL/mL) was captured on a protein A surface for 2.5 minutes. (No significant amount of antibody was captured on a protein-G chip, in a separate experiment). Two experiments were done with different concentration ranges of CD30 passed over the captured antibody. Concentration range of experiment 1 included: 10, 6.67, 5, 3.33, and 1.67 μL/mL; experiment 2 included: 5, 4, 2, 1, and 0.5 μL/mL. Association phase lasted 10 minutes followed by a 10 minute dissociation phase. The data were fit to a 1:1 Langmuir model of association to determine the various parameters, as shown in the following table.

TABLE 2

| Exp # | Antibody Sample | $K_{on}$ ($\times 10^4$ 1/Ms) | $K_{off}$ ($\times 10^{-5}$ 1/s) | $K_D$ ($\times 10^{-9}$ M) | Chi2 |
|---|---|---|---|---|---|
| 1 | 5F11 | 6.09 | 7.47 | 1.23 | 2.83 |
| 1 | 5F11 | 5.16 | 7.03 | 1.36 | 10.6 |
| 2 | 5F11 | 6.13 | 6.86 | 1.12 | 7.92 |
| 2 | 5F11 | 5.77 | 6.58 | 1.14 | 13.6 |

Stability of the Captured Antibody Surface

HuMab 5F 11 (1 µL/mL) was captured on a protein A surface for 2.5 minutes. Buffer was allowed to flow for 1.5 hours to mimic association and dissociation phase of CD30 antigen to check if the captured antibody surface is stable. The experiment showed a stable surface with surface levels unchanged (<0.1%), for 5F11 over the total experimental period of time. Accordingly, the 5F11 sample showed similar affinity constants towards CD30 antigen and the captured antibody surface was stable to perform further binding studies.

II. Dose Dependent Binding of HuMabs to Recombinant CD30

The ability of selected HuMabs to bind to recombinant CD30 was investigated by a capture ELISA using a commercially available murine anti-CD30 antibody, BER-H2 (DAKO Corp., Carpenteria, Calif.) as follows.

Microtiter wells were coated with BerH2. After blocking the wells with 5% BSA solution, supernatant from transfected cells expressing recombinant CD30 was allowed to react with BER-H2 coated wells. The supernatant was removed, and protein A purified HuMabs 5F11, 2H9, 17G1, and an isotype control were incubated at varying concentrations with CD30-bound wells at 37° C. After 1 hour, the wells were washed with PBS-tween and the bound antibodies were detected by incubating the cells with an alkaline-phosphatase-labeled goat anti-human IgG Fc-specific probe, at 37° C. The excess probe was washed from the wells and the plate was developed with pNPP developer. The optical density at 405 nm was determined using a microtiter plate reader.

As shown in FIG. 1, the anti-CD30 HuMabs, and not the isotype control, demonstrated dose-dependent binding. This indicates that the anti-CD30 HuMabs specifically recognized the recombinant CD30. The quantitative difference in binding to CD30 among the anti-CD30 HuMabs indicate that 5F11, 2H9, and 17G1 are unique antibodies because the quantitative difference in binding is likely due to differences in affinity or differences in recognition of the recombinant form of CD30.

III. Dose Dependent Binding of HuMabs to L540

The ability of anti-CD30 HuMabs to bind to CD30 on Hodgkin's tumor cells was investigated by flow cytometry as follows.

Antibodies were tested for binding to L540, a Hodgkin's lymphoma cell line that expresses high-levels of CD30. Protein A purified HuMabs 5F11, 2H9, 17G1, and an isotype control were incubated at varying concentrations with the L540 cell line at 4° C. After 1 hour, the cells were washed with PBS and the bound antibodies were detected by incubating the cells with a FITC labeled goat anti-human IgG Fc-specific probe, at 4° C. The excess probe was washed from the cells with PBS and the cell associated fluorescence was determined by analysis using a FACScalibur instrument.

Figure 2:
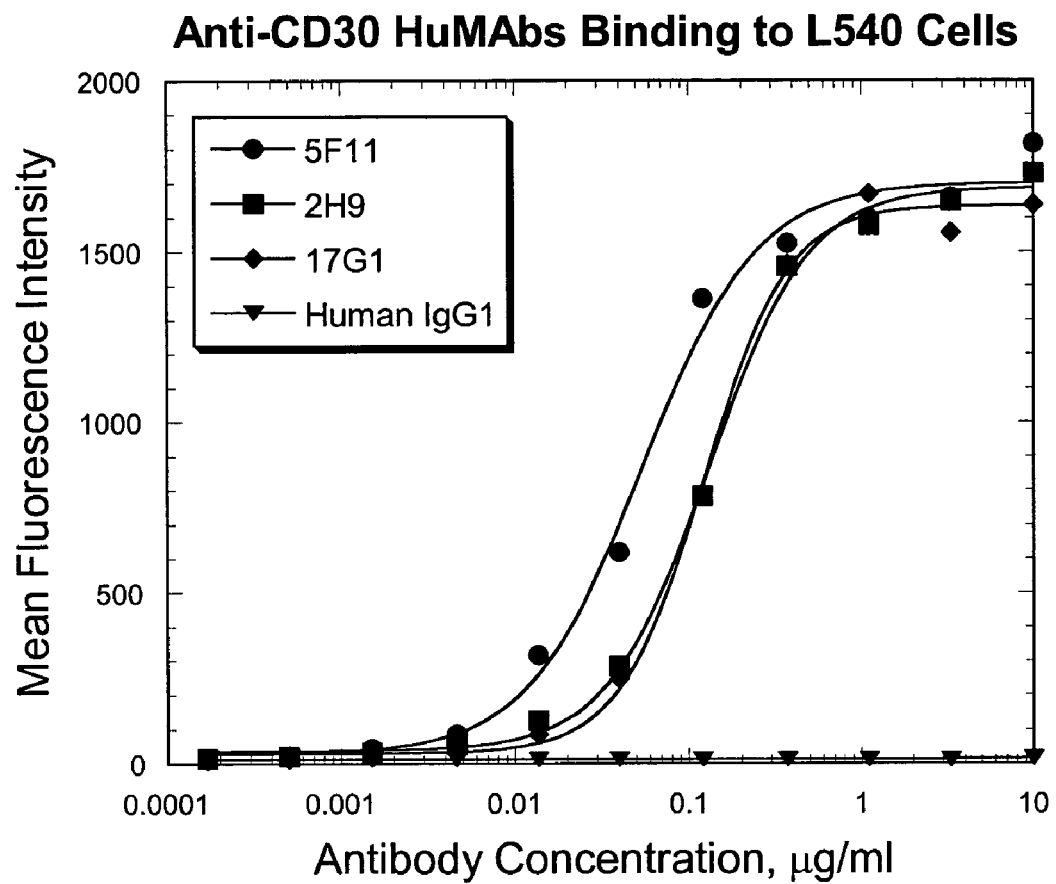
FIG. 2 is a graph comparing dose dependent binding of anti-CD30 HuMabs, 17G 1, 5F11, 2H9 and an isotype control to the Hodgkin's lymphoma cell line, L540.

As shown in FIG. 2, the HuMabs 5F11, 2H9, and 17G1 demonstrated high level binding to L540 cells, with saturation at concentrations below 1 µg/ml. These data demonstrate that these antibodies bind efficiently and specifically to native CD30 expressed on live tumor cells.

IV. Epitope Mapping

CD30 has been shown to contain at least three serologically defined clusters designated A, B, and C. To determine which cluster HuMab 5F11 bound, the ability of murine antibodies specific for either cluster A (Ki 4 and BerH2), cluster B (Ki-1), or cluster C (AC10) to inhibit binding of FITC-labeled 5F11 to L540 cells was investigated. Briefly, L540 cells were incubated simultaneously with FITC-5F11 along with a 10-20 fold excess of unlabeled antibodies for 60 minutes on ice. The cells were washed and analysed by FACS. All blocking antibodies were of murine origin and used in 10-fold excess of their saturation concentration. The 5F11 HuMab (1 µg/ml) was fluroescein isothiocyante (FITC) labeled and binding to CD30 was determined using a fluorescence-activated cell sorter (FACS) flow cytometer (FACScan, Becton Dickinson, Heidelberg, Germany). Primary antibodies were diluted in ice-cold phosphate buffered saline (PBS) containing 0.2% bovine serum albumin and 0.02% sodium azide (staining buffer), incubated with $1 \times 10^5$ L540 cells and 5F11-FITC mAb for 60 minutes on ice.

Figure 14:
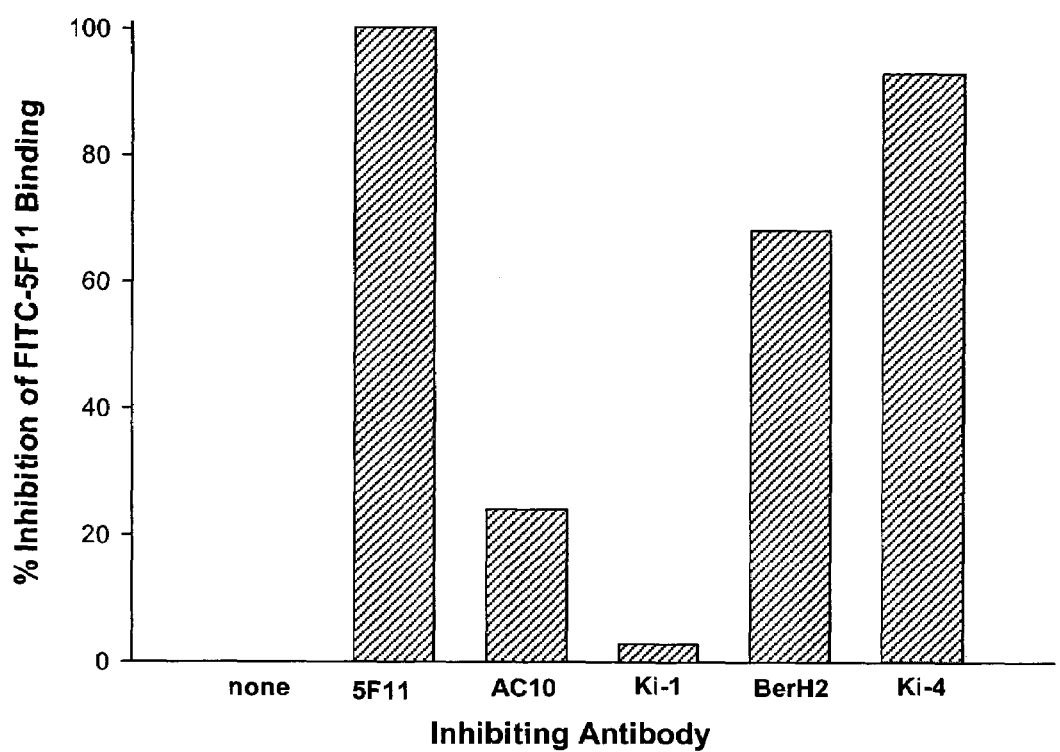
FIG. 14 is a graph showing that antibodies to cluster A were able to inhibit FITC-labeled HuMab 5F11 binding to L540 cells, whereas antibodies to clusters B or C could not, indicating that 5F11 binds to or near the cluster A epitope.

As shown in FIG. 14, the antibodies which bind to cluster A were able to inhibit FITC-5F11 binding to L540 cells, whereas the antibodies which bind to clusters B or C could not, indicating that 5F11 binds to or near the cluster A epitope.

Example 3

Antibody Dependent Cellular Cytotoxicity (ADCC) Studies

I. Monocyte-mediated Antibody Dependent Cellular Cytotoxicity of L540 Hodgkin's Tumor Cells with HuMabs.

The capacity of the anti-CD30 HuMabs to mediate lysis of CD30-expressing tumor cells was investigated using a $^{51}$Cr-release assay with healthy human monocytes. The healthy human monocytes were activated in culture with IFN-γ to up-regulate Fc receptors and cytolytic activity. L540 cells were used as targets for lysis by IFN-γ-activated monocytes. Monocytes purified from normal adult source leukopacs (Biological Specialty Corp., Pa.), were cultured in macrophage serum free medium (M-SFM, Gibco, Grand Island, N.Y.) supplemented with 10% FBS and IFN-γ (1000 u/ml, R & D Systems, Minneapolis, Minn.) for 2 days. Target cells were labeled with 100 µCi of $^{51}$Cr for 1-2 hours prior to combining with effector cells (E:T=50:1) and HuMabs in a U-bottom microtiter plate. After incubation for 16 hours at 37° C. supernatants were collected and analyzed for radioactivity. Cytotoxicity was calculated by the formula: % lysis=(experimental CPM−target leak CPM)/(detergent lysis CPM−target leak CPM)×100%. Specific lysis=% lysis with HuMab−% lysis without HuMab. Assays were performed in triplicate.

Figure 3:
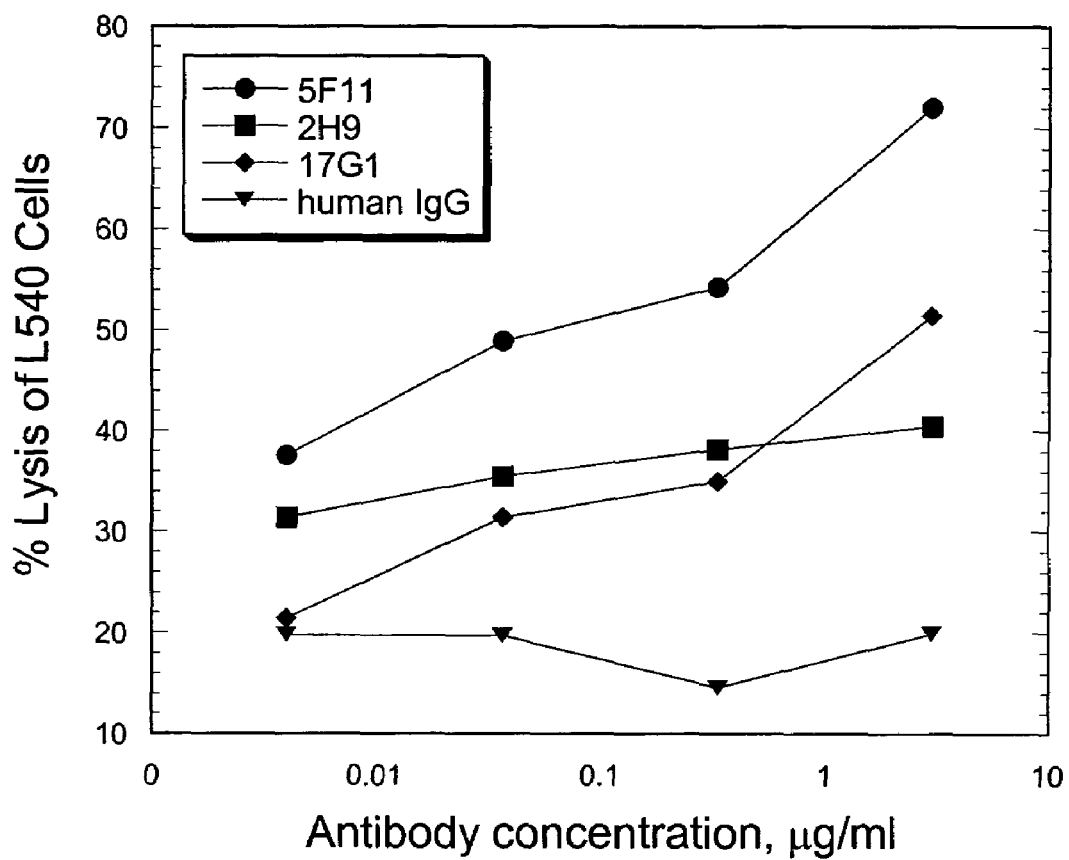
FIG. 3 is a graph comparing mononuclear cell-mediated antibody dependent cellular cytotoxicity of L540 Hodgkin's tumor cells by anti-CD30 HuMabs, 17G1, 5F11, 2H9 and an isotype control.

As shown in FIG. 3, the HuMabs 5F11, 2H9, and 17G1 mediated specific lysis of the Hodgkin's tumor derived L540 cells, as compared to an isotype control. The results demonstrate that these HuMabs are capable of targeting CD30-expressing tumor cells to effector cells for Fc receptor mediated lysis.

II. Mononuclear Cell-mediated Antibody Dependent Cellular Cytotoxicity of L540 Hodgkin's Tumor Cells with HuMabs.

The capacity of the anti-CD30 HuMabs to mediate lysis of CD30-expressing tumor cells was investigated using a $^{51}$Cr-release assay with fresh human mononuclear cells.

L540 cells were used as targets for lysis by fresh human mononuclear cells. Mononuclear cells were purified from heparinized whole blood by ficoll hypaque density centrifugation. Target cells were labeled with 100 µCi of $^{51}$Cr for 1-2 hours prior to combining with effector cells at various effector:target ratios and HuMabs (5 µg/ml) in a U-bottom microtiter plate. After incubation for 4 hours at 37° C. supernatants were collected and analyzed for radioactivity. Cytotoxicity was calculated by the formula: % lysis=(experimental CPM−target leak CPM)/(detergent lysis CPM−target leak CPM)×100%. Specific lysis=% lysis with HuMab−% lysis without HuMab. Assays were performed in triplicate.

Figure 4:
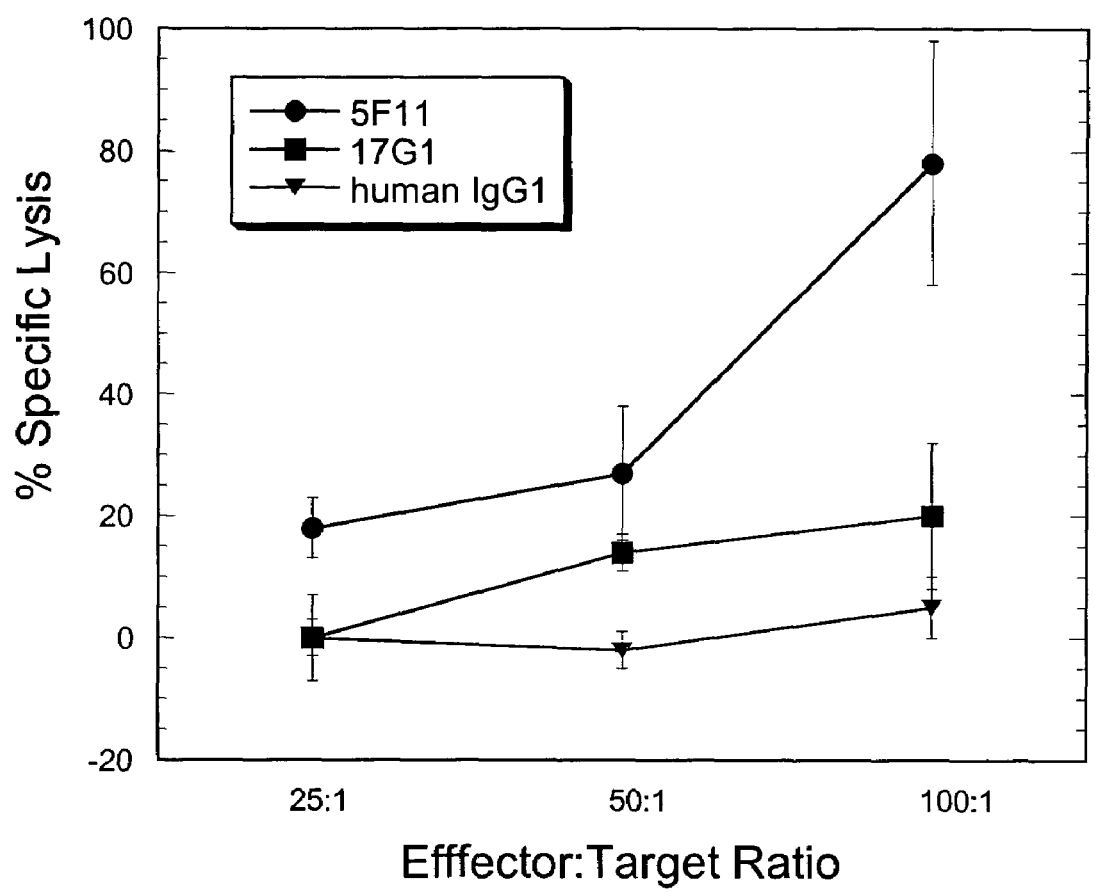
FIG. 4 is a graph comparing monocyte-mediated antibody dependent cellular cytotoxicity of L540 Hodgkin's tumor cells by anti-CD30 HuMabs, 17G1, 5F11, 2H9 and an isotype control.

As shown in FIG. 4, the HuMAbs 5F11 and 17G1 mediated specific lysis of the Hodgkin's tumor derived L540 cells, as compared to an isotype control. The results demonstrate that these HuMabs are capable of targeting CD30-expressing tumor cells to unactivated effector cells, most likely natural killer cells (NK) for Fc receptor mediated lysis.

Example 4

Growth Inhibition of HuMab 5F11

Soluble HuMab 5F11 antibody (0.1, 1, and 10 µg/ml) was cross-linked by a goat-anti-human IgG (GAH-IgG) antibody (10 fold excess) in a 96 well plate with 2×10$^4$ cells per well (L540, L1236, Karpas 299, L428, BL38). Growth inhibition was determined using the XTT, the chromogenic tetrazolium salt (sodium 3'-[1-[(phenylamino)-carbonyl]-3, 4-tetrazolium]-bis (4-methoxy-6-nitro)benzene-sulfonic acid hydrate), assay after incubation at 37° C. and 5% $CO_2$ for 96 hours. Briefly, various dilutions of HuMab 5F11, with or without 10-fold excess of GAH-IgG, were distributed in 100 µl aliquots in 96-well plates. Target cells at 2-4×10$^4$ (L540, L1236, Karpas 299) in 100 µl aliquots of complete medium were added and the plates incubated for 48 hours at 37° C. in a 5% $CO_2$ atmosphere. Cell cultures were then pulsed with. 100 µl fresh culture medium supplemented with XTT and N-methyl dibenzopyrazine methyl sulfate (final concentrations of 1.49 mM and 0.025 mM respectively) for 4 hours. The spectrophotometrical absorbance of the samples was measured at 450 nm and 650 nm (reference wave length) with an ELISA reader (MWG Biotech, Ebersberg, Germany). Negative controls were measured using the GAH-IgG mAb only together with the above mentioned target cells, and using the combination of HuMab 5F11 and the cross-linking antibody, GAH-IgG, on a CD30 negative cell-line (BL38). Cell viability relative to untreated control cultures was calculated using the formula test-value/untreated* 100. All measurements were done in triplicates and repeated twice. In particular, the following controls were used: (1) No secondary cross-linking antibody; (2) secondary cross-linking antibody alone; (3) cells without antibody; and (4) XTT only.

Figure 5A:
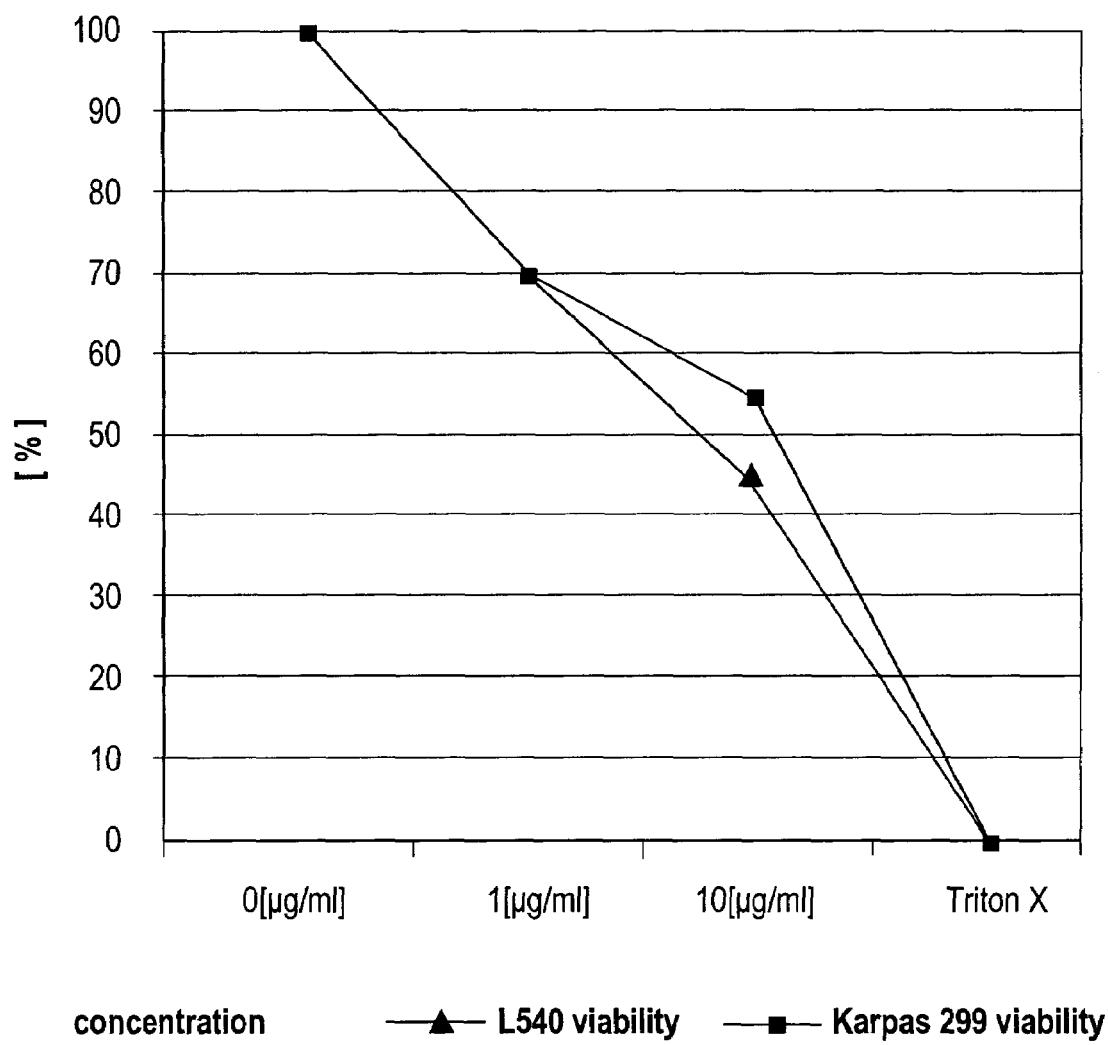
FIGS. 5A and B are graphs showing inhibition of cell growth using HuMab 5F11.
Figure 5B:
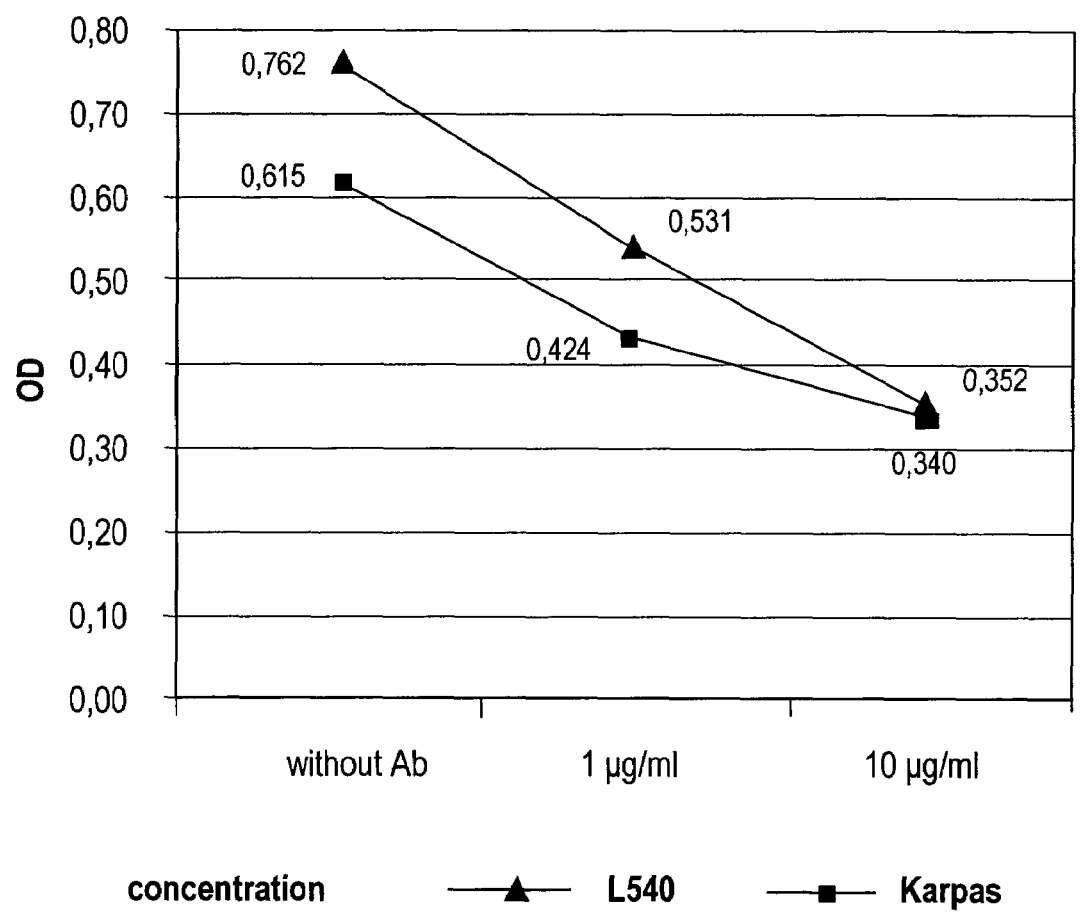

A clear, dose dependent effect on cell-metabolism is shown for the T-cell like HD cells L540 and the Karpas 299 cells, but not for the B-cell like HD cells, L428 and L1236. The IC50 was reached at the highest concentration at 10 µg/ml, suggesting that the cytotoxic effect is moderate (see FIG. 5). This was not an artifact, since neither the GAH-IgG, nor the 5F11 antibody alone showed any effect and activity was restricted to the L540 and Karpas 299 cells.

Example 5

In Vivo Activity of HuMab 5F11

Localized Tumor Model

The ability of HuMab 5F11 to inhibit CD30-expressing tumor cell growth was examined in vivo using a xenografted mouse model. Subcutaneous solid L540CY tumors were established by injection of L540CY cells (1×10$^7$) resuspended in 200 µL PBS into the right flank of SCID mice. Tumor development was measured every 3 days and tumor volume determined using the formula (length *width *height)/2. Animals with established tumors of 4 to 6 mm in the largest diameter were divided randomly into the different groups and received 100 µg 5F11 (in 200 µl PBS i.p.) every 4 days for a total of 4 injections. Control mice received PBS only. The experiment was stopped and the mice sacrificed when the median tumor diameter in the control group exceeded 20 mm (day 107). The treatment and control group consisted of 5 animals each and results were confirmed by a second set of experiments.

Figure 6:
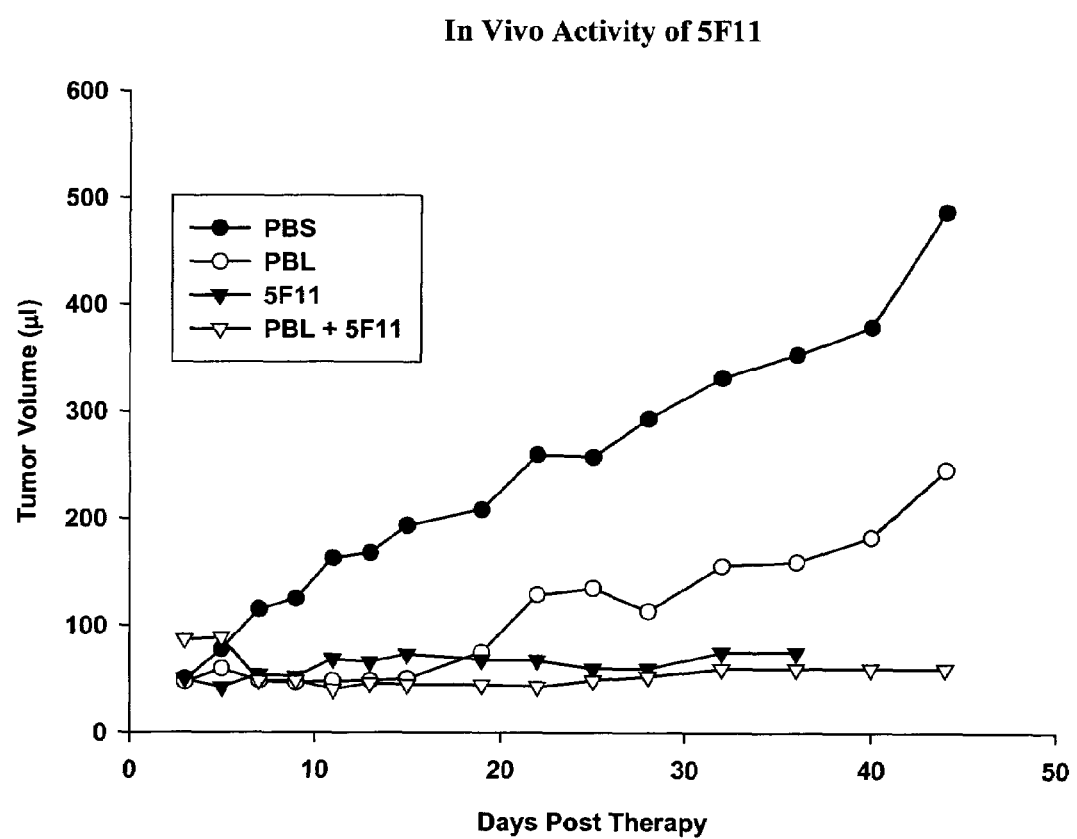
FIG. 6 is a graph showing growth inhibition of CD30-expressing tumor cells by HuMab 5F11 in vivo using a xenografted mouse model.

HuMab 5F11 was given intraperitoneally 4 times every 4 days. Peripheral blood lymphocytes (PBL) were given once intravenously on treatment day 1. The results were expressed as tumor volume plotted against time in days (FIG. 6). PBL administered alone had an impact on the tumor growth, but adding the antibody enhances this effect. The antibody alone showed a comparable anti-tumor activity (FIG. 6). These results demonstrate that HuMab 5F11 is able to inhibit the growth of CD30-expressing tumor cells in an animal model, administered either alone, or in combination with human PBL.

Disseminated Tumor Model

Pathogen free female C.B-17/Icr SCID mice (FOX CHASE SCID®, M&B A/S, Ry, Denmark) were maintained. under pathogen-free conditions and fed autoclaved standard chow and water. A disseminated model was used to evaluate the effects of HuMab 5F11 treatment on the survival of SCID mice challenged with human HL cells L540CY. For the disseminated model, 1×10$^7$ exponentially growing L540CY cells were injected via the tail vein (iv) into the 3-4 weeks old SCID mice. One day after injection of L540CY cells, mice received 100 µg 5F11 intraperitoneally (ip) diluted in 200 µl PBS every 4 days for a total of 4 injections. Control groups included PBS only, 5F11+10 fold excess GAH-IgG mAb, and GAH-IgG mAb alone using the same treatment schedule. Mice with signs of progressive disease (ruffled fur, inactivity, skull deformation) were killed. After gross examination, organs that were macroscopically infiltrated with L540CY cells were fixed in formalin. Animals surviving up to 200 days were killed at that time and major organs were formalin fixed for further examinations.

Figure 15:
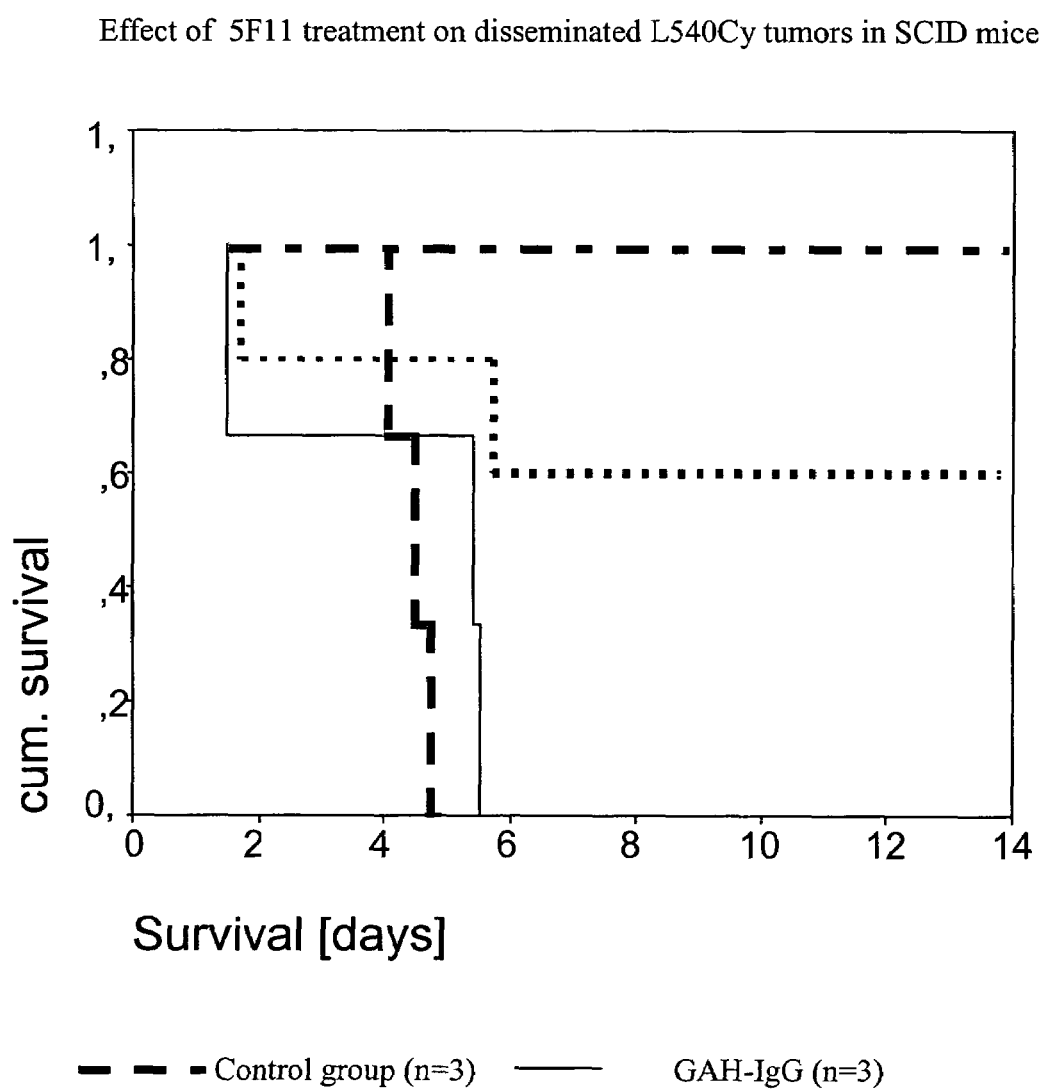
FIG. 15 is graph showing the effects of HuMab 5F11 treatment on the survival of SCID mice challenged with human HL cells L540CY in a disseminated model.

As documented by Kaplan-Meier analysis (FIG. 15), the mean survival time of the PBS treated control group was 43 days (range 40-46 days) and 39 days in the GAH-IgG treated group (range 15-51 days). In the 5F11 treatment group, 3/5 mice were long term survivors (139 days) and showed no signs of disease upon autopsy. One animal died on day 17 without developing any macroscopic signs of disease suggesting that the cause of death was unrelated to the tumor. A second mouse died on day 57 from progressive disease. Upon cross-linking with GAH-IgG mAb, 4/4 mice did not develop any signs of tumor and were sacrificed on day 200. Thus, treatment with HuMab 5F11 was curative for a high proportion of animals in this xenograft model of HL (p=0,01 and p=0,046 for the 5F11+GAH-IgG and 5F11 treatment groups, respectively).

Example 6

Cross-reactivity of Fluoresceinated HuMab 5F11 with Normal Human Tissue

To evaluate potential cross-reactivity of a fluoresceinated form of HuMab 5F11 with cryosections of normal human tissues, an indirect immunoperoxidase method was used. No unanticipated cross-reactivity was observed.

The study was conducted in accordance with the Food and Drug Administration's Laboratory Practice (GLP) Regulations (21 CFR Part 58). The human tissue panel included the tissues on the "suggested list of human tissues to be used for immunohistochemical investigations of cross reactivity" in Annex II of the EC CPMP Guideline III/5271/94, "Production and quality control of monoclonal antibodies" and the tissues recommended in the 1997 US FDA/CBER "Points to Consider in the Manufacture and Testing of Monoclonal Antibody Products for Human Use".

Tissues obtained previously via autopsy or surgical biopsy were embedded in Tissue-Tek® O.C.T. medium and frozen on dry ice. Tissues were sectioned at approximately 5 μm and fixed for 10 minutes in room temperature acetone. The test article was applied to the slides at two concentrations (2 and 10 μg/mL) and an indirect immunoperoxidase method (Dako EnVision Kit) was used to detect binding.

The results indicated that the test article HuMab 5F11-FITC specifically stained the membrane of positive control CD30-expressing L540 cells, a Hodgkin's disease-derived cell line, as well as the membrane of positive control CD30-expressing lymphocytes in human tonsil. Reactivity with positive control cryosections was strong to intense at both concentrations examined (10 μg/mL and 2 μg/mL). In human tonsil, the CD30-positive cells were located at the periphery of the follicles as well as in the adjacent interfollicular regions, and represented less than 1-2% of tonsil cells.

Examination of the panel of human test tissues indicated that cross-reactivity was not observed in any tissue except human tonsil. In all three donors examined, reactivity was observed with lymphocytes/mononuclear cells located at the periphery of the follicles as well as in the adjacent interfollicular regions. Fewer than 1% of tonsil cells were stained. This reactivity was expected based on previous reports of tonsil expression of CD30 (Hecht et al., 1985).

Example 7

Antibody Sequencing

As described above in Example 1, HuMabs from hybridomas producing specific HuMab IgG were purified by protein A column chromatography which led to the isolation of three antibodies of interest: 17G1-1, 5F11 and 2H9. The $V_H$ and $V_L$ regions of HuMabs 17G1-1, 5F11 and 2H9 were subsequently isolated from hybridoma RNA, reverse transcribed to cDNA, the V regions were amplified by PCR and the PCR product was sequenced. The following are the nucleic and amino acid sequences of the $V_H$ and $V_L$ regions of the HuMabs.

```
17G1 V_H nucleic acid sequence:         (SEQ ID NO:1)
GAGGTGCAGTTGGTGGAGTCTGGGGGAGGCTTGGTCCAGCCTGGG

GGGTCCCTGAGACTCTCCTGTGTAGCCTCTGGATTCACCTTTAGTAA

CTCTTGGATGAGCTGGGTCCGCCAGGCTCCAGGGAAAGGGCTGGA

GTGGGTGGCCAACATAAACGAAGATGGAAGTGAGAAATTCTATGT

GGACTCTGTGAAGGGCCGATTCACCTTCTCCAGAGACAACGCCGAG

AACTCACTGTATCTGCAAATGAACAGCCTGAGAGCCGAGGACACG

GCTGTGTATTACTGTGCGAGGGTTCATTGGTACTTCCATCTCTGGGG

CCGTGGCACCCTGGTCACTGTCTCCTCA

17G1 V_H amino acid sequence:          (SEQ ID NO:2)
EVQLVESGGGLVQPGGSLRLSCVASGFTFSNSWMSWVRQAPGKGLE

WVANINEDGSEKFYVDSVKGRFTFSRDNAENSLYLQMNSLRAEDTAV

YYCARVHWYFHLWGRGTLVTVSS

17G1 V_L nucleic acid sequence         (SEQ ID NO:3)
GAAATTGTGTTGACGCAGTCTCCAGGCACCCTGTCTTTGTCTCCAG

GGGAAAGAGCCACCCTCTCCTGCAGGGCCAGTCAGAGTGTTAGCA

GCAGCTACTTAGCCTGGTACCAGCAGAAACCTGGCCAGGCTCCCAG

GCTCCTCATCTATGGTGCATCCAGCAGGGCCACTGGCATCCCAGAC

AGGTTCAGTGGCAGTGGGTCTGGGACAGACTTCACTCTCACCATCA

GCAGCCTGGAGCCTGAAGATTTTGCAGTGTATTACTGTCAGCAGTA

TGGTAGCTCACCGTGGACGTTCGGCCAAGGGACCAAGGTGGAAAT

CAAA

17G1 V_L amino acid sequence          (SEQ ID NO:4)
EIVLTQSPGTLSLSPGERATLSCRASQSVSSSYLAWYQQKPGQAPRLLI

YGASSRATGIPDRFSGSGSGTDFTLTISSLEPEDFAVYYCQQYGSSPWT

FGQGTKVEIK

2H9 V_H nucleic acid sequence         (SEQ ID NO:5)
CAGGTGCAGCTACAGCAGTGGGGCGCAGGACTGTTGAAGCCTTCG

GAGACCCTGTCCCTCACCTGCGCTGTCTATGGTGGGTCCTTCAGTG

GTTACTACTGGAGCTGGATCCGCCAGCCCCCAGGGAAGGGGCTGG

AGTGGATTGGGGAAATCAATCATAGTGGAAGCACCAAGTACACCC

CGTCCCTCAAGAGCCGAGTCACCATATCAGTAGACACGTCCAAGCA

CCAATTCTCCCTGAAGCTGAGCTCTGTGACCGCCGCGGACACGGCT

GTGTATTACTGTGCGAGAGAGACTGTCTACTACTTCGATCTCTGGG

GCCGTGGCACCCTGGTCACTGTCTCCTCA

2H9 V_H amino acid sequence           (SEQ ID NO:6)
QVQLQQWGAGLLKPSETLSLTCAVYGGSFSGYYWSWIRQPPGKGLE

WIGEINHSGSTKYTPSLKSRVTISVDTSKHQFSLKLSSVTAADTAVYYC

ARETVYYFDLWGRGTLVTVSS

2H9 V_L nucleic acid sequence         (SEQ ID NO:7)
GAAATTGTGTTGACACAGTCTCCAGCCACCCTGTCTTTGTCTCCAG

GGGAAAGAGCCACCCTCTCCTGCAGGGCCAGTCAGAGTGTAAGCA
```

```
-continued
GCAACTTAGCCTGGTACCAACAGAAACCTGGCCAGGCTCCCAGGCT

CCTCATCTATGATGCATCCAACAGGGCCACTGGCATCCCAGCCAGG

CTCAGTGGCAGTGGGTCTGGGACAGACTTCACTCTCACCATCAGCA

GCCTAGAGCCTGAAGATTTTGCAGTTTATTACTGTCAACAGCGTAG

CAACTGGCCGTGGACGTTCGGCCAAGGGACCAAGGTGGAAATCAA

A

2H9 V_L amino acid sequence              (SEQ ID NO:8)
EIVLTQSPATLSLSPGERATLSCRASQSVSSNLAWYQQKPGQAPRLLIY

DASNRATGIPARLSGSGSGTDFTLTISSLEPEDFAVYYCQQRSNWPWTF

GQGTKVEIK

5F11 V_H nucleic acid sequence           (SEQ ID NO:9)
CAGGTGCAGCTACAGCAGTGGGGCGCAGGACTGTTGAAGCCTTCG

GAGACCCTGTCCCTCACCTGCGCTGTCTATGGTGGGTCCTTCAGTG

CTTACTACTGGAGCTGGATCCGCCAGCCCCCAGGGAAGGGGCTGG

AGTGGATTGGGGACATCAATCATGGTGGAGGCACCAACTACAACC

CGTCCCTCAAGAGTCGAGTCACCATATCAGTAGACACGTCCAAGAA

CCAGTTCTCCCTGAAGCTGAACTCTGTAACCGCCGCGGACACGGCT

GTGTATTACTGTGCGAGCCTAACTGCCTACTGGGGCCAGGGAAGCC

TGGTCACCGTCTCCTCA

5F11 V_H amino acid sequence             (SEQ ID NO:10)
QVQLQQWGAGLLKPSETLSLTCAVYGGSFSAYYWSWIRQPPGKGLE

WIGDINHGGGTNYNPSLKSRVTISVDTSKNQFSLKLNSVTAADTAVYY

CASLTAYWGQGSLVTVSS

5F11 V_L nucleic acid sequence           (SEQ ID NO:11)
GACATCCAGATGACCCAGTCTCCAACCTCACTGTCTGCATCTGTAG

GAGACAGAGTCACCATCACTTGTCGGGCGAGTCAGGGTATTAGCA

GCTGGTTAACCTGGTATCAGCAGAAACCAGAGAAAGCCCCTAAGT

CCCTGATCTATGCTGCATCCAGTTTGCAAAGTGGGGTCCCATCAAG

GTTCAGCGGCAGTGGATCTGGGACAGATTTCACTCTCACCATCAGC

AGCCTGCAGCCTGAAGATTTTGCAACTTATTACTGCCAACAGTATG

ATAGTTACCCTATCACCTTCGGCCAAGGGACACGACTGGAGATTAA

A

5F11 V_L amino acid sequence             (SEQ ID NO:12)
DIQMTQSPATIENTSLSASVGDRVTITCRASQGISSWLTWYQQKPEKAP

KSLIYAASSLQSGVPSRFSGSGSGTDFTLTISSLQPEDFATYYCQQYDSY

PITFGQGTRLEIK
```

Example 8

CD30 Mediated Treatment of Hodgkin's Disease (HD) in Humans

Hodgkin's disease (HD) has become a curable disease due to the introduction of polychemotherapy regimens like MOPP or ABVD and improved radiation techniques (Devita VT, Jr. et al. *Ann Intern Med* 73:881 (1970); Bonadonna G et al. *Cancer Treat Rep* 66:881 (1982); Kaplan H. S. *Cancer* 45:2439 (1980)). More recently, patients with advanced stage disease have shown improved response and survival rates using the BEACOPP-regimen established by the German Hodgkin's Lymphoma Study Group (Diehl V et al. *J Clin Oncol* 16:3810 (1998)). However, although most patients can be cured by standard approaches, fewer than 30% of those who relapse attain durable disease-free remissions after second-line treatment (Carella A. M. et al. Leuk Lymphoma 7 Suppl:21 (1992)). The outcome is even worse for those with primary refractory disease (Linch D. C., et al. Lancet 341:1051 (1993)).

Data from Hodgkin's disease as well as from other malignant diseases including colorectal cancer, myeloid leukemia, or non-Hodgkin's lymphoma (NHL), suggest that small numbers of residual tumor cells remaining after first-line treatment can give rise to late relapses (Kanzler H et al. Blood 87:3429 (1996); Wolf J et al. Blood 87:3418 (1996); Riethmuller G et al. Lancet 343:1177 (1994); Roy D. C. Blood 77:2404 (1991); Gribben J. G. et al. N Engl J Med 325:1525 (1991) Thus, eliminating residual Hodgkin-Reed/Sternberg (H-RS) cells after first-line treatment might further improve outcome in HD. A number of different monoclonal antibodies have been evaluated for treatment of HD patients, including antibody-toxin constructs (immunotoxins), radioimmunoconjugates, and unmodified monoclonal antibodies. (Herpst J. M. et al., *J Clin Oncol* 13:2394 (1995); Schnell R., et al., *Leuk Lymphoma* 30:525 (1998); Engert A., et al., *Blood* 89:403 (1997); Schnell R., et al., submitted, (2001)). As a possible alternative, bispecific antibodies have attracted interest as immunoreagents in HD. In general, bispecific antibodies have been shown to be well tolerated. However, side effects and cytotoxic potential of these constructs crucially depend on the effector cells targeted.

So far, most bispecific antibodies involved different subsets of lymphocytes or NK cells, which are less effective in patients with malignant disease and in particular HD (Hartmann F., et al., *Blood* 89:2042 (1997)). Thus, a new bispecific molecule (bispecific molecule) based on the high affinity FcγRI receptor (CD64) which is expressed on activated neutrophils, monocytes, and macrophages (Ravetch J. V. et al., *Annu Rev Immunol* 9:457 (1991)) was constructed. CD64 serves as a trigger molecule on cytotoxic effector cells expressing FcγRI. Both monomeric IgG as well as IgG-antigen complexes bind to FcγRI. Binding of only IgG-antigen complexes to FcγRI results in increased cytotoxic activity, including cytolysis, respiratory burst, and production of oxidative enzymes (Fanger M. W. et al., *Immunol Today* 10:92 (1989); van de Winkel J. G. et al. *J Leukoc Biol* 49:511 (1991)).

The murine monoclonal antibody, M22, binds to the FcγRI at an epitope outside the normal Fc binding domain, thereby circumventing the competition with serum IgG (Guyre P. M. et al., *J Immunol* 143:1650 (1989)). The binding unit used for construction of the new bispecific molecule reported of the present invention is based on the humanized version of the anti-CD64 monoclonal antibody M22 termed H22 (Graziano R. F. et al., *J Immunol* 155:4996 (1995)). H22 F(ab') fragments were chemically linked to F(ab') fragments derived from the anti CD30 monoclonal antibody Ki-4. The resulting bispecific molecule H22xKi-4 has a molecular weight of 104 kDa and thus allows for better tumor penetration compared to a complete antibody. In addition, this type of construct does not activate complement or bind to non-cytotoxic cells that express Fc-receptors, resulting in minimal side effects (Fanger M. W. et al., *Crit Rev Immunol* 12:101 (1992)). Pre-clinical in vitro testing of H22xKi-4 demonstrated that this bispecific molecule mediates antibody-dependent cellular cytotoxicity (ADCC) in conjunction with monocytes as well as phagocytosis in conjunction with monocyte-derived macrophages (MDM) (Sundarapandiyan K. et al., *J Immunol Methods* 248:113 (2001)). Thus, CD64 is a promising target for the recruitment of immunocompetent effector cells in HD. The following clinical phase-I study, was performed to demonstrate the efficacy of this novel therapeutic bispecific molecule in patients with HD.

I. Patients and Methods

Patients

Eligible patients had measurable and active advanced refractory HD not amendable for conventional chemotherapy. Presence of the CD30 antigen had to be documented by reactivity with anti-CD30 antibodies on ≧30% of H-RS cells obtained from tumor biopsy performed within 1 year before treatment with H22xKi-4. Prior chemotherapy or radiotherapy had to be completed four weeks before study drug administration. In addition, the following conditions had to be fulfilled: presence of objectively measurable sites of disease, World Health Organization (WHO) performance status of 2 or less, age between 18 and 70 years, life expectancy of at least three months, serum-creatinine of less than 2 mg/100 ml, serum-albumin of more than 75% of the lower limit, cardiac function as measured by echocardiography with a baseline left ventricular ejection fraction (LVEF) greater than 35%, and no other major medical problems. Concomitant corticosteroid treatment was not an exclusion criterion since patients with progressive HD often require corticosteroid therapy. The protocol was approved by the institutional ethics committee and patients had to give written informed consent as to the investigational nature of the treatment.

Study Design

This clinical trial was an open-label, non-randomized, phase-I dose-escalation study. The primary objective was to determine the maximum tolerated dose (MTD) of H22xKi-4 in humans when administered by intravenous infusion. Secondary objectives included the pharmacokinetics, the dose limiting toxicity (DLT), the biological optimum dose, and any antitumor activity. Patients received at least two courses of treatment consisting of four infusions each. H22xKi-4 was administered on day 1, 3, 5 and 7, respectively. Additional courses were added according to the individual investigator's judgement in responding patients.

Dose Escalation and Major Toxicity Rules

Maximum tolerated dose (MTD) was defined as the highest dose level immediately below the dose limited by toxicity. This dose was defined by the occurrence of a DLT in at least two of three or six patients. Six patients had to be treated on the MTD. The MTD was evaluated using the accelerated titration design as follows: double step (100%) dose escalation with one patient per cohort in the accelerated phase until the first instance of DLT at any course or the second instance of any course grade II toxicity was observed (Simon R. et al., *J Natl Cancer Inst* 89:1138 (1997)). Then, the cohort of the current dose level had to be expanded to at least three patients and standard modified Fibonacci dose escalation scheme (with 50% dose increments) was used for all following dose levels. Adverse events not judged to be related to the study drug were not be considered as a toxicity in terms of these dose escalation rules and rules for determination of the MTD. The dose groups were as follows: 1.0 mg/m$^2$/d, 2.5 mg/m$^2$, 5 mg/m$^2$/d, 10 mg/m$^2$/d, and 20 mg/m$^2$/d. A total of 6 patients were enrolled on the 20 mg/m$^2$/d dose level irrespective of the lack of toxicities. DLT was defined as any grade III or IV non-hematological toxicity (according to NCI criteria) or grade IV hematological toxicity excluding lymphopenia, monocytopenia or neutropenia. Patients could start with the next dose level, if the third administration of H22xKi-4 on the previous dose level had been completed without DLT. Vital signs were controlled every hour during the infusion and up to six hours thereafter. Patients were monitored weekly including complete blood cell count, biochemistry, urine status, performance status and toxicity assessment according to WHO criteria. On day 28 of each course, baseline evaluations were repeated including electrocardiography, chest x-ray, echocardiography, lung function test, serum-creatinine, and assessment of tumor response.

Drug Formulation and Administration

H22xKi-4 was produced using the method of Glennie as described previously (Glennie M. J. et al., *J Immunol* 139:2367 (1987)). The drug was supplied in sterile, 10 ml vials containing 1 mg/ml H22xKi-4 and had to be stored at 4° C. Prior to each infusion, patients received an initial test dose of either 10% of the total dose or 0.2 mg, whichever was smaller, of H22xKi-4, dissolved in 50 ml normal saline and administered intravenously over 10 minutes. Patients were then pre-medicated with 1000 mg of acetaminophen orally, and 1 mg of clemastine orally 30 minutes prior to receiving the final dose of H22xKi-4. If this test-dose was tolerated without any significant toxicity after 30 minutes, H22xKi-4 was diluted in 500 ml normal saline and administered intravenously starting with 3 mg/h. If no adverse reactions were noted after 60 minutes, the infusion rate was increased to 6 mg/h and then to 9 mg/h respectively.

Pharmacokinetics

On the first day of H22xKi-4 administration, blood samples were drawn in heparinized tubes at the following time points: pre-infusion, immediately after infusion, 2, 4, 8, 12, 24, and 48 hours after each infusion. Plasma was separated from blood cells by spinning at 1.200 g for 10 minutes and subsequently stored at −20° C. until analysis of pharmacokinetics. The limit of detection of the H22xKi-4 assay was 0.125 µg/ml for the first three patients and 0.04 µg/ml for all following patients. The data for the plasma H22xKi-4 concentration over time were inspected on a semi-logarithmic plot of H22xKi-4 concentration versus time for each subject. The $C_{max}$ and $T_{max}$ values were the values observed from the raw pharmacokinetic data. The other standard pharmacokinetic parameters were estimated using the WinNonlin Pro pharmacokinetic program (Pharsight Corporation, Mountain View, Calif.). The concentration-time data was analyzed using an open non-compartmental method (WinNonlin model 202). The terminal elimination rate constant ($k_e$) was determined by non-compartmental analysis using a linear regression of the terminal 3-6 points of the log plasma H22xKi-4 concentration versus time plot, using a non-weighted paradigm. The terminal elimination half-life ($T_{1/2}$) was estimated from $0.693/k_e$. The AUC to the last datum point was estimated using the linear-trapezoidal rule, and extrapolated to infinity by adding the Wagner-Nelson correction ($C_{last}/k_e$). Total body clearance (CL) was calculated by dividing the Dose/AUC (0-infinity). The apparent volume of distribution (Vdz) was estimated from $CL/k_e$. The mean residence time (MRT) was estimated from AUMC/AUC. The apparent volume of distribution at steady state (Vdss) was estimated from the equation Vdss=CL×MRT. The accumulation factor-R was estimated from the equation Treat×AUC$_{(0-\tau)}$/Treat 1 AUC$_{(0-\infty)}$. In this Treat×AUC$_{(0-\tau)}$ was the AUC from zero to the dosing interval on any treatment occasion and $AUC_{(0-\tau)}$ was the AUC from zero-infinity on day 1.

Evaluation of Biological Activity

Since DLTs with the bispecific molecule of the present invention were not likely to occur, surrogate parameters for the biological activity were investigated. Monocyte counts in the peripheral blood were measured immediately before and after infusion of H22xKi-4 and at 2, 4, 8 and 24 hours after infusion. CD64-expression was determined by FACS-analysis and correlated to an isotype control, using an appropriate antibody (FACS-Calibur, Becton-Dickinson). At the same time-points, serum-levels of Il-6, Il-15, G-CSF, and TNFα were determined, using commercial enzyme linked immunosorbent assays (ELISA) kits. Cytokine level before treatment were then related to those after treatment with the bispecific molecule and tested for significance using the Wilcoxcon-test. Correlation to bispecific molecule-level was tested using the Pearson's coefficient.

With regard to the tumor, sCD30 levels were measured by ELISA (DAKO) before and after each day of bispecific molecule administration. Two patients gave informed consent for a diagnostic biopsy of enlarged peripheral lymph nodes 24 h after the last infusion of H22xKi-4. This material was divided into two parts, one of which was immediately fresh frozen and stored at −80° C. and the other was embedded in paraffin. For immunohistochemical investigation, the tissue was deparaffinized, cut into sections of 5 µm and blocked with pig serum for 10 minutes to reduce unspecific staining. Then the primary monoclonal antibody, a polyclonal rabbit-anti-mouse Ab (DAKO), diluted 1:50 in PBS was applied and incubated at 4° C. over night, followed by a biotylinated pig-anti-rabbit antibody (1:200 for 45 minutes at room temperature, E 431 DAKO) and a standard biotin-strepatientavidin kit (DAKO). Finally, the slides were stained with fast-red (DAKO). As a first negative-control (bispecific molecule-free) a specimen of HD from a patient, who had not been treated in this study, was stained during the same procedure. A second negative-control (to exclude unspecific cross-reactivity from the other antibodies used for the staining procedure) was material obtained in this trial and stained without primary antibody.

HABA/HAMA-response

Human-anti-bispecific-antibody response was determined using a method as described previously (Pullarkat V., et al., *Cancer Immunol Immunother* 48:9 (1999)). Briefly, microtiter plates coated with the bispecific molecule were incubated with dilutions of plasma samples and anti-bispecific molecule antibodies detected with an alkaline-phosphatase conjugated goat-anti-(human IgG) Fc-specific probe. HABA-levels were expressed as x-fold increase over the baseline pre-infusion value.

Assessment of Response

Staging was performed in accordance to the Ann-Arbor classification system. Complete remission (CR) was defined as the absence of any clinical or radiological evidence of active disease over a period of at least 4 weeks. Partial remission (PR) was defined as 50% or more decrease in the product of the two largest perpendicular diameters of all measurable lesions, as determined by two consecutive observations not less than 4 weeks apart. Less than 25% decrease or increase in total tumor mass, again persisting for at least 4 weeks, were defined as no change (NC). Progressive disease was defined as the appearance of any new lesions or an increase of more than 25% in tumor size.

II. Results

Patients Characteristics

A total of 10 multiple pretreated relapsed HD patients treated on 5 different dose levels were included and are evaluable, of whom 2 were female. The median age was 34.6 years ranging from 21 to 53 years. Histology included 3 patients with mixed cellularity of Hodgkin's disease and 7 patients with the nodular sclerosis subtype. The median number of relapse was 3 (range 1 to 7). A median of 4 prior chemotherapies had been administered (range 2 to 6), including high dose chemotherapy with autologous stem cell support in 9/10 patients. In addition, all patients had been pretreated with radiotherapy. Of the patient group, 7 patients had stage IV disease, 3 patients had stage III disease, 5 patients had B-symptoms on study entry and 8 patients were treated with two courses of H22xKi-4, one patient received three and one patient received four courses (consisting of four infusions each course) of treatment, respectively.

Toxicity

All side effects were transient occurring during and up to six hours after the end of the infusion (see table 2). In all ten patients, mild fatigue was observed. Other toxicities included mild hypotension (4 grade I), tachycardia (6 grade I), fever (2 grade I, 3 grade II), chills (4 grade I), and myalgia (3 grade 1). All of these side effects resolved within 24 hours. Neither hematological nor organ toxicities were observed.

Pharmacokinetics

Bispecific molecule levels were detectable only in those patients receiving more than 5 mg/m²/d. $T_{max}$ occurred at or after the end of the infusion in all subjects on all treatment days. The plasma concentration decay over time was monoexponential for all patients. There was a trend for $C_{max}$ and AUC to increase over time. Therefore, an univariate, single factor, repeated measures analysis of variance for $C_{max}$, $T_{1/2z}$, AUC, Cl and $Vd_z$ over a one week time period of treatment was performed. This analysis revealed a significant time effect on $C_{max}$ (F=5.885; p=0.006) and AUC (F=5.976; p=0.005). This is suggestive of an accumulation of H22xKi-4 with repeated dosing (see FIGS. 1 and 2). For all patients studied, the median value of the accumulation factor R is 1.36 (range 0.98-3.90) by the 4th dose. The H22xKi-4 terminal half-life was 7.9 h at the 10 mg/m²/d dose (n=1) and had a value of 11.1 h (mean) at the 20 mg/m²/d dose level (median 11.1 h; range of 5.3-18.2 h) (see table 3). The volume of distribution ranged from 20.26 to 183.20 L/m². The mean value of the volume distribution ($Vd_z$) in the 20 mg/m² group was 53.17 L/m². The total body clearance of H22xKi-4 on day 1 varied from 1.02 to 14.06 L/m² with a mean value for the group of patients who received 20 mg/m² of 3.91 L/h/m2 (SD 5.04 L/h/m²). Low level HABA were detectable after the end of the second course in all patients with measurable bispecific molecule-levels, neither resulting in decreased serum levels of the bispecific molecule nor in allergic reactions (see table 2). The patient treated with four cycles of the bispecific molecule developed high HABA levels.

Biological Activity

There was a release of Il-6, IL-15, TNFα, and G-CSF with the maximum at two to four hours after the end of H22xKi-4 infusion. The cytokine release was not significant, probably due to the limited number of evaluable patients (n=6) and the high inter-patient variability of cytokine levels. Nevertheless, there was e clear trend for the cytokine release as shown in FIGS. 3 and 4. The cytokine release seemed to ameliorate with repeated administration of the bispecific molecule and was more pronounced for G-CSF, TNF-α, and IL-15. Coincidentally, there was a significant decrease of the CD64 expression on peripheral blood monocytes (p=0.018) as well as a decline of their blood counts (see FIG. 5). Serum sCD30-level were markedly elevated in patients with a high tumor burden, but were no longer detectable after the first infusion of the bispecific molecule and remained at very low level until the end of treatment in all patients (data not shown).

Immunohistochemistry

The murine fragment of the bispecific molecule could be detected in the lymph node specimen of both patients using the above described method (see FIG. 6). There was a clear staining of the HRS-cells, that was located throughout the cytoplasm. In addition, macrophages in this tissue showed an identical staining pattern. Thus, there was clear evidence for the penetration of the bispecific molecule into the malignant lymph nodes.

Tumor Response

Overall, there were 4 patients with objective responses to the H22xKi-4 bispecific molecule. One CR was seen in a patient with diffuse pulmonary nodules up to a maximum of 10 mm. This response lasted for 3 months, then the pulmonary nodules became measurable again by CT-scan and a rescue chemotherapy was initiated. PR was documented in three patients lasting from 4 weeks to 5 months. One patient (No 4) had additional chemotherapy after 4 weeks. In this patient, the only site of the disease was a thoracic vertebra infiltration. Treatment with the bispecific molecule led to a complete resolution of neurologic defects and to a measurable partial response. Since there was no additional improvement of the response after another two cycles of H22xKi-4, chemotherapy was given in order to minimize the risk of disease progression and a possibly fatal fracture of the vertebra.

Two patients treated at the lowest two dose levels had progressive disease, and four patients showed stable disease. Of these, one patient (No 6) with massive tumor burden (infiltration of the right upper lung with pleural and thoracic wall infiltration), who had experienced life threatening toxicities (sepsis, acute renal failure, mechanical ventilation for two months) upon preceding chemotherapy achieved a marked improvement of his symptoms (cough, night sweats). Disease stabilization and normalization of his general conditions lasted for 12 months.

III. Conclusion

The study described above demonstrated the following: 1) H22xKi-4 is well tolerated at doses up to 80 mg/m$^2$ (given on day 1, 3, 5, and 7) with only mild to moderate and transient side effects. There were no dose limiting toxicities and the maximum tolerated dose of this construct was not reached; 2) The half-life of H22xKi-4 at the maximum dose given is 11.1 hours, leading to a significant accumulation of the drug as determined by $C_{max}$ and AUC over the treatment period; 3) There was a cytokine release of IL-6, IL-1 5, TNFα and G-CSF, as well as a decrease of monocytes and CD64-expression suggesting a biologic effective dose and schedule; 4) H22xKi-4 induces tumor response in patients with pretreated advanced and refractory HD.H22xKi-4 is a new bispecific molecule consisting of two chemically linked F(ab') fragments derived from the murine anti-CD30 monoclonal antibody Ki-4 and the humanized anti-CD64 monoclonal antibody H22. This construct had shown activity against H-RS cell lines in vitro (Sundarapandiyan K. et al., *J Immunol Methods* 248:113 (2001)).

In the present and first clinical trial of H22xKi-4, the most common side effect was fatigue which occurred in all ten patients treated. Other side effects included tachycardia, hypotension, chills, fever, and myalgia. The toxicity profile of H22xKi-4 resembles the "cytokine-release syndrome" as described for several monoclonal antibodies against lymphoma cells including Rituximab, Campath-1H, or OKT3 (Winkler U., et al., *Blood* 94:2217 (1999); Wing M. G. et al., *J Clin Invest* 98:2819 (1996); Norman D. J. et al., *Transplant Proc* 25:89 (1993)). These symptoms occurred at all dose levels suggesting biologic activity even at lower doses. Only grade-II fever and mild myalgia were restricted to the highest dose level. The onset of symptoms varied but lasted no longer than six hours after the end of infusion. A direct correlation between side effects and the serum levels of H22xKi-4 or the cytokines determined in this study was not observed.

Despite the fact that comparably high doses of the bispecific molecule were used, the MTD of H22xKi-4 was not ascertainable. Six patients were treated with 80 mg/m$^2$ per cycle and the highest total amount of bispecific molecule given to one patient was 740 mg. Since there were no major side effects at this dose level, 80 mg/m$^2$ per cycle given at days 1, 3, 5, and 7 is a safe dose. Very similar findings are known from other specific monoclonal antibodies such as rituximab (Maloney D. G. et al., *J Clin Oncol* 15:3266 (1997)). Thus, 80 mg/m$^2$ per cycle is a biological active dose, particularly since a saturation of the peripheral blood monocytes similar to previous studies using comparable anti-CD64 bispecific molecules (Pullarkat V., et al., *Cancer Immunol Immunother* 48:9 (1999)) has been observed.

The calculated half-life of 11.1 hours is also within the range reported for other anti-CD64 based bispecific molecules (Curnow R. T., *Cancer Immunol Immunother* 45:210 (1997)). This half-life is shorter compared with humanized IgG-based antibodies such as rituximab, where a half-life of more than 400 hours has been described. However, the shorter half-life of H22xKi-4 is not surprising, since this new molecule is smaller when compared to an intact IgG-based antibody (104 kDa vs 180 kDa) and lacks the Fc-portion (Tobinai K. et al., *Ann Oncol* 9:527 (1998)). Furthermore, compared to intact antibodies, the molecular size of H22xKi-4 might more easily allow its penetration into the malignant lymph-nodes (Jain R. K., *Cancer Res*. 50 (Suppl) .:814s (1990)).

The schedule used in this study was designed to saturate all peripheral blood monocytes and sCD30 with the bispecific molecule resulting in an excess of unbound bispecific molecule that could then penetrate into the tissue to bind HRS-cells. Binding to sCD30 might have a major impact on the distribution of H22xKi-4. A significant accumulation of H22x-Ki-4 measured as peak-level and AUC was observed, suggesting saturation of this compartment. Furthermore, sCD30 remained at very low levels after the first infusion of H22xKi-4 during the whole treatment period, probably in part due to the blockade of CD30 shedding by the Ki-4 antibody (Horn-Lohrens O., et al., *Int J Cancer* 60:539 (1995)). In addition, binding of H22xKi-4 to the HRS-cells by immunohistochemistry was observed. Finally, a release of monocyte derived cytokines i.e. G-CSF, IL-6, IL-15, and TNFα combined with the profound binding of the bispecific molecule to CD64 on the effector cells was observed.

The promising response to H22xKi-4 corroborates data reported from solid tumors using the anti-FcγRI monoclonal antibody H22. Induction of ADCC via binding to CD64 was demonstrated in patients with advanced breast carcinoma (van Ojik H. H. et al, *Cancer Immunol Immunother* 45:207 (1997)). In hormone-refractory prostate carcinoma, the anti-CD64x anti-HER2 bispecific molecule showed activity even at lower doses than used in the present trial (James N. D. et al., *Br J Cancer* 85:152 (2001)).

Overall, the foregoing study demonstrates that the bispecific molecules of the present invention, e.g., H22xKi-4, show an excellent toxicity profile and a promising efficacy in patients with pretreated, advanced or refractory HD.

Equivalents

Those skilled in the art will recognize, or be able to ascertain using no more than routine experimentation, many equivalents of the specific embodiments of the invention described herein. Such equivalents are intended to be encompassed by the following claims.

Incorporation by Reference

All patents, pending patent applications and other publications cited herein are hereby incorporated by reference in their entirety.

SEQUENCE LISTING

```
<160> NUMBER OF SEQ ID NOS: 53

<210> SEQ ID NO 1
<211> LENGTH: 348
<212> TYPE: DNA
<213> ORGANISM: Homo sapiens
<220> FEATURE:
<221> NAME/KEY: CDS
<222> LOCATION: (1)...(348)

<400> SEQUENCE: 1 gag gtg cag ttg gtg gag tct ggg gga ggc ttg gtc cag cct ggg ggg      48
Glu Val Gln Leu Val Glu Ser Gly Gly Gly Leu Val Gln Pro Gly Gly
 1               5                  10                  15 tcc ctg aga ctc tcc tgt gta gcc tct gga ttc acc ttt agt aac tct      96
Ser Leu Arg Leu Ser Cys Val Ala Ser Gly Phe Thr Phe Ser Asn Ser
            20                  25                  30 tgg atg agc tgg gtc cgc cag gct cca ggg aaa ggg ctg gag tgg gtg     144
Trp Met Ser Trp Val Arg Gln Ala Pro Gly Lys Gly Leu Glu Trp Val
        35                  40                  45 gcc aac ata aac gaa gat gga agt gag aaa ttc tat gtg gac tct gtg     192
Ala Asn Ile Asn Glu Asp Gly Ser Glu Lys Phe Tyr Val Asp Ser Val
    50                  55                  60 aag ggc cga ttc acc ttc tcc aga gac aac gcc gag aac tca ctg tat     240
Lys Gly Arg Phe Thr Phe Ser Arg Asp Asn Ala Glu Asn Ser Leu Tyr
65                  70                  75                  80 ctg caa atg aac agc ctg aga gcc gag gac acg gct gtg tat tac tgt     288
Leu Gln Met Asn Ser Leu Arg Ala Glu Asp Thr Ala Val Tyr Tyr Cys
                85                  90                  95 gcg agg gtt cat tgg tac ttc cat ctc tgg ggc cgt ggc acc ctg gtc     336
Ala Arg Val His Trp Tyr Phe His Leu Trp Gly Arg Gly Thr Leu Val
            100                 105                 110 act gtc tcc tca                                                     348
Thr Val Ser Ser
        115

<210> SEQ ID NO 2
<211> LENGTH: 116
<212> TYPE: PRT
<213> ORGANISM: Homo sapiens

<400> SEQUENCE: 2

Glu Val Gln Leu Val Glu Ser Gly Gly Gly Leu Val Gln Pro Gly Gly
 1               5                  10                  15

Ser Leu Arg Leu Ser Cys Val Ala Ser Gly Phe Thr Phe Ser Asn Ser
            20                  25                  30

Trp Met Ser Trp Val Arg Gln Ala Pro Gly Lys Gly Leu Glu Trp Val
        35                  40                  45

Ala Asn Ile Asn Glu Asp Gly Ser Glu Lys Phe Tyr Val Asp Ser Val
```

-continued

Lys Gly Arg Phe Thr Phe Ser Arg Asp Asn Ala Glu Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Val His Trp Tyr Phe His Leu Trp Gly Arg Gly Thr Leu Val
            100                 105                 110

Thr Val Ser Ser
        115

<210> SEQ ID NO 3
<211> LENGTH: 324
<212> TYPE: DNA
<213> ORGANISM: Homo sapiens
<220> FEATURE:
<221> NAME/KEY: CDS
<222> LOCATION: (1)...(324)

<400> SEQUENCE: 3

```
gaa att gtg ttg acg cag tct cca ggc acc ctg tct ttg tct cca ggg      48
Glu Ile Val Leu Thr Gln Ser Pro Gly Thr Leu Ser Leu Ser Pro Gly
 1               5                  10                  15 gaa aga gcc acc ctc tcc tgc agg gcc agt cag agt gtt agc agc agc      96
Glu Arg Ala Thr Leu Ser Cys Arg Ala Ser Gln Ser Val Ser Ser Ser
            20                  25                  30 tac tta gcc tgg tac cag cag aaa cct ggc cag gct ccc agg ctc ctc     144
Tyr Leu Ala Trp Tyr Gln Gln Lys Pro Gly Gln Ala Pro Arg Leu Leu
        35                  40                  45 atc tat ggt gca tcc agc agg gcc act ggc atc cca gac agg ttc agt     192
Ile Tyr Gly Ala Ser Ser Arg Ala Thr Gly Ile Pro Asp Arg Phe Ser
    50                  55                  60 ggc agt ggg tct ggg aca gac ttc act ctc acc atc agc agc ctg gag     240
Gly Ser Gly Ser Gly Thr Asp Phe Thr Leu Thr Ile Ser Ser Leu Glu
 65                  70                  75                  80 cct gaa gat ttt gca gtg tat tac tgt cag cag tat ggt agc tca ccg     288
Pro Glu Asp Phe Ala Val Tyr Tyr Cys Gln Gln Tyr Gly Ser Ser Pro
                 85                  90                  95 tgg acg ttc ggc caa ggg acc aag gtg gaa atc aaa                     324
Trp Thr Phe Gly Gln Gly Thr Lys Val Glu Ile Lys
            100                 105
```

<210> SEQ ID NO 4
<211> LENGTH: 108
<212> TYPE: PRT
<213> ORGANISM: Homo sapiens

<400> SEQUENCE: 4

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Ser Leu Glu
 65                  70                  75                  80

Pro Glu Asp Phe Ala Val Tyr Tyr Cys Gln Gln Tyr Gly Ser Ser Pro
                 85                  90                  95

```
Trp Thr Phe Gly Gln Gly Thr Lys Val Glu Ile Lys
            100                 105
```

<210> SEQ ID NO 5
<211> LENGTH: 348
<212> TYPE: DNA
<213> ORGANISM: Homo sapiens
<220> FEATURE:
<221> NAME/KEY: CDS
<222> LOCATION: (1)...(348)

<400> SEQUENCE: 5

```
cag gtg cag cta cag cag tgg ggc gca gga ctg ttg aag cct tcg gag      48
Gln Val Gln Leu Gln Gln Trp Gly Ala Gly Leu Leu Lys Pro Ser Glu
 1               5                  10                  15 acc ctg tcc ctc acc tgc gct gtc tat ggt ggg tcc ttc agt ggt tac      96
Thr Leu Ser Leu Thr Cys Ala Val Tyr Gly Gly Ser Phe Ser Gly Tyr
            20                  25                  30 tac tgg agc tgg atc cgc cag ccc cca ggg aag ggg ctg gag tgg att     144
Tyr Trp Ser Trp Ile Arg Gln Pro Pro Gly Lys Gly Leu Glu Trp Ile
        35                  40                  45 ggg gaa atc aat cat agt gga agc acc aag tac acc ccg tcc ctc aag     192
Gly Glu Ile Asn His Ser Gly Ser Thr Lys Tyr Thr Pro Ser Leu Lys
    50                  55                  60 agc cga gtc acc ata tca gta gac acg tcc aag cac caa ttc tcc ctg     240
Ser Arg Val Thr Ile Ser Val Asp Thr Ser Lys His Gln Phe Ser Leu
 65                 70                  75                  80 aag ctg agc tct gtg acc gcc gcg gac acg gct gtg tat tac tgt gcg     288
Lys Leu Ser Ser Val Thr Ala Ala Asp Thr Ala Val Tyr Tyr Cys Ala
                85                  90                  95 aga gag act gtc tac tac ttc gat ctc tgg ggc cgt ggc acc ctg gtc     336
Arg Glu Thr Val Tyr Tyr Phe Asp Leu Trp Gly Arg Gly Thr Leu Val
            100                 105                 110 act gtc tcc tca                                                      348
Thr Val Ser Ser
        115
```

<210> SEQ ID NO 6
<211> LENGTH: 116
<212> TYPE: PRT
<213> ORGANISM: Homo sapiens

<400> SEQUENCE: 6

```
Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Lys Tyr Thr Pro Ser Leu Lys
    50                  55                  60

Ser Arg Val Thr Ile Ser Val Asp Thr Ser Lys His Gln Phe Ser Leu
 65                 70                  75                  80

Lys Leu Ser Ser Val Thr Ala Ala Asp Thr Ala Val Tyr Tyr Cys Ala
                85                  90                  95

Arg Glu Thr Val Tyr Tyr Phe Asp Leu Trp Gly Arg Gly Thr Leu Val
            100                 105                 110

Thr Val Ser Ser
        115
```

<210> SEQ ID NO 7
<211> LENGTH: 321
<212> TYPE: DNA
<213> ORGANISM: Homo sapiens
<220> FEATURE:
<221> NAME/KEY: CDS
<222> LOCATION: (1)...(321)

<400> SEQUENCE: 7

| gaa | att | gtg | ttg | aca | cag | tct | cca | gcc | acc | ctg | tct | ttg | tct | cca | ggg | 48 |
| Glu | Ile | Val | Leu | Thr | Gln | Ser | Pro | Ala | Thr | Leu | Ser | Leu | Ser | Pro | Gly | |
| 1   |     |     |     | 5   |     |     |     |     | 10  |     |     |     |     | 15  |     | |

| gaa | aga | gcc | acc | ctc | tcc | tgc | agg | gcc | agt | cag | agt | gta | agc | agc | aac | 96 |
| Glu | Arg | Ala | Thr | Leu | Ser | Cys | Arg | Ala | Ser | Gln | Ser | Val | Ser | Ser | Asn | |
|     |     |     | 20  |     |     |     |     | 25  |     |     |     |     | 30  |     |     | |

| tta | gcc | tgg | tac | caa | cag | aaa | cct | ggc | cag | gct | ccc | agg | ctc | ctc | atc | 144 |
| Leu | Ala | Trp | Tyr | Gln | Gln | Lys | Pro | Gly | Gln | Ala | Pro | Arg | Leu | Leu | Ile | |
|     | 35  |     |     |     |     | 40  |     |     |     |     | 45  |     |     |     |     | |

| tat | gat | gca | tcc | aac | agg | gcc | act | ggc | atc | cca | gcc | agg | ctc | agt | ggc | 192 |
| Tyr | Asp | Ala | Ser | Asn | Arg | Ala | Thr | Gly | Ile | Pro | Ala | Arg | Leu | Ser | Gly | |
| 50  |     |     |     |     | 55  |     |     |     |     | 60  |     |     |     |     |     | |

| agt | ggg | tct | ggg | aca | gac | ttc | act | ctc | acc | atc | agc | agc | cta | gag | cct | 240 |
| Ser | Gly | Ser | Gly | Thr | Asp | Phe | Thr | Leu | Thr | Ile | Ser | Ser | Leu | Glu | Pro | |
| 65  |     |     |     | 70  |     |     |     |     | 75  |     |     |     |     | 80  |     | |

| gaa | gat | ttt | gca | gtt | tat | tac | tgt | caa | cag | cgt | agc | aac | tgg | ccg | tgg | 288 |
| Glu | Asp | Phe | Ala | Val | Tyr | Tyr | Cys | Gln | Gln | Arg | Ser | Asn | Trp | Pro | Trp | |
|     |     |     |     | 85  |     |     |     |     | 90  |     |     |     |     | 95  |     | |

| acg | ttc | ggc | caa | ggg | acc | aag | gtg | gaa | atc | aaa | | 321 |
| Thr | Phe | Gly | Gln | Gly | Thr | Lys | Val | Glu | Ile | Lys | | |
|     |     |     | 100 |     |     |     |     | 105 |     |     | | |

<210> SEQ ID NO 8
<211> LENGTH: 107
<212> TYPE: PRT
<213> ORGANISM: Homo sapiens

<400> SEQUENCE: 8

| Glu | Ile | Val | Leu | Thr | Gln | Ser | Pro | Ala | Thr | Leu | Ser | Leu | Ser | Pro | Gly |
| 1   |     |     |     | 5   |     |     |     |     | 10  |     |     |     |     | 15  |     |

| Glu | Arg | Ala | Thr | Leu | Ser | Cys | Arg | Ala | Ser | Gln | Ser | Val | Ser | Ser | Asn |
|     |     |     | 20  |     |     |     |     | 25  |     |     |     |     | 30  |     |     |

| Leu | Ala | Trp | Tyr | Gln | Gln | Lys | Pro | Gly | Gln | Ala | Pro | Arg | Leu | Leu | Ile |
|     | 35  |     |     |     |     | 40  |     |     |     |     | 45  |     |     |     |     |

| Tyr | Asp | Ala | Ser | Asn | Arg | Ala | Thr | Gly | Ile | Pro | Ala | Arg | Leu | Ser | Gly |
| 50  |     |     |     |     | 55  |     |     |     |     | 60  |     |     |     |     |     |

| Ser | Gly | Ser | Gly | Thr | Asp | Phe | Thr | Leu | Thr | Ile | Ser | Ser | Leu | Glu | Pro |
| 65  |     |     |     | 70  |     |     |     |     | 75  |     |     |     |     | 80  |     |

| Glu | Asp | Phe | Ala | Val | Tyr | Tyr | Cys | Gln | Gln | Arg | Ser | Asn | Trp | Pro | Trp |
|     |     |     |     | 85  |     |     |     |     | 90  |     |     |     |     | 95  |     |

| Thr | Phe | Gly | Gln | Gly | Thr | Lys | Val | Glu | Ile | Lys |
|     |     |     | 100 |     |     |     |     | 105 |     |     |

<210> SEQ ID NO 9
<211> LENGTH: 336
<212> TYPE: DNA
<213> ORGANISM: Homo sapiens
<220> FEATURE:
<221> NAME/KEY: CDS
<222> LOCATION: (1)...(336)

<400> SEQUENCE: 9

| cag | gtg | cag | cta | cag | cag | tgg | ggc | gca | gga | ctg | ttg | aag | cct | tcg | gag | 48 |

```
                Gln Val Gln Leu Gln Gln Trp Gly Ala Gly Leu Leu Lys Pro Ser Glu
                  1               5                  10                  15 acc ctg tcc ctc acc tgc gct gtc tat ggt ggg tcc ttc agt gct tac         96
Thr Leu Ser Leu Thr Cys Ala Val Tyr Gly Gly Ser Phe Ser Ala Tyr
                 20                  25                  30 tac tgg agc tgg atc cgc cag ccc cca ggg aag ggg ctg gag tgg att        144
Tyr Trp Ser Trp Ile Arg Gln Pro Pro Gly Lys Gly Leu Glu Trp Ile
             35                  40                  45 ggg gac atc aat cat ggt gga ggc acc aac tac aac ccg tcc ctc aag        192
Gly Asp Ile Asn His Gly Gly Gly Thr Asn Tyr Asn Pro Ser Leu Lys
         50                  55                  60 agt cga gtc acc ata tca gta gac acg tcc aag aac cag ttc tcc ctg        240
Ser Arg Val Thr Ile Ser Val Asp Thr Ser Lys Asn Gln Phe Ser Leu
 65                  70                  75                  80 aag ctg aac tct gta acc gcc gcg gac acg gct gtg tat tac tgt gcg        288
Lys Leu Asn Ser Val Thr Ala Ala Asp Thr Ala Val Tyr Tyr Cys Ala
                 85                  90                  95 agc cta act gcc tac tgg ggc cag gga agc ctg gtc acc gtc tcc tca        336
Ser Leu Thr Ala Tyr Trp Gly Gln Gly Ser Leu Val Thr Val Ser Ser
            100                 105                 110

<210> SEQ ID NO 10
<211> LENGTH: 112
<212> TYPE: PRT
<213> ORGANISM: Homo sapiens

<400> SEQUENCE: 10

Gln Val Gln Leu Gln Gln Trp Gly Ala Gly Leu Leu Lys Pro Ser Glu
  1               5                  10                  15

Thr Leu Ser Leu Thr Cys Ala Val Tyr Gly Gly Ser Phe Ser Ala Tyr
                 20                  25                  30

Tyr Trp Ser Trp Ile Arg Gln Pro Pro Gly Lys Gly Leu Glu Trp Ile
             35                  40                  45

Gly Asp Ile Asn His Gly Gly Gly Thr Asn Tyr Asn Pro Ser Leu Lys
         50                  55                  60

Ser Arg Val Thr Ile Ser Val Asp Thr Ser Lys Asn Gln Phe Ser Leu
 65                  70                  75                  80

Lys Leu Asn Ser Val Thr Ala Ala Asp Thr Ala Val Tyr Tyr Cys Ala
                 85                  90                  95

Ser Leu Thr Ala Tyr Trp Gly Gln Gly Ser Leu Val Thr Val Ser Ser
            100                 105                 110

<210> SEQ ID NO 11
<211> LENGTH: 321
<212> TYPE: DNA
<213> ORGANISM: Homo sapiens
<220> FEATURE:
<221> NAME/KEY: CDS
<222> LOCATION: (1)...(321)

<400> SEQUENCE: 11 gac atc cag atg acc cag tct cca acc tca ctg tct gca tct gta gga         48
Asp Ile Gln Met Thr Gln Ser Pro Thr Ser Leu Ser Ala Ser Val Gly
  1               5                  10                  15 gac aga gtc acc atc act tgt cgg gcg agt cag ggt att agc agc tgg         96
Asp Arg Val Thr Ile Thr Cys Arg Ala Ser Gln Gly Ile Ser Ser Trp
                 20                  25                  30 tta acc tgg tat cag cag aaa cca gag aaa gcc cct aag tcc ctg atc        144
Leu Thr Trp Tyr Gln Gln Lys Pro Glu Lys Ala Pro Lys Ser Leu Ile
             35                  40                  45
```

```
tat gct gca tcc agt ttg caa agt ggg gtc cca tca agg ttc agc ggc    192
Tyr Ala Ala Ser Ser Leu Gln Ser Gly Val Pro Ser Arg Phe Ser Gly
         50                  55                  60 agt gga tct ggg aca gat ttc act ctc acc atc agc agc ctg cag cct    240
Ser Gly Ser Gly Thr Asp Phe Thr Leu Thr Ile Ser Ser Leu Gln Pro
 65                  70                  75                  80 gaa gat ttt gca act tat tac tgc caa cag tat gat agt tac cct atc    288
Glu Asp Phe Ala Thr Tyr Tyr Cys Gln Gln Tyr Asp Ser Tyr Pro Ile
                 85                  90                  95 acc ttc ggc caa ggg aca cga ctg gag att aaa                        321
Thr Phe Gly Gln Gly Thr Arg Leu Glu Ile Lys
            100                 105

<210> SEQ ID NO 12
<211> LENGTH: 107
<212> TYPE: PRT
<213> ORGANISM: Homo sapiens

<400> SEQUENCE: 12

Asp Ile Gln Met Thr Gln Ser Pro Thr Ser Leu Ser Ala Ser Val Gly
 1               5                   10                  15

Asp Arg Val Thr Ile Thr Cys Arg Ala Ser Gln Gly Ile Ser Ser Trp
             20                  25                  30

Leu Thr Trp Tyr Gln Gln Lys Pro Glu Lys Ala Pro Lys Ser Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asp Ser Tyr Pro Ile
                 85                  90                  95

Thr Phe Gly Gln Gly Thr Arg Leu Glu Ile Lys
            100                 105

<210> SEQ ID NO 13
<211> LENGTH: 15
<212> TYPE: DNA
<213> ORGANISM: Homo sapiens

<400> SEQUENCE: 13
aactcttgga tgagc                                                   15

<210> SEQ ID NO 14
<211> LENGTH: 5
<212> TYPE: PRT
<213> ORGANISM: Homo sapiens

<400> SEQUENCE: 14

Asn Ser Trp Met Ser
 1               5

<210> SEQ ID NO 15
<211> LENGTH: 51
<212> TYPE: DNA
<213> ORGANISM: Homo sapiens

<400> SEQUENCE: 15
aacataaacg aagatggaag tgagaaattc tatgtggact ctgtgaaggg c            51

<210> SEQ ID NO 16
<211> LENGTH: 17
```

```
<212> TYPE: PRT
<213> ORGANISM: Homo sapiens

<400> SEQUENCE: 16

Asn Ile Asn Glu Asp Gly Ser Glu Lys Phe Tyr Val Asp Ser Val Lys
 1               5                  10                  15

Gly

<210> SEQ ID NO 17
<211> LENGTH: 21
<212> TYPE: DNA
<213> ORGANISM: Homo sapiens

<400> SEQUENCE: 17
gttcattggt acttccatct c                                                     21

<210> SEQ ID NO 18
<211> LENGTH: 5
<212> TYPE: DNA
<213> ORGANISM: Homo sapiens

<400> SEQUENCE: 18 vhwyh                                                                        5

<210> SEQ ID NO 19
<211> LENGTH: 36
<212> TYPE: DNA
<213> ORGANISM: Homo sapiens

<400> SEQUENCE: 19
agggccagtc agagtgttag cagcagctac ttagcc                                     36

<210> SEQ ID NO 20
<211> LENGTH: 12
<212> TYPE: PRT
<213> ORGANISM: Homo sapiens

<400> SEQUENCE: 20

Arg Ala Ser Gln Ser Val Ser Ser Ser Tyr Leu Ala
 1               5                  10

<210> SEQ ID NO 21
<211> LENGTH: 21
<212> TYPE: DNA
<213> ORGANISM: Homo sapiens

<400> SEQUENCE: 21
ggtgcatcca gcagggccac t                                                     21

<210> SEQ ID NO 22
<211> LENGTH: 7
<212> TYPE: PRT
<213> ORGANISM: Homo sapiens

<400> SEQUENCE: 22

Gly Ala Ser Ser Arg Ala Thr
 1               5

<210> SEQ ID NO 23
<211> LENGTH: 27
<212> TYPE: DNA
<213> ORGANISM: Homo sapiens

<400> SEQUENCE: 23
```

```
cagcagtatg gtagctcacc gtggacg                                    27

<210> SEQ ID NO 24
<211> LENGTH: 9
<212> TYPE: PRT
<213> ORGANISM: Homo sapiens

<400> SEQUENCE: 24

Gln Gln Tyr Gly Ser Ser Pro Trp Thr
1               5

<210> SEQ ID NO 25
<211> LENGTH: 15
<212> TYPE: DNA
<213> ORGANISM: Homo sapiens

<400> SEQUENCE: 25
ggttactact ggagc                                                 15

<210> SEQ ID NO 26
<211> LENGTH: 5
<212> TYPE: PRT
<213> ORGANISM: Homo sapiens

<400> SEQUENCE: 26

Gly Tyr Tyr Trp Ser
1               5

<210> SEQ ID NO 27
<211> LENGTH: 48
<212> TYPE: DNA
<213> ORGANISM: Homo sapiens

<400> SEQUENCE: 27
gaaatcaatc atagtggaag caccaagtac accccgtccc tcaagagc             48

<210> SEQ ID NO 28
<211> LENGTH: 16
<212> TYPE: PRT
<213> ORGANISM: Homo sapiens

<400> SEQUENCE: 28

Glu Ile Asn His Ser Gly Ser Thr Lys Tyr Thr Pro Ser Leu Lys Ser
1               5                   10                  15

<210> SEQ ID NO 29
<211> LENGTH: 24
<212> TYPE: DNA
<213> ORGANISM: Homo sapiens

<400> SEQUENCE: 29
gagactgtct actacttcga tctc                                       24

<210> SEQ ID NO 30
<211> LENGTH: 8
<212> TYPE: PRT
<213> ORGANISM: Homo sapiens

<400> SEQUENCE: 30

Glu Thr Val Tyr Tyr Phe Asp Leu
1               5

<210> SEQ ID NO 31
```

```
<211> LENGTH: 33
<212> TYPE: DNA
<213> ORGANISM: Homo sapiens

<400> SEQUENCE: 31
agggccagtc agagtgtaag cagcaactta gcc                                   33

<210> SEQ ID NO 32
<211> LENGTH: 11
<212> TYPE: PRT
<213> ORGANISM: Homo sapiens

<400> SEQUENCE: 32

Arg Ala Ser Gln Ser Val Ser Ser Asn Leu Ala
 1               5                  10

<210> SEQ ID NO 33
<211> LENGTH: 21
<212> TYPE: DNA
<213> ORGANISM: Homo sapiens

<400> SEQUENCE: 33
gatgcatcca acagggccac t                                                21

<210> SEQ ID NO 34
<211> LENGTH: 7
<212> TYPE: PRT
<213> ORGANISM: Homo sapiens

<400> SEQUENCE: 34

Asp Ala Ser Asn Arg Ala Thr
 1               5

<210> SEQ ID NO 35
<211> LENGTH: 27
<212> TYPE: DNA
<213> ORGANISM: Homo sapiens

<400> SEQUENCE: 35
caacagcgta gcaactggcc gtggacg                                          27

<210> SEQ ID NO 36
<211> LENGTH: 9
<212> TYPE: PRT
<213> ORGANISM: Homo sapiens

<400> SEQUENCE: 36

Gln Gln Arg Ser Asn Trp Pro Trp Thr
 1               5

<210> SEQ ID NO 37
<211> LENGTH: 15
<212> TYPE: DNA
<213> ORGANISM: Homo sapiens

<400> SEQUENCE: 37
gcttactact ggagc                                                       15

<210> SEQ ID NO 38
<211> LENGTH: 5
<212> TYPE: PRT
<213> ORGANISM: Homo sapiens

<400> SEQUENCE: 38
```

Ala Tyr Tyr Trp Ser
1               5

<210> SEQ ID NO 39
<211> LENGTH: 48
<212> TYPE: DNA
<213> ORGANISM: Homo sapiens

<400> SEQUENCE: 39
gacatcaatc atggtggagg caccaactac aacccgtccc tcaagagt        48

<210> SEQ ID NO 40
<211> LENGTH: 16
<212> TYPE: PRT
<213> ORGANISM: Homo sapiens

<400> SEQUENCE: 40

Asp Ile Asn His Gly Gly Gly Thr Asn Tyr Asn Pro Ser Leu Lys Ser
1               5                   10                  15

<210> SEQ ID NO 41
<211> LENGTH: 12
<212> TYPE: DNA
<213> ORGANISM: Homo sapiens

<400> SEQUENCE: 41
ctaactgcct ac                                               12

<210> SEQ ID NO 42
<211> LENGTH: 4
<212> TYPE: PRT
<213> ORGANISM: Homo sapiens

<400> SEQUENCE: 42

Leu Thr Ala Tyr
 1

<210> SEQ ID NO 43
<211> LENGTH: 33
<212> TYPE: DNA
<213> ORGANISM: Homo sapiens

<400> SEQUENCE: 43
cgggcgagtc agggtattag cagctggtta acc                        33

<210> SEQ ID NO 44
<211> LENGTH: 11
<212> TYPE: PRT
<213> ORGANISM: Homo sapiens

<400> SEQUENCE: 44

Arg Ala Ser Gln Gly Ile Ser Ser Trp Leu Thr
1               5                   10

<210> SEQ ID NO 45
<211> LENGTH: 21
<212> TYPE: DNA
<213> ORGANISM: Homo sapiens

<400> SEQUENCE: 45
gctgcatcca gtttgcaaag t                                     21

<210> SEQ ID NO 46
<211> LENGTH: 7

<212> TYPE: PRT
<213> ORGANISM: Homo sapiens

<400> SEQUENCE: 46

Ala Ala Ser Ser Leu Gln Ser
 1               5

<210> SEQ ID NO 47
<211> LENGTH: 27
<212> TYPE: DNA
<213> ORGANISM: Homo sapiens

<400> SEQUENCE: 47
caacagtatg atagttaccc tatcacc                                              27

<210> SEQ ID NO 48
<211> LENGTH: 9
<212> TYPE: PRT
<213> ORGANISM: Homo sapiens

<400> SEQUENCE: 48

Gln Gln Tyr Asp Ser Tyr Pro Ile Thr
 1               5

<210> SEQ ID NO 49
<211> LENGTH: 291
<212> TYPE: DNA
<213> ORGANISM: Homo sapiens

<400> SEQUENCE: 49
caggtgcagc tacagcagtg gggcgcagga ctgttgaagc cttcggagac cctgtccctc          60
acctgcgctg tctatggtgg gtccttcagt ggttactact ggagctggat ccgccagccc         120
ccagggaagg ggctggagtg gattggggaa atcaatcata gtggaagcac caactacaac         180
ccgtccctca agagtcgagt caccatatca gtagacacgt ccaagaacca gttctccctg         240
aagctgagct ctgtgaccgc cgcggacacg gctgtgtatt actgtgcgag a                  291

<210> SEQ ID NO 50
<211> LENGTH: 285
<212> TYPE: DNA
<213> ORGANISM: Homo sapiens

<400> SEQUENCE: 50
gacatccaga tgacccagtc tccatcctca ctgtctgcat ctgtaggaga cagagtcacc          60
atcacttgtc gggcgagtca gggtattagc agctggttag cctggtatca gcagaaacca         120
gagaaagccc ctaagtccct gatctatgct gcatccagtt tgcaaagtgg gtcccatca          180 aggttcagcg gcagtggatc tgggacagat ttcactctca ccatcagcag cctgcagcct         240
gaagattttg caacttatta ctgccaacag tataatagtt accct                         285

<210> SEQ ID NO 51
<211> LENGTH: 294
<212> TYPE: DNA
<213> ORGANISM: Homo sapiens

<400> SEQUENCE: 51
gaggtgcagc tggtggagtc tgggggaggc ttggtccagc ctgggggtc cctgagactc          60 tcctgtgcag cctctggatt cacctttagt agcattgga tgagctgggt ccgccaggct         120
ccagggaaag ggctggagtg ggtggccaac ataaagcaag atggaagtga gaaatactat         180

-continued

```
gtggactctg tgaagggccg attcaccatc tccagagaca acgccaagaa ctcactgtat        240
ctgcaaatga acagcctgag agccgaggac acggctgtgt attactgtgc gaga             294

<210> SEQ ID NO 52
<211> LENGTH: 288
<212> TYPE: DNA
<213> ORGANISM: Homo sapiens

<400> SEQUENCE: 52
gaaattgtgt tgacgcagtc tccaggcacc ctgtctttgt ctccagggga aagagccacc        60
ctctcctgca gggccagtca gagtgttagc agcagctact tagcctggta ccagcagaaa       120
cctggccagg ctcccaggct cctcatctat ggtgcatcca gcagggccac tggcatccca       180
gacaggttca gtggcagtgg gtctgggaca gacttcactc tcaccatcag cagactggag       240
cctgaagatt ttgcagtgta ttactgtcag cagtatggta gctcacct                    288

<210> SEQ ID NO 53
<211> LENGTH: 285
<212> TYPE: DNA
<213> ORGANISM: Homo sapiens

<400> SEQUENCE: 53
gaaattgtgt tgacacagtc tccagccacc ctgtctttgt ctccagggga aagagccacc        60
ctctcctgca gggccagtca gagtgttagc agctacttag cctggtacca acagaaacct       120
ggccaggctc ccaggctcct catctatgat gcatccaaca gggccactgg catcccagcc       180
aggttcagtg gcagtgggtc tgggacagac ttcactctca ccatcagcag cctagagcct       240
gaagattttg cagtttatta ctgtcagcag cgtagcaact ggcct                       285
```

We claim:

1. An isolated monoclonal antibody which binds to human CD30, wherein the antibody comprises a heavy chain variable region comprising CDR1, CD2, and CDR3 sequences comprising amino acid sequences SEQ ID NOs: 16, 17, and 18, respectively, and a light chain variable region comprising CDR1, CDR2, and CDR3 sequences comprising amino acid sequences SEQ ID NOs: 22, 23, and 24, respectively.

2. An isolated monoclonal antibody which binds to human CD30, wherein the antibody comprises a heavy chain variable region comprising CDR1, CDR2, and CDR3 sequences comprising amino acid sequences SEQ ID NOs: 28, 29, and 30, respectively, and a light chain variable region comprising CDR1, CD2, and CDR3 sequences comprising amino acid sequences SEQ ID NOs: 34, 35, and 36, respectively.

3. An isolated monoclonal antibody which binds to human CD30, wherein the antibody comprises a heavy chain variable region comprising CDR1, CDR2, and CDR3 sequences comprising amino acid sequences SEQ ID NOs: 40, 41, and 42, respectively, and a light chain variable region comprising CDR1, CD2, and CDR3 sequences comprising amino acid sequences SEQ ID NOs: 46, 47, and 48, respectively.

4. An isolated monoclonal antibody comprising heavy chain and light chain variable regions comprising the amino acid sequences shown in SEQ ID NO:2 and SEQ ID NO:4, respectively.

5. An isolated monoclonal antibody comprising heavy chain and light chain variable regions comprising the amino acid sequences shown in SEQ ID NO: 6 and SEQ ID NO:8, respectively.

6. An isolated monoclonal antibody comprising heavy chain and light chain variable regions comprising the amino acid sequences shown in SEQ ID NO: 10 and SEQ ID NO:12, respectively.

7. An isolated monoclonal antibody which binds to human Cd30, comprising a heavy chain variable region and a light chain variable region, wherein the heavy chain variable region comprises an amino acid sequence selected from the group consisting of SEQ ID NOs: 2, 6, and 10.

8. An isolated monoclonal antibody which binds to human Cd30, comprising a heavy chain variable region and a light chain variable region, wherein the light chain variable region comprises an amino acid sequence selected from the group consisting of SEQ ID NOs: 4, 8, and 12.

9. The antibody of any one of claims 1, 2, 3, 7, or 8, wherein the antibody has at least one of the following features:

(a) the antibody binds to human Cd30 with an affinity constant of at least $10^7$ M$^{-1}$;

(b) the antibody induces antibody dependent cellular cytotoxicity (ADCC) of tumor cells expressing Cd30 in the presence of effector cells; or (c) the antibody inhibits growth of a tumor cell expressing Cd30.

10. The antibody of claim 9, wherein the tumor cell is selected from the group consisting of bone marrow cells, liver cells, lymph node cells, skin cells, spleen cells, thymus cells, tonsil cells, decidua cells, endometrial cells, Hodgkin's cells, Reed-Steinberg cells, anaplastic large-cell lymphoma (ALCL) cells, pleomorphic and immunoblastic lymphoma cells, T cells, B cells, NK cells and monocytes.

11. The antibody of claim 9, wherein the tumor cell is a Hodgkin's cell or a Reed-Steinberg cell.

12. The antibody of any one of claims 1, 2, 3, 7, or 8 produced by a hybridoma, wherein the hybridoma is prepared from a B cell obtained from a transgenic non-human animal which has been immunized with Cd30 antigen and has a genome comprising a heavy chain transgene or transchromosome and a light chain transgene or transchromosome, fused to an immortalized cell.

13. A pharmaceutical composition comprising the antibody of any one of claims 1, 2, 3, 7, or 8 and a pharmaceutically acceptable carrier.

14. An immunoconjugate comprising the antibody according to any one of claims 1, 2, 3, 7, or 8 linked to a therapeutic agent.

15. A pharmaceutical composition comprising the immunoconjugate of claim 14 and a pharmaceutically acceptable carrier.

* * * * *

UNITED STATES PATENT AND TRADEMARK OFFICE
CERTIFICATE OF CORRECTION

| | |
|---|---|
| PATENT NO. | : 7,387,776 B2 |
| APPLICATION NO. | : 10/338366 |
| DATED | : June 17, 2008 |
| INVENTOR(S) | : Tibor Keler et al. |

It is certified that error appears in the above-identified patent and that said Letters Patent is hereby corrected as shown below:

Column 59, Line 52:
"DIQMTQSPATIENTSLSASVGDRVTITCRASQGISSWLTWYQQKPEKAP" should be -- DIQMTQSPTSLSASVGDRVTITCRASQGISSWLTWYQQKPEKAP --

Signed and Sealed this

Third Day of February, 2009

JOHN DOLL
*Acting Director of the United States Patent and Trademark Office*

In the Sequence Listing insert beginning col. 67 line 18:

Please replace the Sequence Listing contained in the above-identified issued patent with the corrected Sequence Listing set forth below.

```
-- <110> Keler, Tibor
        Graziano, Robert
        Treml, John

<120> HUMAN MONOCLONAL ANTIBODIES AGAINST CD30

<130> MXI-180RCE

<140> US 10/338,366
    <141> 2003-01-07

<150> US 60/347649
    <151> 2002-01-09

<150> US 60/404427
    <151> 2002-08-19

<150> US 60/431684
    <151> 2002-12-06

<160> 53

<170> FastSEQ for Windows Version 4.0

<210> 1
    <211> 348
    <212> DNA
    <213> Homo sapiens

<220>
    <221> CDS
    <222> (1)...(348)
```

<400> 1

| gag | gtg | cag | ttg | gtg | gag | tct | ggg | gga | ggc | ttg | gtc | cag | cct | ggg | ggg | 48 |
| Glu | Val | Gln | Leu | Val | Glu | Ser | Gly | Gly | Gly | Leu | Val | Gln | Pro | Gly | Gly | |
| 1 | | | | 5 | | | | | 10 | | | | | 15 | | |

| tcc | ctg | aga | ctc | tcc | tgt | gta | gcc | tct | gga | ttc | acc | ttt | agt | aac | tct | 96 |
| Ser | Leu | Arg | Leu | Ser | Cys | Val | Ala | Ser | Gly | Phe | Thr | Phe | Ser | Asn | Ser | |
| | | | 20 | | | | | 25 | | | | | 30 | | | |

| tgg | atg | agc | tgg | gtc | cgc | cag | gct | cca | ggg | aaa | ggg | ctg | gag | tgg | gtg | 144 |
| Trp | Met | Ser | Trp | Val | Arg | Gln | Ala | Pro | Gly | Lys | Gly | Leu | Glu | Trp | Val | |
| | | 35 | | | | | 40 | | | | | 45 | | | | |

| gcc | aac | ata | aac | gaa | gat | gga | agt | gag | aaa | ttc | tat | gtg | gac | tct | gtg | 192 |
| Ala | Asn | Ile | Asn | Glu | Asp | Gly | Ser | Glu | Lys | Phe | Tyr | Val | Asp | Ser | Val | |
| | 50 | | | | | 55 | | | | | 60 | | | | | |

| aag | ggc | cga | ttc | acc | ttc | tcc | aga | gac | aac | gcc | gag | aac | tca | ctg | tat | 240 |
| Lys | Gly | Arg | Phe | Thr | Phe | Ser | Arg | Asp | Asn | Ala | Glu | Asn | Ser | Leu | Tyr | |
| 65 | | | | | 70 | | | | | 75 | | | | | 80 | |

| ctg | caa | atg | aac | agc | ctg | aga | gcc | gag | gac | acg | gct | gtg | tat | tac | tgt | 288 |
| Leu | Gln | Met | Asn | Ser | Leu | Arg | Ala | Glu | Asp | Thr | Ala | Val | Tyr | Tyr | Cys | |
| | | | | 85 | | | | | 90 | | | | | 95 | | |

| gcg | agg | gtt | cat | tgg | tac | ttc | cat | ctc | tgg | ggc | cgt | ggc | acc | ctg | gtc | 336 |
| Ala | Arg | Val | His | Trp | Tyr | Phe | His | Leu | Trp | Gly | Arg | Gly | Thr | Leu | Val | |
| | | | 100 | | | | | 105 | | | | | 110 | | | |

| act | gtc | tcc | tca | | | | | | | | | | | | | 348 |
| Thr | Val | Ser | Ser | | | | | | | | | | | | | |
| | | 115 | | | | | | | | | | | | | | |

<210> 2
<211> 116

```
<212> PRT
<213> Homo sapiens

<400> 2
Glu Val Gln Leu Val Glu Ser Gly Gly Leu Val Gln Pro Gly Gly
 1               5                  10                  15
Ser Leu Arg Leu Ser Cys Val Ala Ser Gly Phe Thr Phe Ser Asn Ser
            20                  25                  30
Trp Met Ser Trp Val Arg Gln Ala Pro Gly Lys Gly Leu Glu Trp Val
        35                  40                  45
Ala Asn Ile Asn Glu Asp Gly Ser Glu Lys Phe Tyr Val Asp Ser Val
    50                  55                  60
Lys Gly Arg Phe Thr Phe Ser Arg Asp Asn Ala Glu Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Val His Trp Tyr Phe His Leu Trp Gly Arg Gly Thr Leu Val
            100                 105                 110
Thr Val Ser Ser
        115

<210> 3
<211> 324
<212> DNA
<213> Homo sapiens

<220>
<221> CDS
<222> (1)...(324)

<400> 3
gaa att gtg ttg acg cag tct cca ggc acc ctg tct ttg tct cca ggg    48
Glu Ile Val Leu Thr Gln Ser Pro Gly Thr Leu Ser Leu Ser Pro Gly
 1               5                  10                  15 gaa aga gcc acc ctc tcc tgc agg gcc agt cag agt gtt agc agc agc    96
Glu Arg Ala Thr Leu Ser Cys Arg Ala Ser Gln Ser Val Ser Ser Ser
            20                  25                  30 tac tta gcc tgg tac cag cag aaa cct ggc cag gct ccc agg ctc ctc   144
Tyr Leu Ala Trp Tyr Gln Gln Lys Pro Gly Gln Ala Pro Arg Leu Leu
        35                  40                  45 atc tat ggt gca tcc agc agg gcc act ggc atc cca gac agg ttc agt   192
Ile Tyr Gly Ala Ser Ser Arg Ala Thr Gly Ile Pro Asp Arg Phe Ser
    50                  55                  60 ggc agt ggg tct ggg aca gac ttc act ctc acc atc agc agc ctg gag   240
Gly Ser Gly Ser Gly Thr Asp Phe Thr Leu Thr Ile Ser Ser Leu Glu
65                  70                  75                  80
```

```
cct gaa gat ttt gca gtg tat tac tgt cag cag tat ggt agc tca ccg      288
Pro Glu Asp Phe Ala Val Tyr Tyr Cys Gln Gln Tyr Gly Ser Ser Pro
                85                  90                  95 tgg acg ttc ggc caa ggg acc aag gtg gaa atc aaa                      324
Trp Thr Phe Gly Gln Gly Thr Lys Val Glu Ile Lys
            100                 105
```

<210> 4
<211> 108
<212> PRT
<213> Homo sapiens

<400> 4

```
Glu Ile Val Leu Thr Gln Ser Pro Gly Thr Leu Ser Leu Ser Pro Gly
 1               5                  10                  15
Glu Arg Ala Thr Leu Ser Cys Arg Ala Ser Gln Ser Val Ser Ser Ser
            20                  25                  30
Tyr Leu Ala Trp Tyr Gln Gln Lys Pro Gly Gln Ala Pro Arg Leu Leu
        35                  40                  45
Ile Tyr Gly Ala Ser Ser Arg Ala Thr Gly Ile Pro Asp Arg Phe Ser
    50                  55                  60
Gly Ser Gly Ser Gly Thr Asp Phe Thr Leu Thr Ile Ser Ser Leu Glu
65                  70                  75                  80
Pro Glu Asp Phe Ala Val Tyr Tyr Cys Gln Gln Tyr Gly Ser Ser Pro
                85                  90                  95
Trp Thr Phe Gly Gln Gly Thr Lys Val Glu Ile Lys
            100                 105
```

<210> 5
<211> 348
<212> DNA
<213> Homo sapiens

<220>
<221> CDS
<222> (1)...(348)

<400> 5

```
cag gtg cag cta cag cag tgg ggc gca gga ctg ttg aag cct tcg gag      48
Gln Val Gln Leu Gln Gln Trp Gly Ala Gly Leu Leu Lys Pro Ser Glu
 1               5                  10                  15 acc ctg tcc ctc acc tgc gct gtc tat ggt ggg tcc ttc agt ggt tac      96
Thr Leu Ser Leu Thr Cys Ala Val Tyr Gly Gly Ser Phe Ser Gly Tyr
            20                  25                  30
```

```
tac tgg agc tgg atc cgc cag ccc cca ggg aag ggg ctg gag tgg att    144
Tyr Trp Ser Trp Ile Arg Gln Pro Pro Gly Lys Gly Leu Glu Trp Ile
            35                  40                  45 ggg gaa atc aat cat agt gga agc acc aag tac acc ccg tcc ctc aag    192
Gly Glu Ile Asn His Ser Gly Ser Thr Lys Tyr Thr Pro Ser Leu Lys
        50                  55                  60 agc cga gtc acc ata tca gta gac acg tcc aag cac caa ttc tcc ctg    240
Ser Arg Val Thr Ile Ser Val Asp Thr Ser Lys His Gln Phe Ser Leu
65                  70                  75                  80 aag ctg agc tct gtg acc gcc gcg gac acg gct gtg tat tac tgt gcg    288
Lys Leu Ser Ser Val Thr Ala Ala Asp Thr Ala Val Tyr Tyr Cys Ala
                    85                  90                  95 aga gag act gtc tac tac ttc gat ctc tgg ggc cgt ggc acc ctg gtc    336
Arg Glu Thr Val Tyr Tyr Phe Asp Leu Trp Gly Arg Gly Thr Leu Val
                100                 105                 110 act gtc tcc tca                                                    348
Thr Val Ser Ser
        115

<210> 6
<211> 116
<212> PRT
<213> Homo sapiens

<400> 6
Gln Val Gln Leu Gln Gln Trp Gly Ala Gly Leu Leu Lys Pro Ser Glu
1               5                   10                  15
Thr Leu Ser Leu Thr Cys Ala Val Tyr Gly Gly Ser Phe Ser Gly Tyr
            20                  25                  30
Tyr Trp Ser Trp Ile Arg Gln Pro Pro Gly Lys Gly Leu Glu Trp Ile
            35                  40                  45
Gly Glu Ile Asn His Ser Gly Ser Thr Lys Tyr Thr Pro Ser Leu Lys
        50                  55                  60
Ser Arg Val Thr Ile Ser Val Asp Thr Ser Lys His Gln Phe Ser Leu
65                  70                  75                  80
Lys Leu Ser Ser Val Thr Ala Ala Asp Thr Ala Val Tyr Tyr Cys Ala
                    85                  90                  95
Arg Glu Thr Val Tyr Tyr Phe Asp Leu Trp Gly Arg Gly Thr Leu Val
                100                 105                 110
Thr Val Ser Ser
        115

<210> 7
<211> 321
<212> DNA
```

```
<213> Homo sapiens

<220>
<221> CDS
<222> (1)...(321)

<400> 7
gaa att gtg ttg aca cag tct cca gcc acc ctg tct ttg tct cca ggg    48
Glu Ile Val Leu Thr Gln Ser Pro Ala Thr Leu Ser Leu Ser Pro Gly
 1               5                  10                  15 gaa aga gcc acc ctc tcc tgc agg gcc agt cag agt gta agc agc aac    96
Glu Arg Ala Thr Leu Ser Cys Arg Ala Ser Gln Ser Val Ser Ser Asn
            20                  25                  30 tta gcc tgg tac caa cag aaa cct ggc cag gct ccc agg ctc ctc atc   144
Leu Ala Trp Tyr Gln Gln Lys Pro Gly Gln Ala Pro Arg Leu Leu Ile
         35                  40                  45 tat gat gca tcc aac agg gcc act ggc atc cca gcc agg ctc agt ggc   192
Tyr Asp Ala Ser Asn Arg Ala Thr Gly Ile Pro Ala Arg Leu Ser Gly
     50                  55                  60 agt ggg tct ggg aca gac ttc act ctc acc atc agc agc cta gag cct   240
Ser Gly Ser Gly Thr Asp Phe Thr Leu Thr Ile Ser Ser Leu Glu Pro
 65                  70                  75                  80 gaa gat ttt gca gtt tat tac tgt caa cag cgt agc aac tgg ccg tgg   288
Glu Asp Phe Ala Val Tyr Tyr Cys Gln Gln Arg Ser Asn Trp Pro Trp
                 85                  90                  95 acg ttc ggc caa ggg acc aag gtg gaa atc aaa                        321
Thr Phe Gly Gln Gly Thr Lys Val Glu Ile Lys
             100                 105

<210> 8
<211> 107
<212> PRT
<213> Homo sapiens

<400> 8
Glu Ile Val Leu Thr Gln Ser Pro Ala Thr Leu Ser Leu Ser Pro Gly
 1               5                  10                  15
Glu Arg Ala Thr Leu Ser Cys Arg Ala Ser Gln Ser Val Ser Ser Asn
            20                  25                  30
Leu Ala Trp Tyr Gln Gln Lys Pro Gly Gln Ala Pro Arg Leu Leu Ile
         35                  40                  45
Tyr Asp Ala Ser Asn Arg Ala Thr Gly Ile Pro Ala Arg Leu Ser Gly
     50                  55                  60
Ser Gly Ser Gly Thr Asp Phe Thr Leu Thr Ile Ser Ser Leu Glu Pro
 65                  70                  75                  80
```

```
Glu Asp Phe Ala Val Tyr Tyr Cys Gln Gln Arg Ser Asn Trp Pro Trp
                85                  90                  95
Thr Phe Gly Gln Gly Thr Lys Val Glu Ile Lys
            100                 105
```

<210> 9
<211> 336
<212> DNA
<213> Homo sapiens

<220>
<221> CDS
<222> (1)...(336)

<400> 9
```
cag gtg cag cta cag cag tgg ggc gca gga ctg ttg aag cct tcg gag    48
Gln Val Gln Leu Gln Gln Trp Gly Ala Gly Leu Leu Lys Pro Ser Glu
 1               5                  10                  15 acc ctg tcc ctc acc tgc gct gtc tat ggt ggg tcc ttc agt gct tac    96
Thr Leu Ser Leu Thr Cys Ala Val Tyr Gly Gly Ser Phe Ser Ala Tyr
                20                  25                  30 tac tgg agc tgg atc cgc cag ccc cca ggg aag ggg ctg gag tgg att   144
Tyr Trp Ser Trp Ile Arg Gln Pro Pro Gly Lys Gly Leu Glu Trp Ile
            35                  40                  45 ggg gac atc aat cat ggt gga ggc acc aac tac aac ccg tcc ctc aag   192
Gly Asp Ile Asn His Gly Gly Gly Thr Asn Tyr Asn Pro Ser Leu Lys
     50                  55                  60 agt cga gtc acc ata tca gta gac acg tcc aag aac cag ttc tcc ctg   240
Ser Arg Val Thr Ile Ser Val Asp Thr Ser Lys Asn Gln Phe Ser Leu
 65                  70                  75                  80 aag ctg aac tct gta acc gcc gcg gac acg gct gtg tat tac tgt gcg   288
Lys Leu Asn Ser Val Thr Ala Ala Asp Thr Ala Val Tyr Tyr Cys Ala
                85                  90                  95 agc cta act gcc tac tgg ggc cag gga agc ctg gtc acc gtc tcc tca   336
Ser Leu Thr Ala Tyr Trp Gly Gln Gly Ser Leu Val Thr Val Ser Ser
            100                 105                 110
```

<210> 10
<211> 112
<212> PRT
<213> Homo sapiens

<400> 10
```
Gln Val Gln Leu Gln Gln Trp Gly Ala Gly Leu Leu Lys Pro Ser Glu
```

```
      1                   5                      10                    15
Thr Leu Ser Leu Thr Cys Ala Val Tyr Gly Gly Ser Phe Ser Ala Tyr
                    20                    25                    30
Tyr Trp Ser Trp Ile Arg Gln Pro Pro Gly Lys Gly Leu Glu Trp Ile
                    35                    40                    45
Gly Asp Ile Asn His Gly Gly Thr Asn Tyr Asn Pro Ser Leu Lys
            50                    55                    60
Ser Arg Val Thr Ile Ser Val Asp Thr Ser Lys Asn Gln Phe Ser Leu
 65                    70                    75                   80
Lys Leu Asn Ser Val Thr Ala Ala Asp Thr Ala Val Tyr Tyr Cys Ala
                    85                    90                    95
Ser Leu Thr Ala Tyr Trp Gly Gln Gly Ser Leu Val Thr Val Ser Ser
                   100                   105                   110
```

<210> 11
<211> 321
<212> DNA
<213> Homo sapiens

<220>
<221> CDS
<222> (1)...(321)

<400> 11

```
gac atc cag atg acc cag tct cca acc tca ctg tct gca tct gta gga      48
Asp Ile Gln Met Thr Gln Ser Pro Thr Ser Leu Ser Ala Ser Val Gly
 1               5                  10                  15 gac aga gtc acc atc act tgt cgg gcg agt cag ggt att agc agc tgg      96
Asp Arg Val Thr Ile Thr Cys Arg Ala Ser Gln Gly Ile Ser Ser Trp
              20                  25                  30 tta acc tgg tat cag cag aaa cca gag aaa gcc cct aag tcc ctg atc     144
Leu Thr Trp Tyr Gln Gln Lys Pro Glu Lys Ala Pro Lys Ser Leu Ile
         35                  40                  45 tat gct gca tcc agt ttg caa agt ggg gtc cca tca agg ttc agc ggc     192
Tyr Ala Ala Ser Ser Leu Gln Ser Gly Val Pro Ser Arg Phe Ser Gly
     50                  55                  60 agt gga tct ggg aca gat ttc act ctc acc atc agc agc ctg cag cct     240
Ser Gly Ser Gly Thr Asp Phe Thr Leu Thr Ile Ser Ser Leu Gln Pro
 65                  70                  75                  80 gaa gat ttt gca act tat tac tgc caa cag tat gat agt tac cct atc     288
Glu Asp Phe Ala Thr Tyr Tyr Cys Gln Gln Tyr Asp Ser Tyr Pro Ile
              85                  90                  95 acc ttc ggc caa ggg aca cga ctg gag att aaa                         321
Thr Phe Gly Gln Gly Thr Arg Leu Glu Ile Lys
         100                 105
```

```
<210> 12
<211> 107
<212> PRT
<213> Homo sapiens

<400> 12
Asp Ile Gln Met Thr Gln Ser Pro Thr Ser Leu Ser Ala Ser Val Gly
1               5                   10                  15
Asp Arg Val Thr Ile Thr Cys Arg Ala Ser Gln Gly Ile Ser Ser Trp
            20                  25                  30
Leu Thr Trp Tyr Gln Gln Lys Pro Glu Lys Ala Pro Lys Ser Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Asp Ser Tyr Pro Ile
                85                  90                  95
Thr Phe Gly Gln Gly Thr Arg Leu Glu Ile Lys
            100                 105

<210> 13
<211> 15
<212> DNA
<213> Homo sapiens

<400> 13
aactcttgga tgagc

<210> 14
<211> 51
<212> DNA
<213> Homo sapiens

<400> 14
aacataaacg aagatggaag tgagaaattc tatgtggact ctgtgaaggg c

<210> 15
<211> 21
<212> DNA
<213> Homo sapiens

<400> 15
gttcattggt acttccatct c

<210> 16
<211> 5
```

<212> PRT
<213> Homo sapiens

<400> 16
Asn Ser Trp Met Ser
 1               5

<210> 17
<211> 17
<212> PRT
<213> Homo sapiens

<400> 17
Asn Ile Asn Glu Asp Gly Ser Glu Lys Phe Tyr Val Asp Ser Val Lys
 1               5                  10                  15
Gly

<210> 18
<211> 7
<212> PRT
<213> Homo sapiens

<400> 18
Val His Trp Tyr Phe His Leu
 1               5

<210> 19
<211> 36
<212> DNA
<213> Homo sapiens

<400> 19
agggccagtc agagtgttag cagcagctac ttagcc

<210> 20
<211> 21
<212> DNA
<213> Homo sapiens

<400> 20
ggtgcatcca gcagggccac t

<210> 21
<211> 27
<212> DNA
<213> Homo sapiens

<400> 21
cagcagtatg gtagctcacc gtggacg

<210> 22
<211> 12
<212> PRT
<213> Homo sapiens

<400> 22
Arg Ala Ser Gln Ser Val Ser Ser Ser Tyr Leu Ala
1               5                   10

<210> 23
<211> 7
<212> PRT
<213> Homo sapiens

<400> 23
Gly Ala Ser Ser Arg Ala Thr
1               5

<210> 24
<211> 9
<212> PRT
<213> Homo sapiens

<400> 24
Gln Gln Tyr Gly Ser Ser Pro Trp Thr
1               5

<210> 25
<211> 15
<212> DNA
<213> Homo sapiens

<400> 25
ggttactact ggagc

<210> 26
<211> 48
<212> DNA
<213> Homo sapiens

<400> 26
gaaatcaatc atagtggaag caccaagtac accccgtccc tcaagagc

<210> 27

```
<211> 24
<212> DNA
<213> Homo sapiens

<400> 27
gagactgtct actacttcga tctc

<210> 28
<211> 5
<212> PRT
<213> Homo sapiens

<400> 28
Gly Tyr Tyr Trp Ser
 1               5

<210> 29
<211> 16
<212> PRT
<213> Homo sapiens

<400> 29
Glu Ile Asn His Ser Gly Ser Thr Lys Tyr Thr Pro Ser Leu Lys Ser
 1               5                  10                  15

<210> 30
<211> 8
<212> PRT
<213> Homo sapiens

<400> 30
Glu Thr Val Tyr Tyr Phe Asp Leu
 1               5

<210> 31
<211> 33
<212> DNA
<213> Homo sapiens

<400> 31
agggccagtc agagtgtaag cagcaactta gcc

<210> 32
<211> 21
<212> DNA
<213> Homo sapiens
```

```
<400> 32
gatgcatcca acagggccac t

<210> 33
<211> 27
<212> DNA
<213> Homo sapiens

<400> 33
caacagcgta gcaactggcc gtggacg

<210> 34
<211> 11
<212> PRT
<213> Homo sapiens

<400> 34
Arg Ala Ser Gln Ser Val Ser Ser Asn Leu Ala
 1               5                   10

<210> 35
<211> 7
<212> PRT
<213> Homo sapiens

<400> 35
Asp Ala Ser Asn Arg Ala Thr
 1               5

<210> 36
<211> 9
<212> PRT
<213> Homo sapiens

<400> 36
Gln Gln Arg Ser Asn Trp Pro Trp Thr
 1               5

<210> 37
<211> 15
<212> DNA
<213> Homo sapiens

<400> 37
gcttactact ggagc
```

```
<210> 38
<211> 48
<212> DNA
<213> Homo sapiens

<400> 38
gacatcaatc atggtggagg caccaactac aacccgtccc tcaagagt

<210> 39
<211> 12
<212> DNA
<213> Homo sapiens

<400> 39
ctaactgcct ac

<210> 40
<211> 5
<212> PRT
<213> Homo sapiens

<400> 40
Ala Tyr Tyr Trp Ser
 1               5

<210> 41
<211> 16
<212> PRT
<213> Homo sapiens

<400> 41
Asp Ile Asn His Gly Gly Gly Thr Asn Tyr Asn Pro Ser Leu Lys Ser
 1               5                  10                  15

<210> 42
<211> 4
<212> PRT
<213> Homo sapiens

<400> 42
Leu Thr Ala Tyr
 1

<210> 43
<211> 33
<212> DNA
<213> Homo sapiens
```

```
<400> 43
cgggcgagtc agggtattag cagctggtta acc

<210> 44
<211> 21
<212> DNA
<213> Homo sapiens

<400> 44
gctgcatcca gtttgcaaag t

<210> 45
<211> 27
<212> DNA
<213> Homo sapiens

<400> 45
caacagtatg atagttaccc tatcacc

<210> 46
<211> 11
<212> PRT
<213> Homo sapiens

<400> 46
Arg Ala Ser Gln Gly Ile Ser Ser Trp Leu Thr
 1               5                   10

<210> 47
<211> 7
<212> PRT
<213> Homo sapiens

<400> 47
Ala Ala Ser Ser Leu Gln Ser
 1               5

<210> 48
<211> 9
<212> PRT
<213> Homo sapiens

<400> 48
Gln Gln Tyr Asp Ser Tyr Pro Ile Thr
 1               5
```

```
<210> 49
<211> 291
<212> DNA
<213> Homo sapiens

<400> 49
caggtgcagc tacagcagtg gggcgcagga ctgttgaagc cttcggagac cctgtccctc    60
acctgcgctg tctatggtgg gtccttcagt ggttactact ggagctggat ccgccagccc   120
ccagggaagg ggctggagtg gattggggaa atcaatcata gtggaagcac caactacaac   180
ccgtccctca gagtcgagt  caccatatca gtagacacgt ccaagaacca gttctccctg   240
aagctgagct ctgtgaccgc cgcggacacg gctgtgtatt actgtgcgag a            291

<210> 50
<211> 285
<212> DNA
<213> Homo sapiens

<400> 50
gacatccaga tgacccagtc tccatcctca ctgtctgcat ctgtaggaga cagagtcacc    60
atcacttgtc gggcgagtca gggtattagc agctggttag cctggtatca gcagaaacca   120
gagaaagccc ctaagtccct gatctatgct gcatccagtt tgcaaagtgg ggtcccatca   180
aggttcagcg gcagtggatc tgggacagat ttcactctca ccatcagcag cctgcagcct   240
gaagattttg caacttatta ctgccaacag tataatagtt accct                   285

<210> 51
<211> 294
<212> DNA
<213> Homo sapiens

<400> 51
gaggtgcagc tggtggagtc tgggggaggc ttggtccagc tggggggtc  cctgagactc    60
tcctgtgcag cctctggatt caccttagt agctattgga tgagctgggt ccgccaggct   120
ccagggaaag ggctggagtg ggtggccaac ataaagcaag atggaagtga gaaatactat   180
gtggactctg tgaagggccg attcaccatc tccagagaca acgccaagaa ctcactgtat   240
ctgcaaatga acagcctgag agccgaggac acggctgtgt attactgtgc gaga          294

<210> 52
<211> 288
<212> DNA
<213> Homo sapiens

<400> 52
gaaattgtgt tgacgcagtc tccaggcacc ctgtctttgt ctccagggga aagagccacc    60
ctctcctgca gggccagtca gagtgttagc agcagctact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggta gctcacct                288
```

```
<210> 53
<211> 285
<212> DNA
<213> Homo sapiens

<400> 53
gaaattgtgt tgacacagtc tccagccacc ctgtctttgt ctccagggga aagagccacc  60
ctctcctgca gggccagtca gagtgttagc agctacttag cctggtacca acagaaacct 120
ggccaggctc ccaggctcct catctatgat gcatccaaca gggccactgg catcccagcc 180
aggttcagtg gcagtgggtc tgggacagac ttcactctca ccatcagcag cctagagcct 240
gaagattttg cagtttatta ctgtcagcag cgtagcaact ggcct              285
```

UNITED STATES PATENT AND TRADEMARK OFFICE
CERTIFICATE OF CORRECTION

| | | |
|---|---|---|
| PATENT NO. | : 7,387,776 B2 | Page 1 of 1 |
| APPLICATION NO. | : 10/338366 | |
| DATED | : June 17, 2008 | |
| INVENTOR(S) | : Keler et al. | |

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 231 days Delete the phrase "by 231 days" and insert -- by 521 days --

Signed and Sealed this

Eleventh Day of May, 2010

David J. Kappos
*Director of the United States Patent and Trademark Office*